US011154611B2

(12) United States Patent
Willems et al.

(10) Patent No.: US 11,154,611 B2
(45) Date of Patent: Oct. 26, 2021

(54) VACCINE AGAINST BOVINE LEUKEMIA VIRUS

(71) Applicants: UNIVERSITË DE LIÈGE, Liège (BE); INSTITUTO NACIONAL DE TECNOLOGÍA AGROPECUARIA, Buenos Aires (AR)

(72) Inventors: Luc Willems, Saint-Martin (BE); Karina Trono, Haedo (AR)

(73) Assignees: UNIVERSITÉDE LIÉGE, Liege (BE); INSTITUTO NACIONAL DE TECNOLOGIA AGROPECUARIA, Buenos Aires (AR)

( * ) Notice: Subject to any disclaimer, the term of this patent is extended or adjusted under 35 U.S.C. 154(b) by 311 days.

(21) Appl. No.: 16/006,472

(22) Filed: Jun. 12, 2018

(65) Prior Publication Data

US 2019/0000963 A1 Jan. 3, 2019

Related U.S. Application Data

(63) Continuation of application No. 14/832,863, filed on Aug. 21, 2015, now Pat. No. 10,029,006, which is a continuation of application No. PCT/EP2014/053855, filed on Feb. 27, 2014.

(60) Provisional application No. 61/769,971, filed on Feb. 27, 2013.

(30) Foreign Application Priority Data

Feb. 27, 2013 (EP) .................................... 13156921

(51) Int. Cl.
| | |
|---|---|
| *A61K 39/21* | (2006.01) |
| *C07K 14/005* | (2006.01) |
| *C12N 7/00* | (2006.01) |
| *A61K 39/12* | (2006.01) |
| *A61K 39/00* | (2006.01) |

(52) U.S. Cl.
CPC .............. *A61K 39/21* (2013.01); *A61K 39/12* (2013.01); *C07K 14/005* (2013.01); *C12N 7/00* (2013.01); *A61K 2039/5254* (2013.01); *A61K 2039/552* (2013.01); *C12N 2740/14021* (2013.01); *C12N 2740/14022* (2013.01); *C12N 2740/14034* (2013.01); *C12N 2740/14043* (2013.01); *C12N 2740/14062* (2013.01); *C12N 2740/14071* (2013.01)

(58) Field of Classification Search
None
See application file for complete search history.

(56) References Cited

FOREIGN PATENT DOCUMENTS

RU 2396978 C1 8/2010

OTHER PUBLICATIONS

Kerkhofs et al.: "Long-term protection against bovine leukaeia virus replication in cattle and sheep", J. Gen. Virol., vol. 81, 2000, pp. 957-963.
Willems et al.: "Genetic determinants of Bovine Leukemia Virus Pathogenesis.", Aids. Res. Hum. Retroviruses, vol. 16, No. 16, 2000, pp. 1787-1795.
Willems L., et al: "Attenuation of Bovine Leukemia Virus by deletion of R3 and G4 open reading fraes", Proc. Natl. Acad. Sci. USA, vol. 91, 1994, pp. 11532-11536.
Florins A et al: "Even attenuated bovine leukemia virus proviruses can be pathogenic in sheep", J. Virol, vol. 81 nr. 18, 2007, pp. 10195-10200.
International Preliminary Report on Patentability, Application No. PCT/EP2014/053855, dated Jun. 12, 2015, 22 pages.
International Search Report related to International Patent Application No. PCT/EP2014/053855, dated Jun. 25, 2014.
Gutierrez, Geronimo, et al., "A life-attenuated BLV deletant as a candidate vaccine to inhibit viral transmission in bovine herds." Retrovirology 8.Suppl 1 (2011): A12.
Gillet et al. (2007) "Mechanisms of leukemogenesis induced by bovine leukemia virus: prospects for novel anti-retroviral therapies in human," Retrovirol. 4:18. pp. 1-32.
Gupta et al. (2006) "Hemopure," Web page produced as part of a class project for BI/0108: Organ Replacement, Spring Semester 2006, Brown University. Accessible on the Internet at URL: http://biomed.brown.edu/Courses/BI108/2006-108websites/group09artificialblood/Pages/hemopure.htm. [Last Accessed Aug. 25, 2016].
GenBank (2016): D00647.
GenBank (2014): AB934283.
GenBank (2016): FJ914764.
GenBank (2017): AF257515.
GenBank (2015): LC164085.
GenBank (2012): HE967303.
GenBank (2016): K02120.
GenBank (2017): AP018023.
GenBank (2017): AP018030.

(Continued)

*Primary Examiner* — Nicole Kinsey White
(74) *Attorney, Agent, or Firm* — Lathrop GPM LLP; James H. Velema; Judith L. Stone-Hulslander

(57) ABSTRACT

The invention relates to recombinant bovine leukemia viruses that have an attenuated phenotype and comprise a combination of at least two specific mutations. The invention also provides recombinant nucleic acids encoding such viruses, vectors comprising such nucleic acids, and host cells comprising such nucleic acids or vectors. The recombinant attenuated BLV viruses, recombinant nucleic acids, vectors and host cells allow for the preparation of improved vaccines, in particular vaccines suitable for the prophylactic treatment of BLV-associated diseases in subjects. The invention further provides methods for treating BLV-associated diseases in subjects and pharmaceutical compositions suitable for use in these methods.

18 Claims, 24 Drawing Sheets

Specification includes a Sequence Listing.

(56) References Cited

OTHER PUBLICATIONS

Figure 1A:
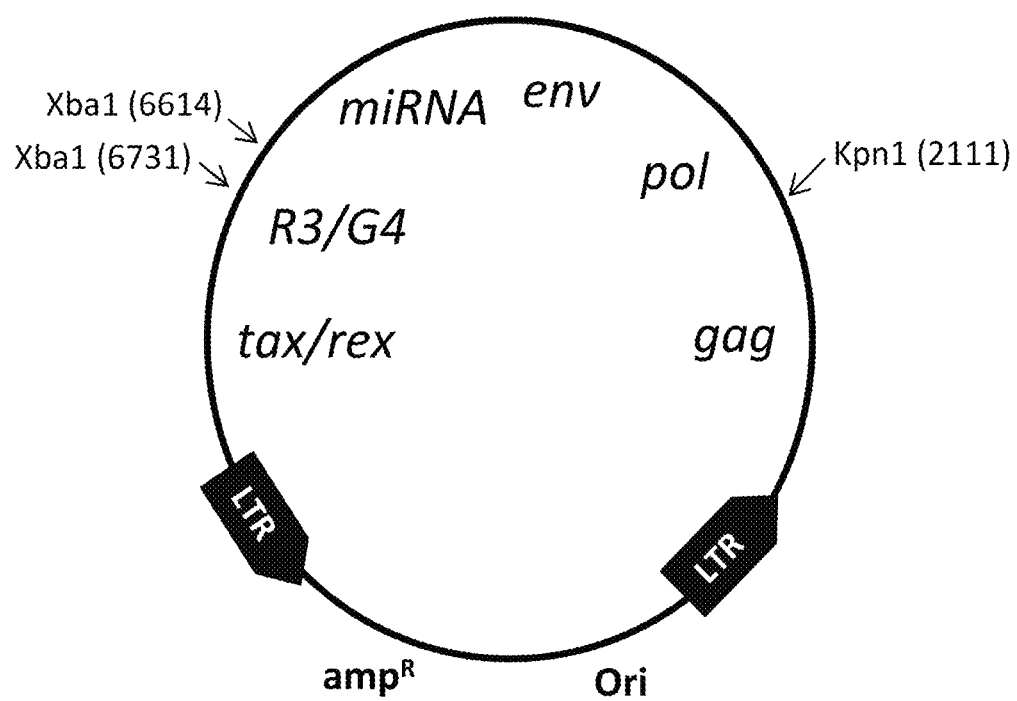

GenBank (2015): LC005616.
GenBank (2017): AB987702.
U.S. Appl. No. 16/006,472.
U.S. Appl. No. 14/832,863 / 2016/0045593 / U.S. Pat. No. 10,029,006, filed Aug. 21, 2015 / Feb. 18, 2016 / Jul. 24, 2018, Luc Willems.
PCT/EP2014/05855 / 2014/131844, Feb. 27, 2014 Sep. 4, 2014, Luc Willems.

FIG. 1D

| | |
|---|---|
| TTTCCTACGCATTCAAAATGACTCCATTATCCGCCTCGGTGATCTCCAGCCTCTCTCGCA | 5849 |
| AAGAGTCTACAGACTGGCAGTGGCCCTGGAATTGGGATCTGGGCTCACCGCCTGGGT | 5909 |
| GCGAGAAACCATTCATTCTGTTCTAAGCCTATTCCTATTAGCCCTTTTTTGCTCTTCTT | 5969 |
| GGCCCCCTGCCTGATAAAATGCTTGACCTTCTCGCCTTTAAAACTCCTCCGCAGCTCC | 6029 |
| CCACTTCCCTGAAATCTCCTTCCCCCCTAAACCGATTCTGATTATCAGGCCTTGCTACC | 6089 |
| GTCAGCACCAGAGATCTACTCTCCCCCACCCTCCCCCCACCCCTCGATTACATCAACCTTCG | 6149 |
| ACCCTGCCCTTGACACCCCGTGTTTCACGCACCCTCTTCTTGCTGCCAGCACCCGAGTTCGAACA | 6209 |
| AGTGGAATAGTCAGTGTACCATCACAAGCCTCTCTTCTTGCTGCCAGCACCGAGTTCGAACA | 6269 |
| CAGCCCTACCCTGAGCTCACTCAGTCATTTTATAGCCGATTGGGGTTCGCGCCCTCCATTGCTG | 6329 |
| TCTGCGTGTCACTCAGTCATTTTATAGCCGATTGGGGTTCGCGCCCTCCATTGCTG | 6389 |
| TGACACGGTTAAGACCTCTCTCACTTCTGCTTCACCATCCCCCTGCCAGCGTTGGTCTAG | 6449 |
| TGGAAAGAACTAACGCTGACGGGGCGATTTCTTGCAGCTGTGCTAAGCGAGAGGCTCTG | 6509 |
| GTGCTGGGATAAGATGCGGCCCTAGCACCACAGTCTCTGCGCCTTTTGGGTTCGAATC | 6569 |
| TTCCCCATGCAGCTTCCGCTTTTTACGCCCCGTGTTGCACACCCTTTCTAGAGATACCTGAA | 6629 |
| AATCTCAGCTCGCACCCCAAGGAAGGTTGTGGCTCAGAGAGGTTAAAATAGCTCGGACCGCA | 6689 |
| ACCTCCCTTTCTTTTTATTCCACCTCTACTAGGGGATGCTCAGGTCAAGTGTGCACAGAGACATTCCAGCCACATC | 6749 |
| GTTCAGAAATTCCTCTACTAGGGGATGCTCAGGTCAAGTGTGCACAGAGACATTCCAGCCACATC | 6809 |
| AAGGTCCTGATGAACATCTTCCCATGTAAACAAGCCCAGCAAGCCCAGTGCCCCATAAAGTCCCTTCCGTTTCCACAAC | 6869 |
| CAGCAGCATTTGGGCCGCTCATCTTCTATTTCCACCTCTAACAACGACTCCCCCCGAGCCCTTCAAG | 6929 |
| GCTGCCCTCGACATCTTCTATTTCCACCTCTAACAACGACTCCCCCCGAGCCCTTCAAG | 6989 |
| CTCTTCGGGATCCATTACCTGATAACGACAAAATTATTTCTTGTCTTTTAAGCAAGTGTT | 7049 |
| GTTGGTTGGGGGCCCCCACTCTCTACATGCCCCCCTGCGGCCCATGAACGACTCCAATTCGAAAGGATC | 7109 |
| ACCATCGATGCCTGGTGCCCCCCTGCGGCCCATGAACGACTCCAATTCGAAAGGATC | 7169 |
| GACACCACGCTCACCTGCGAGACCACCGTATCACCTGGACCGCCGATGGACGACCTTTT | 7229 |
| GGCCTCAATGGAACATTGTTCCCTGACTGTCTCCGAGACGTCTCCGAGACGTCTCCGAGACCCCCAAGGGCCC | 7289 |
| CGACGACTCTGGATCAACTGCCCCCCTTCCGGCCGTTCCGGCGCTTCCGGCGCTTCCGGCGCTTCAGGCTTCA | 7349 |
| CTTTCCCCCTTCGAGCAGTCCCCCCTTCCAGCCCTACCAGCCCTACCAATGCCAATGCCAATGTCCCCTCGGCCTCT | 7409 |

(SEQ ID NO: 16)

FIG. 8
FIG. 8A
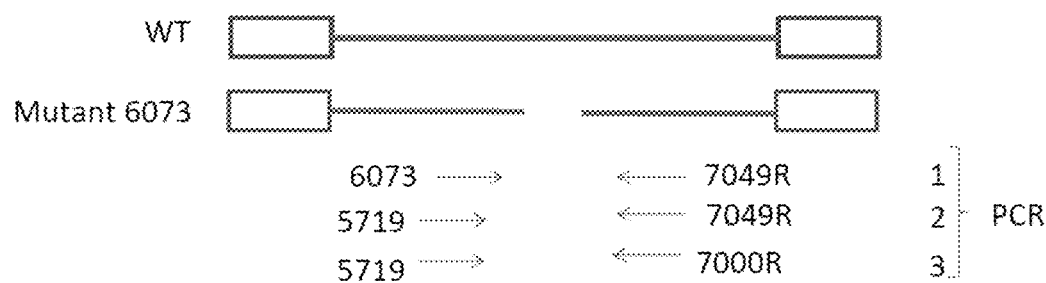
FIG. 8B
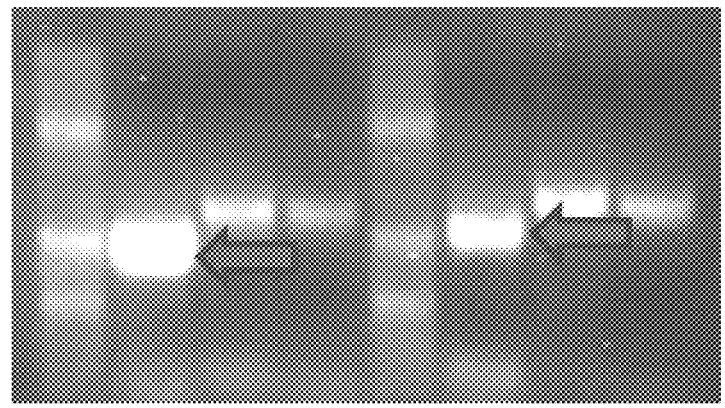

FIG. 11A

```
   1  TATAGTGTCA CCTAAATCGT ATGTGTATGA TACATAAGGT TATGTATTAA TTGTAGCCGC
  61  GTTCTAACGA CAATATGTAC AAGCCTAATT GTGTAGCATC TGGCTTACTG AAGCAGACCC
 121  TATCATCTCT CTCGTAAACT GCCGTCAGAG TCGGTTTGGT TGGACGAACC TTCTGAGTTT
 181  CTGGTAACGC CGTCCCGCAC CCGGAAATGG TCAGCGAACC AATCAGCAGG GTCATCGCTA
 241  GCCAGATCCT CTACGCCGGA CGCATCGTGG CCGGCCACAC CGGCGCCACA GGTGCGGTTG
 301  CTGGCGCCTA TATCGCCGAC ATCACCGATG GGGAAGATCG GGCTCGCCAC TTCGGCTCA
 361  TGAGCGCTTG TTTCGGCGTG GGTATGGTGG CAGGCCCCGT GGCCGGGGGA CTGTTGGGCG
 421  CCATCTCCTT GCATGCACCA TTCCTTGCGG CGGCCGGTGCT CAACGGCCTC AACCTACTAC
 481  TGGGCTGCTT CCTAATGCAG GAGTCGCATA AGGGAGAGCG TCGAATGGTG CACTCTCAGT
 541  ACAATCTGCT CTGATGCCGC ATAGTTAAGC CAGCCCCGAC ACCCGCCAAC ACCCGCTGAC
 601  GCGCCCTGAC GGGCTTGTCT GCTCCCGGCA TCCGCTTACA GACAAGCTGT GACCGTCTCC
 661  GGGAGCTGCA TGTGTCAGAG GTTTTCACCG TCATCACCGA AACGCGCGAG ACGAAAGGGC
 721  CTCGTGATAC GCCTATTTTT ATAGGTTAAT GTCATGATAA TAATGGTTTC TTAGACGTCA
 781  GGTGGCACTT TTCGGGGAAA TGTGCGCGGA ACCCCTATTT GTTTATTTTT CTAAATACAT
 841  TCAAATATGT ATCCGCTCAT GAGACAATAA CCCTGATAAA TGCTTCAATA ATATTGAAAA
 901  AGGAAGAGTA TGAGTATTCA ACATTTCCGT GTCGCCCTTA TTCCCTTTTT TGCGGCATTT
 961  TGCCTTCCTG TTTTTGCTCA CCCAGAAACG CTGGTGAAAG TAAAAGATGC TGAAGATCAG
1021  TTGGGTGCAC GAGTGGGTTA CATCGAACTG GATCTCAACA GCGGTAAGAT CCTTGAGAGT
1081  TTTCGCCCCG AAGAACGTTT TCCAATGATG AGCACTTTTA AAGTTCTGCT ATGTGGCGCG
1141  GTATTATCCC GTATTGACGC CGGGCAAGAG CAACTCGGTC GCCGCATACA CTATTCTCAG
1201  AATGACTTGG TTGAGTACTC ACCAGTCACA GAAAAGCATC TTACGGATGG CATGACAGTA
1261  AGAGAATTAT GCAGTGCTGC CATAACCATG AGTGATAACA CTGCGGCCAA CTTACTTCTG
1321  ACAACGATCG GAGGACCGAA GGAGCTAACC GCTTTTTTGC ACAACATGGG GGATCATGTA
1381  ACTCGCCTTG ATCGTTGGGA ACCGGAGCTG AATGAAGCCA TACCAAACGA CGAGCGTGAC
1441  ACCACGATGC CTGTAGCAAT GGCAACAACG TTGCGCAAAC TATTAACTGG CGAACTACTT
1501  ACTCTAGCTT CCCGGCAACA ATTAATAGAC TGGATGGAGG CGGATAAAGT TGCAGGACCA
```

FIG. 11B

```
1561  CTTCTGCGCT CGGCCCTTCC GGCTGGCTGG TTTATTGCTG ATAAATCTGG AGCCCGGTGAG
1621  CGTGGGTCTC GCGGGTATCAT TGCAGCACTG GGGCCAGATG GTAAGCCCTC CCGTATCGTA
1681  GTTATCTACA CGACGGGGAG TCAGGCAACT ATGGATGAAC GAAATAGACA GATCGCTGAG
1741  ATAGGTGCCT CACTGATTAA GCATTGGTAA CTGTCAGACC AAGTTTACTC ATATATACTT
1801  TAGATTGATT TAAAACTTCA TTTTTAATTT AAAAGGATCT AGGTGAAGAT CCTTTTTGAT
1861  AATCTCATGA CCAAAATCCC TTAACGTGAG TTTTCGTTCC ACTGAGCGTC AGACCCCGTA
1921  GAAAAGATCA AAGGATCTTC TTGAGATCCT TTTTTTCTGC GCGTAATCTG CTGCTTGCAA
1981  ACAAAAAAAC CACCGCTACC AGCGGTGGTT TGTTTGCCGG ATCAAGAGCT ACCAACTCTT
2041  TTTCCGAAGG TAACTGGCTT CAGCAGAGCG CAGATACCAA ATACTGTTCT TCTAGTGTAG
2101  CCGTAGTTAG GCCACCACTT CAAGAACTCT GTAGCACCGC CTACATACCT CGCTCTGCTA
2161  ATCCTGTTAC CAGTGGCTGC TGCCAGTGGC GATAAGTCGT GTCTTACCGG GTTGGACTCA
2221  AGACGATAGT TACCGGATAA GGCGCAGCGG TCGGGCTGAA CGGGGGGTTC GTGCACACAG
2281  CCCAGCTTGG AGCGAACGAC CTACACCGAA CTGAGATACC TACAGCGTGA GCTATGAGAA
2341  AGCGCCACGC TTCCCGAAGG GAGAAAGGCG GACAGGTATC CGGTAAGCGG CAGGGTCGGA
2401  ACAGGAGAGC GCACGAGGGA GCTTCCAGGG GGAAACGCCT GGTATCTTTA TAGTCCTGTC
2461  GGGTTTCGCC ACCTCTGACT TGAGCGTCGA TTTTTGTGAT GCTCGTCAGG GGGGCGGAGC
2521  CTATGGAAAA ACGCCAGCAA CGCGGCCTTT TTACGGTTCC TGGCCTTTTG CTGGCCTTTT
2581  GCTCACATGT TCTTTCCTGC GTTATCCCCT GATTCTGTGG ATAACCGTAT TACCGCCTTT
2641  GAGTGAGCTG ATACCGCTCG CCGCAGCCGA ACGACCGAGC GCAGCGAGTC AGTGAGCGAG
2701  GAAGCGGAAG AGCGCCCAAT ACGCAAACCG CCTCTCCCCG CGCGTTGGCC GATTCATTAA
2761  TGCAGCTGGC ACGACAGGTT TCCCGACTGG AAAGCGGGCA GTGAGCGCAA CGCAATTAAT
2821  GTGAGTTAGC TCACTCATTA GGCACCCCAG GCTTTACACT TTATGCTTCC GGCTCGTATG
2881  TTGTGTGGAA ATTGTGAGCGG ATAACAATTT CACACAGGAA ACAGCTATGA CATGATTACG
2941  AATTCTGCTT CTCAAGGTCC AAAACCAAAGA TTTAGTCTCA CCTTCCTGTG TTTAATGTTT
3001  ACGCGGTTCT GTTTCTCTCT TTTTCACTCC AGAACAAAAA TATACCTCCA ACCTGCTCCG
3061  TTTAAGGTTT TGCGGGTAAG GAGGTGGGGG TGGGAGGGA TCTTTTCTGA AAGATATTTA
3121  AAAAAAGGTA TCAGAGCAAA GATTAAAACA TGGAAAAGTG TATGAAAGAT CATGCCGGCC
```

FIG. 11C

```
3181  TAGGCGCCGC CACCGCCCCG TAAAACCAGAC AGAGACGTCA GCTGCCAGAA AAGCTGGTGA
3241  CGGCAGCTGG TGGCTAGAAT CCCCGTACCT CCCCAACTTC CCCTTTCCCG AAAAATCCAC
3301  ACCCCGAGCT GCTGACCTCA CCTGCTGATA AAACAATAAA ATGCCGGCCC TGTCGAGTTA
3361  GCGGCACCAG AAGCGTTCTC CTCCTGAGAC CTCGTGTCTC AGCTCTCGT CCTGAGCTCT
3421  CTTGCTCCCG AGACCTTCTG GTCGGCTATC CGGCAGCGGT CAGGTAAGGC AAACCACGGT
3481  TTGGAGGGTG GTTCTCGGCT GAGACCACCG CGAGCTCTAT CTCCGGTCCT CTGACCGTCT
3541  CCACGTGGAC TCTCTCTCTT GCCTCCTGAC GAGACTCTCC AAGGGCGTCT GGCTTGCACC
3601  CGCGCTTGTT TCCTGTCTTA CTTTCTGTTT CTCGCGGCCC GCGCTCTCTC CTTCGGCGCC
3661  CTCTAGCGGC CAGGAGAGAC CGGCAAACAA TTGGGGGCTC GTCCGGGATT GATCACCCCG
3721  GAACCCTAAC AATCCTCTGG ACCCACCCC TCGGCGGCGT TTTGGGTCTT TCCTTTAAAT
3781  TATATCATGG GAAATTCCCC CTCCTATAAC GTATCTCCCC CTCAGACTGG
3841  CTCAACCTTT TGCAAAGCGC GCAAAGGCTC AATCCGCGAC CCTCTCCTAG CGATTTTACC
3901  GATTTAAAAA ATTACATCCA TTGGTTTCAT AAGACCCAGA AAAAACCATG GACTTTCACT
3961  TCTGGTGGCC CCGCCTCATG CCCACCCGGG AAATTCGGCC GGGTTCCCCT TGTCTTGCC
4021  ACCCTAAACG AAGTGCTCTC AAACGATGAG GGCGCCCCGG GTGCATCGGC CCCAGAAGAA
4081  CAACCCCCC CTTATGACCC CCCGCCGTT TTGCCAATCA TATCTGAAGG GAATCGCAAC
4141  CGCCATCGCG CTTGGGCACT CCGAGAATTA CAAGATATTA AAAAAGAAAT TGAAAATAAG
4201  GCACCGGGTT CGCAAGTATG GATACAAACA CTACGACTTG CAATCTTGCA GGCCGACCCT
4261  ACTCCTGCTG ACCTAGAACA ACTTTGCCAA TATATTGCTT CCCGGTCGA TCAAACGGCC
4321  CACATGACCA GCCTAACGGC AGCAATAGCA GCCGCTGAAG CGGCCAACAC CCTTCAGGGT
4381  TTTAATCCCC AAAAACGGGAC CCTGACCCAA GCCGCTGAAC AGCCCAACGC CGGGGATCTT
4441  AGAAGTCAAT ATCAAAACCT TTGGCTTCAG GCCTGGAAAA ATCTCCCTAC TCGTCCTTCA
4501  GTACAACCCT GGTCCACCAT CGTCCAAGGC CCCGCCGAGA GCTATGTAGA GTTTGTCAAC
4561  CGGTTACAAA TTTCATTAGC TGACAACCTT CCCCTAAAGA TCCCTAAAGA ACCCATTATT
4621  GACTCCCTTA GCTATGCTAA TGCTAACAAA GAATGCCAAC AAATTTTGCA GGGGCGGGGC
4681  CTAGTGGCCG CCCCGGTGGG ACAAAAACTG CAGGCTTGTG CACATTGGGC CCCAAGATT
4741  AAACAGCCTG CAATCCTCGT CCACCCCCA GGGCCCAAGA TGCCCGGGCC TCGGCAACCG
```

FIG. 11D

```
4801 GCCCCCAAAA GGCCCCCCCC GGGACCATGC TATCGATGCC TCAAAGAAGG CCATTGGGCC
4861 CGGGACTGTC CCACCAAGAC CACCGGCCCC CCTCCGGGAC CTTGTCCCAT ATGCAAAGAT
4921 CCTTCCCATT GGAAACGAGA CTGTCCAACC CTCAAATCAA AAAACTAATA GAGGGGGAC
4981 TTAGCGCCCC CCAAACCGTA ACCCCTATAA CAGATCCTCT TAGTGAGGCT GAATTGGAAT
5041 GCTTACTTTC TATTCCTCTG GCTCGCAGCC GTCCCTCCGT GGCTGTATAC CTGTCTGCC
5101 CCTGGCTGCA GCCCCTCTCAG AATCAAGCCC TTATGCTCGT GGACACCGGG GCTGAAAATA
5161 CGGTCCTCCC ACAAAATTGG CTGGTTCGAG ATTACCCACG GATCCCCGCC GCAGTGCTCG
5221 GAGCGGGGGG AGTCTCCCGG AACAGATACA ATTGGCTACA AGGCCCTCTG ACCCTGGCTC
5281 TAAAACCAGA GGGTCCCTTT ATCACCATCC CAAAAATTTT AGTTGACACT TTCGATAAAT
5341 GGCAAATTTT AGGACGGGAC GTCCTCTCCC GCCTACAGGC CTCTATCTCC ATACCTGAGG
5401 AGGTACGCCC CCCACCTGTA GGCGTCCTAG ATGCCCCCCC GAGCCACATT GGATTAGAAC
5461 ATTTGCCCGC CCCCATGGAG GTACCCTCAAT TCCCTTTAAA CTAGAACGCC TCCAGGCCCT
5521 TCAAGACCTG GTCCATCGCT CTCTGGAGGC AGGTTATATC TCCCCCTGGG ACGGGCCAGG
5581 CAATAATCCA GTATTCCCGG TACGGAAACC AAATGGCACC TGGAGGTTTG TGCATGATCT
5641 ACGAGCTACA AATGCTCTTA CAAAGCCCAT CCCGGCGCTC TCCCCCGGAC CGCCAGACCT
5701 TACCGCTATC CCTACACACC TTCCACATAT CATTTGCCTA GATCTCAAAG ATGCCTTCTT
5761 CCAGATTCCA GTCGAAGACC GCTTCCGCTC CTATTTTGCT TTTACCCTCC CTACCCCCGG
5821 GGGACTCCAA CCTCATAGAC GCTTTGCCTG GCGGGTCCTA CCTCAAGGCT TCATTAATAG
5881 CCCGGCTCTT TTCGAACGGG CACTACAGGA ACCCCTTCGC CAAGTTTCCG CCGCTTCTC
5941 CCAGTCTCTT CTGGTGTCCT TATCCTTATC GCTTCGCCTA CAGAAGAACA
6001 ACGGTCACAA TGTTATCAAG ATATGGACGA CCCTGGCTGC GACCTAGGGT TTCAGGTGGC
6061 GTCTGAAAAG ACTCGCCAGA TTCCACACC CGTCCCCTTC CTGGGACAAA TGGTCCATGA
6121 CCAGATTGTC ACCTATCAGT CTTGCAGATC TCATCCCCAA TTTCTCTTCA
6181 GGGACTCCAA CCTCATAGAC GCTTTGCCTG GCGGGTCCTA CCTCAAGGCT TCATTAATAG
6181 CCAATTACAG GCGGTCTTGG CAACTTCTCT ACTCTTCCCT TAAAGGCAT CTACTACCG
6241 CCGACCCCTG CAACTTCTCT ACTCTTCCCT TAAAGGCAT GATGACCCTA GGGCCACCAT
6301 CCAGCTTTCC CCGGAACAGC TACACAGC TGCAGAGCTT CGACAAGCCC TGTCCCATAA
6361 CGCAAGATCT AGATATAACG AGCAAGAACC CCTGCTGGCC TACATACACC TAACCCGGGC
```

FIG. 11E

```
6421  GGGGTCCACC CTGGTACTCT TCCAAAAGGG CGCTCAATTT CCCCTGGCCT ACTTTCAGAC
6481  CCCCTTGACT GACAACCAAG CCTCACCTTG GGGCCTCCTT CTCCTGCTGG GATGCCAATA
6541  CCTGCAGACT CAGGCCTTAA GCTCTTATGC CAAGCCCATA CTCAAATACT ATCACAATCT
6601  TCCTAAAACC TCTCTCGACA ATTGGATTCA GCTCTCGAG GACCCTCGAG TTCAGGAGTT
6661  GTTGCGATTG TGGCCCCAGA TTTCCTCTCA GGGAATACAG CCCCCGGGCC CCTGGAAGAC
6721  CTTGATCACC AGGGCAGAGG TTTTTTTGAC GCCCCAGTTC TCTCCTGAAC CGATTCCTGC
6781  GGCCCTTTGC CTCTTTAGTG ACGGGCTAC AGGACGAGGA GCATATTGCC TGTGGAAAGA
6841  CCACCTTTTG GACTTTCAGG CCGTTCCGGC TCCAGAGTCC GCCCAAAAGG GAGAACTAGC
6901  AGGTCTCTTG GCGGGCTTAG CAGCCGCCCC GCCTGAACCT TTAAATATAT GGGTAGATTC
6961  CAAATACCTA TACTCCTTGC TCAGAACCCT AGTTCTGGGA GCTTGGCTTC AACCTGACCC
7021  CGTACCCTCC TATGCCCCTC TATACAAAAG CCTCCTCCGA CATCCAGCAA TCTTTGTTGG
7081  TCATGTCCGG AGCCACTCCT CAGCATCCCA CCCTATTGCT TCCCTGAACA ATTATGTAGA
7141  TCAACTGCTC CCCTTAGAAA CTCCAGAGCA ATGGCATAAG CTCACCCACT GCAACTCTCG
7201  GGCCTTGTCT CGATGGCCGA ACCCACGTAT TTCGGCCTGG GATCCCCGTT CCCCCGCTAC
7261  GCTATGTGAA ACCTGTCAAA AGCTCAATCC AACTGGAGGT GGAAAGATGC GAACTATTCA
7321  GAGAGGGTGG GCCCCGAATC ATATTTGGCA GGCCGATATA ACCCATTATA AATACAAACA
7381  GTTCACCTAC GCTTTACTCT TGTTTGTAGA TACTTACTCT GGAGCTACTC ATGCCTCAGC
7441  AAAGCGAGGG CTCACCACTC AAATGACCAT AAACTGACCA CTGGAGGCCA TAGTACATCT
7501  GGGTCGTCTA AAAAAGCTAA ACACTGACCA AGGCGCAAAC TACACCTCCA AAACCTTTGT
7561  CAGGTTTTGC CAGCAGTTCG GAGTTTCCCT TTCTCATCAC GTTCCCTACA ACCCCACAAG
7621  TTCAGGGTTG GTAGAACGGA CAAATGGACT GCTCAAACTT CTTTTGTCTA AATATCACCT
7681  AGACGAACCC CACCTTCCCA TGACTCAGGC CCTTTCTCGA GCCCTCTGGA CTCACAATCA
7741  GATTAACCTC CTGCCAATTC TAAAGACCAG ATGGGAGTTA GCCCATTCAC CCCTACTTGC
7801  TGTCATTTCA GAGGGCGGAG AAACACCCAA GGGCTCTGAT AAACTCTTTT TGTACAAGCT
7861  CCCCGGGCAA AACAATCGTC GGTGGCTAGG ACCACTCCCG GCCCTAGTCG AAGCCTCGGG
7921  AGGGCGCCCTC CTGGCTACTA ACCCCCCGT GTGGGTTCCC TGGCGTTTGC TAAAAGCCTT
7981  CAAATGCCCA AAGAACGACG GTCCCACAAC CGCCCGAAGA CGATCATCAG ATGGGTAAGT
```

FIG. 11F

```
8041  CTCACTCTTA CTCTCCTCGC TCTCTGTCAG CCCATCCAGA CTTGGAGATG CTCCCTGTCC
8101  CTAGGAAATC AACAATGGAT GACAACATAT AACCAAGAGG CAAAATTTTC CATCGCCATT
8161  GACCAAATAC TAGAGGCTCA TAATCAATCG CCTTTCTGTC CCAGGTCTCC CAGATACACC
8221  TTGGACTTTG TAAATGGTTA TCCTAAGATC TATTGGCCCC CCCACAAGG GCGACGCCGG
8281  TTTGGAGCCA GGGCCATGGT CACATATGAT TGCGAGCCCC GATGCCCTTA TGTGGGGCA
8341  GATCACTTCG ACTGCCCCCA CTGGGACAAT GCTTCCCAGG CCGATCAAGG GTCCTTTTAT
8401  GTCAATCATC AGATTTTATT CCTGCATCTC AAACAATGTC ATGGAATTTT CACTCTAACC
8461  TGGGAAATAT GGGGATATGA TCCCCTGATC ACCTTTTCTT TACATAAAAT CCCTGATCCC
8521  CCTCAACCCG ACTTCCCTCA GCTGAACAGT GACTGGGTTC CTCTGTCAG GTCATGGGCC
8581  CTGCTTTTAA ATCAAACGGC ACGGGCCTTC CCAGACTGTG CTATATGTTG GGAACCTTCC
8641  CCTCCCTGGG CTCCCGAAAT ATTAGTATAT AACAAAACCA TCTCCAACTC TGGACCCGGT
8701  CTCGCCCCTCC CGGACGCCCA AATCTTCTGG GTCAACACGT CCTTGTTTAA CACCACCAA
8761  GGATGGCACC ACCCTTCCCA GAGGTTGTTG TTCAAGCAA CGCCTTATTA
8821  TTACCCCCTA TCTCCCTGGT TAATCTCTCT ACGGCTTCCT CCGCCCCTCC TACCCGGGTC
8881  AGACGCAGTC CTGCCGCAGC CCTGACCTTG GGCCTAGCCC TGTCAGTGGG GCTCACTGGA
8941  ATTAATGTAG ATTGGGATCT CCTTAGCCAT CAGAGACTCA CCTCCCTGAT CCACGTTCTG
9001  GAGCAAGATC TCCTATTAGC GATCACAGCA ATTAACCAGA CCCACTATAA TTTGCTTAAT
9061  GTGGCCTCTG TGGTCGCCCA GAACCGACGG GGGCTAGATT GGTTGTACAT CCGGCTGGGT
9121  TTTCAAAGCC TATGTCCCAC GATCAATGAA CCTTGCTGTT TCCTGCGCAT TCAAAATGAC
9181  TCCATTATCC GCCTCGGTGA TCTCCAGCCT CTCTCGCAAA GAGTCTCTAC AGACTGGCAA
9241  TGGCCCTGGA ATTGGGATCT GGGGCTCACC GCCTGGGTGC GAGAAACCAT TCATTCTGTT
9301  CTAAGCCTAT TCCTATTAGC CCTTTTTTG CTCTTCTTGG CCCCCTGCCT GATAAAATGC
9361  TTGACCTCTC GCCTTTTAAA ACTCCTCCGG CAGGCTCCCC ACTTCCCTGA AATCTCCTTC
9421  CCCCTAAAC CCGATTCTGA TTATCAGGCC TTGCTACCAT CCGCGCCAGA GATCTACTCT
9481  CACCTCTCCC CCACCAAACC CGATTACATC AACCTTCGAC CCTGCCCTTG ACACCCCCAT
9541  GTTTCACGCA CCCTCAGGCT GTGGTGGGC CGATTACAGC AACTGGCTTAG TGGAATAGTC AGTGTACCAT
9601  CACAAGCCTC TTCTTGCTGC CAGCGCCGAG TTCGAACACA GCCCTACCCT GAGCCTCTCT
```

FIG. 11G

```
9661   GAGTGCATGA CTGAGTGTAG CGCAGAGAGA TTGTCGCTTC TGCGTGTCAC TCAGTCATTT
9721   TTTATAGCCG ATTGGGGTTC GCGCCCTCCC GTTGCCTGTG ACACGGTTAA GACCTCTCTC
9781   ACTTCTGCTT CACCATCCCC CTGCCAGCGT TGGTCTAGTG GAAAGAACTA ACGCTGACGG
9841   GGGCGATTTC TTGCAGCTGT GCTAAGCGAG AGGCTCTGGT GCTGGGGATA AGATGCGGCC
9901   CCTAGCACCA CAGTCTCTGC GCCTTTTGGG TTCGAATCTT CCCCATGCAG CTTCCGCTTT
9961   TTACGCCCTG TTGCACACCC TTTCTAGAGA TACCTGAAAA TCTCAGCTCG CACCCAAGG
10021  AAGGTTGTGG CTCAGAGGTT AAAATAGCTC GGACCGCAAC CTCCCTTTCT TTTTATTCCA
10081  CCCTCGCAAG GCCCCGGGTT CTAGACCCCC TAACGGAGGT TCAAAATTTC CTCTACTAGG
10141  GGGTCGCTCA GTCCAAGTGT GCACAACATC TCTTCCAAAA GGTCCTGATG AACATCTTCC
10201  CATGTAACAA GCCCCAGCAG AGACATTCCA GCCACATCCA GCAGCATTTG GGCCGCCTTC
10261  TCTAACAGTG CCCATAAAGT CCCTTCTGTT TCCACAACGG CTGCCCTCTGC ATCTTCTATT
10321  TCCACCTCGG CACCGACTCC CCCGCCGAGC CCTTCAAGCT CTTCGGGATC CATTACCTGA
10381  TAACGACAAA ATTATTTCTT GTCTTTTAAG CAAGTGTTGT TGGTTGGGGG CCCCACTCTC
10441  TACATGCCCG CCCGGCCCTG GTTTTGTCCA ATGATGTCAC CATCGATGCC TGGTGCCCCC
10501  TCTGCGGGCC CCATGAACGA CTCCAATTCG AAAGGATCGA CACCACGCTC ACCTGGAGA
10561  CCCACCGTAT CACCTGGACC GCCGATGGAC GACCTTTTCGG CCTCAATGGA ACGTTGTTCC
10621  CTCGACTGCA TGTCTCCGAG ACCCGCCCCG AAGGCCCCG ACGACTCTGG ATCAACTGCC
10681  CCCTTCCGGC CGTTCGCGCT CAGCCCGGCC TTCCCCTTCACT TTCCCCTTC GAGCAGTCCC
10741  CCTTCCAGCC CTACCAATGC CAATTGCCCT CGGCCTCTAG CGATGGTTGC CCCATCATCG
10801  GGCACGGCCT TCTTCCCTGG AACAGCTTAG TAACGCATCC TGTCCTCGGA AAAGTCCTTA
10861  CATTAAATCA AATGGCCAAT TTTTCCTTAC TCCCCCCCTT CGATACCCTC CTTGTGGACC
10921  CCCTCCGGCT GTCCGTCTTT GCCCCGGACA CTAGGGGAGC CATACGTTAT CTCTCCACCC
10981  TTTTGACGCT ATGCCCCAGT ACTTGTATTC TACCCCTAGG CGAGCCCTTC TCTCCTAATG
11041  TCCCCATATG CCGCTTTCCC CGGGACACCA ATGAACCTCC CCTTTCAGAA TTCGAGCTGC
11101  CCCTTATCCA AACGCCCGGC CTGTCTTGGT CTGTCCCCGC GATCGACCTA TTCCTAACCG
11161  GTCCCCCTTC CCCATGCGAC CGGTTACACG TGTGGTCCAG TCCTCAGGCC TTACAACGCT
11221  TCCTCCATGA CCCCACGCTC ACCTGGTCAG AATTGGTTGC TAGCGGGAAA CTAAGACTTG
```

FIG. 11H

```
11281  ATTCACCCTT AAAATTACAG CTGTTAGAAA ATGAATGGCT CTCCCGCCTT TTTTGAGGGG
11341  GAGTCATTTG TATGAAAGAT CATGCCGGCC TAGGCGCCGC CACCGCCCCG TAAACCAGAC
11401  AGAGACGTCA GCTGCCAGAA AAGCTGGTGA CGGCAGCTGG TGGCTAGAAT CCCCGTACCT
11461  CCCCAACTTC CCCTTTCCCG AAAAATCCAC ACCCCGAGCT GCTGACCTCA CCTGCTGATA
11521  AAACAATAAA ATGCCGGCCC TGTCGAGTTA GCGGCACCAG AAGCGTTCTC CTCCTGAGAC
11581  CCTCGTGCTC AGCTCTCGGT CCTGAGCTCT CTTGCTCCCG AGACCTTCTG GTCGGCTATC
11641  CGGCAGCGGT CAGGTAAGGC AAACCACGGT TTGGAGGGTG GTTCTCGGCT GAGACCACCG
11701  CGAGCTCTAT CTCCGGTCCT CTGACCGTCT CCACGTGGAC CGCGCTTGTT GCCTCCCTGA
11761  CCCGCGCTCC AAGGGCGTCT GGCTTGCACC CGCGCTTCTT TCCTGTCTTA CTTTCTGTTT
11821  CTCGCGGCCC GCGCTCTCTC GCGCTCTCTC CTCTAGCGGC CAGGAGAGAC CGGCAAACAG
11881  AAAAGTTGTA CACACATTTT ACTTACAATG TCTAACGAGG TTTTAAACCG TCGACTGTCA
11941  ACGTCAGGAG AGCCCTTCGA GCGTTCTTTC TGCTTCAAGA CGCGGGGCTG CACCCCTCGG
12001  ACGCCGCCGA ACTGAACGTC GCCCCGTCCC TGCCCACGTG ATGGAGACCT CCGCGGGGAG
12061  GGTAGGCGCC CGCGGAATGC TGGGACTGGT AGGCGCCGGC TCCTCCCCCT CCTCCCCCAG
12121  GCGTCACCCC CGGCTCCACT CCCCCAGCAG AGGCCCGGCTG GGCGGGAGGC TGGAGGCGTG
12181  GGGAGAGCAG GGACAGAACC GCAAAAGGCTC CCAGCGTTCT CGCAGCGTTGCG CTGCTCTCTG
12241  ACCTGAAGGC AGACATCTCT GCAACATATT GGAGGGCCCT GGAATTGGTG AATGGCCAGA
12301  GAGGCCTGGC GCAGCCCTTG GGGTCGCAGA GTCGGACACG ACTGAACGAC AGAACTGAAC
12361  TGAACCGAGC CCTTAAAAAA CCTAAAGCTC AGAGGCTTGA GGAACCAATG GAACCAACGC
12421  AGTGAGCGGC ACTAGCCAAT GATAATGGCA AGCACCCGGTC AGCTTGTGTAT TC
```

SEQ ID NO: 39

SEQUENCE LISTING

<160> NUMBER OF SEQ ID NOS: 39

<210> SEQ ID NO 1
<211> LENGTH: 12
<212> TYPE: DNA
<213> ORGANISM: Artificial
<220> FEATURE:
<223> OTHER INFORMATION: oligonucleotide

<400> SEQUENCE: 1
ctagaaagct tg                                                          12

<210> SEQ ID NO 2
<211> LENGTH: 12
<212> TYPE: DNA
<213> ORGANISM: Artificial
<220> FEATURE:
<223> OTHER INFORMATION: oligonucleotide

<400> SEQUENCE: 2
gatccaagct tt                                                          12

<210> SEQ ID NO 3
<211> LENGTH: 24
<212> TYPE: DNA
<213> ORGANISM: Artificial
<220> FEATURE:
<223> OTHER INFORMATION: oligonucleotide

<400> SEQUENCE: 3
gatctaggct agaattctag ccta                                             24

<210> SEQ ID NO 4
<211> LENGTH: 12
<212> TYPE: DNA
<213> ORGANISM: Artificial
<220> FEATURE:
<223> OTHER INFORMATION: oligonucleotide

<400> SEQUENCE: 4
tctagaaagc tt                                                          12

<210> SEQ ID NO 5
<211> LENGTH: 23
<212> TYPE: DNA
<213> ORGANISM: Artificial
<220> FEATURE:
<223> OTHER INFORMATION: primer for amplification in bovine leukemia
     virus (BLV) sequence

<400> SEQUENCE: 5
gaaactccag agcaatggca taa                                              23

<210> SEQ ID NO 6
<211> LENGTH: 18
<212> TYPE: DNA
<213> ORGANISM: Artificial
<220> FEATURE:
<223> OTHER INFORMATION: primer for amplification in bovine leukemia
     virus (BLV) sequence

<400> SEQUENCE: 6
ggttcggcca tcgagaca                                                    18

<210> SEQ ID NO 7
<211> LENGTH: 20

```
<212> TYPE: DNA
<213> ORGANISM: Artificial
<220> FEATURE:
<223> OTHER INFORMATION: primer for amplification in actin sequence

<400> SEQUENCE: 7
tccctggaga agagctacga                                           20

<210> SEQ ID NO 8
<211> LENGTH: 20
<212> TYPE: DNA
<213> ORGANISM: Artificial
<220> FEATURE:
<223> OTHER INFORMATION: primer for amplification in actin sequence

<400> SEQUENCE: 8
ggcagactta gcctccagtg                                           20

<210> SEQ ID NO 9
<211> LENGTH: 21
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 9
ctcacttctg cttcaccatc c                                         21

<210> SEQ ID NO 10
<211> LENGTH: 20
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 10
ggcaggcatg tagagagtgg                                           20

<210> SEQ ID NO 11
<211> LENGTH: 22
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 11
tggaaagaac taacgctgac gg                                        22

<210> SEQ ID NO 12
<211> LENGTH: 22
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 12
ccccaaccaa caacacttgc tt                                        22

<210> SEQ ID NO 13
<211> LENGTH: 26
<212> TYPE: DNA
<213> ORGANISM: Artificial
<220> FEATURE:
```

<223> OTHER INFORMATION: primer for amplification in bovine leukemia
     virus (BLV) sequence

<400> SEQUENCE: 13
tctagagggg gtgtcaaggg cagggt 26

<210> SEQ ID NO 14
<211> LENGTH: 19
<212> TYPE: DNA
<213> ORGANISM: Artificial
<220> FEATURE:
<223> OTHER INFORMATION: primer for site directed mutagenesis in bovine
leukemia virus (BLV) sequence

<400> SEQUENCE: 14
gattctgatg atcaggcct 19

<210> SEQ ID NO 15
<211> LENGTH: 19
<212> TYPE: DNA
<213> ORGANISM: Artificial
<220> FEATURE:
<223> OTHER INFORMATION: primer for site directed mutagenesis in bovine
leukemia virus (BLV) sequence

<400> SEQUENCE: 15
aggcctgatc atcagaatc 19

<210> SEQ ID NO 16
<211> LENGTH: 1620
<212> TYPE: DNA
<213> ORGANISM: Bovine leukemia virus

<400> SEQUENCE: 16
tttcctacgc attcaaaatg actccattat ccgcctcggt gatctccagc ctctctcgca 60
aagagtctct acagactggc agtggccctg gaattgggat ctggggctca ccgcctgggt 120
gcgagaaacc attcattctg ttctaagcct attcctatta gcccttttt tgctcttctt 180 ggccccctgc ctgataaaat gcttgacctc tcgcctttta aaactcctcc ggcaggctcc 240
ccacttccct gaaatctcct tccccctaa acccgattct gattatcagg ccttgctacc 300
gtcagcacca gagatctact ctcacctctc cccccaccaaa cccgattaca tcaaccttcg 360
accctgccct tgacaccccc gtgtttcacg caccctcagg ctgtggtggg gcactggctt 420
agtggaatag tcagtgtacc atcacaagcc tcttcttgct gccagcaccg agttcgaaca 480
cagccctacc ctgagcctct ctgagtacat gactgagtgt agcgcagaga ggttgtcgct 540
tctgcgtgtc actcagtcat tttttatagc cgattggggt tcgcgccctc ccattgcctg 600
tgacacggtt aagacctctc tcacttctgc ttcaccatcc ccctgccagc gttggtctag 660
tggaaagaac taacgctgac gggggcgatt tcttgcagct gtgctaagcg agaggctctg 720
gtgctgggga taagatgcgg cccctagcac cacagtctct gcgccttttg ggttcgaatc 780
ttccccatgc agcttccgct ttttacgccc tgttgcacac cctttctaga gatacctgaa 840
aatctcagct cgcaccccaa ggaaggttgt ggctcagagg ttaaaatagc tcggaccgca 900
acctcccttt ctttttattc caccctcgca aggccccggg ttctgggccc cctaacggag 960
gttcagaatt tcctctacta ggggatgctc aggtccaagt gtgcacaata tctcttccaa 1020
aaggtcctga tgaacatctt cccatgtaac aagccccagc agagacattc cagccacatc 1080
cagcagcatt tgggccgcct tctctaacag tgcccataaa gtcccttccg tttccacaac 1140

```
ggctgcctct gcatcttcta tttccacctc ggcaccgact ccccgccga gcccttcaag    1200 ctcttcggga tccattacct gataacgaca aaattattc ttgtctttta agcaagtgtt     1260
gttggttggg ggccccactc tctacatgcc tgcccggccc tggttttgtc caatgatgtc    1320
accatcgatg cctggtgccc cctctgcggg cccatgaac gactccaatt cgaaaggatc     1380
gacaccacgc tcacctgcga gacccaccgt atcacctgga ccgccgatgg acgacctttt    1440
ggcctcaatg gaacattgtt ccctcgactg catgtctccg agacccgccc caagggccc    1500 cgacgactct ggatcaactg ccccttccg gccgttcgcg ctcagcccgg ccggtttca     1560 ctttccccct tcgagcagtc ccccttccag ccctaccaat gccaatgtcc ctcggcctct   1620
```

```
<210> SEQ ID NO 17
<211> LENGTH: 19
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 17
tgacaacata taaccaaga                                                19

<210> SEQ ID NO 18
<211> LENGTH: 27
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 18
tctagacaga gacattccag ccacatc                                       27

<210> SEQ ID NO 19
<211> LENGTH: 23
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 19
cctgcatgat ctttcataca aat                                           23

<210> SEQ ID NO 20
<211> LENGTH: 23
<212> TYPE: DNA
<213> ORGANISM: Bovine leukemia virus

<400> SEQUENCE: 20
tcagtgtacc atcacaagcc tct                                           23

<210> SEQ ID NO 21
<211> LENGTH: 22
<212> TYPE: DNA
<213> ORGANISM: Bovine leukemia virus

<400> SEQUENCE: 21
atgactgagt gtagcgcaga ga                                            22

<210> SEQ ID NO 22
<211> LENGTH: 21
<212> TYPE: DNA
```

```
<213> ORGANISM: Bovine leukemia virus

<400> SEQUENCE: 22
tgcgtgtcrc tcagtcattt t                                          21

<210> SEQ ID NO 23
<211> LENGTH: 21
<212> TYPE: DNA
<213> ORGANISM: Bovine leukemia virus

<400> SEQUENCE: 23
atccccctgc cagcgttggt c                                          21

<210> SEQ ID NO 24
<211> LENGTH: 23
<212> TYPE: DNA
<213> ORGANISM: Bovine leukemia virus

<400> SEQUENCE: 24
taacgctgac gggggcgatt tct                                        23

<210> SEQ ID NO 25
<211> LENGTH: 24
<212> TYPE: DNA
<213> ORGANISM: Bovine leukemia virus

<400> SEQUENCE: 25
tagcaccayv gtctctgcgc cttt                                       24

<210> SEQ ID NO 26
<211> LENGTH: 22
<212> TYPE: DNA
<213> ORGANISM: Bovine leukemia virus

<400> SEQUENCE: 26
aggarggttg tggctcagag gt                                         22

<210> SEQ ID NO 27
<211> LENGTH: 23
<212> TYPE: DNA
<213> ORGANISM: Bovine leukemia virus

<400> SEQUENCE: 27
ctcgrrccgc aacctccctt tct                                        23

<210> SEQ ID NO 28
<211> LENGTH: 22
<212> TYPE: DNA
<213> ORGANISM: Bovine leukemia virus

<400> SEQUENCE: 28
aggctgtggt ggbgcrctgg ct                                         22

<210> SEQ ID NO 29
<211> LENGTH: 22
<212> TYPE: DNA
<213> ORGANISM: Bovine leukemia virus

<400> SEQUENCE: 29
aagcgrgagg ctctggtgct gg                                         22

<210> SEQ ID NO 30
<211> LENGTH: 20
```

```
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 30
cgggggcttg attggttgta                                                    20

<210> SEQ ID NO 31
<211> LENGTH: 21
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 31
ttgtcgttat caggtaatgg a                                                  21

<210> SEQ ID NO 32
<211> LENGTH: 22
<212> TYPE: DNA
<213> ORGANISM: Artificial
<220> FEATURE:
<223> OTHER INFORMATION: primer for amplification in bovine leukemia
      virus (BLV) sequence

<400> SEQUENCE: 32
ccccaaccaa caacacttgc tt                                                 22

<210> SEQ ID NO 33
<211> LENGTH: 43
<212> TYPE: DNA
<213> ORGANISM: Artificial
<220> FEATURE:
<223> OTHER INFORMATION: primer for amplification in Bacillus subtilis

<400> SEQUENCE: 33 cctttttgctc acatgtaaca aaattctcca gtcttcacat cgg                         43

<210> SEQ ID NO 34
<211> LENGTH: 43
<212> TYPE: DNA
<213> ORGANISM: Artificial
<220> FEATURE:
<223> OTHER INFORMATION: primer for amplification in Bacillus subtilis

<400> SEQUENCE: 34
gcaggaaaga acatgtcgat cagaccagtt tttaatttgt gtg                          43

<210> SEQ ID NO 35
<211> LENGTH: 42
<212> TYPE: DNA
<213> ORGANISM: Artificial
<220> FEATURE:
<223> OTHER INFORMATION: primer for amplification in Bacillus subtilis

<400> SEQUENCE: 35
gttttaaacc gtcgatcgca ttgaaactga ctgaagagta tg                           42

<210> SEQ ID NO 36
<211> LENGTH: 26
<212> TYPE: DNA
<213> ORGANISM: Artificial
<220> FEATURE:
<223> OTHER INFORMATION: primer for amplification in Bacillus subtilis
```

<400> SEQUENCE: 36
atgtcgagaa aagcgccgaa aaatcg                                          26

<210> SEQ ID NO 37
<211> LENGTH: 35
<212> TYPE: DNA
<213> ORGANISM: Artificial
<220> FEATURE:
<223> OTHER INFORMATION: primer for amplification in Bacillus subtilis

<400> SEQUENCE: 37
ttcggcgctt ttctcgacat ggatgagcga tgatg                                35

<210> SEQ ID NO 38
<211> LENGTH: 36
<212> TYPE: DNA
<213> ORGANISM: Artificial
<220> FEATURE:
<223> OTHER INFORMATION: primer for amplification in Bacillus subtilis

<400> SEQUENCE: 38
gacgttgaca gtcgactcaa tggggaagag aaccgc                               36

<210> SEQ ID NO 39
<211> LENGTH: 12472
<212> TYPE: DNA
<213> ORGANISM: Bovine leukemia virus

<400> SEQUENCE: 39
tatagtgtca cctaaatcgt atgtgtatga tacataaggt tatgtattaa ttgtagccgc     60
gttctaacga caatatgtac aagcctaatt gtgtagcatc tggcttactg aagcagaccc    120
tatcatctct ctcgtaaact gccgtcagag tcggtttggt tggacgaacc ttctgagttt    180
ctggtaacgc cgtcccgcac ccggaaatgg tcagcgaacc aatcagcagg gtcatcgcta    240
gccagatcct ctacgccgga cgcatcgtgg ccggcatcac cggcgccaca ggtgcggttg    300
ctggcgccta tcgccgac atcaccgatg gggaagatcg ggctcgccac ttcgggctca     360
tgagcgcttg tttcggcgtg ggtatggtgg caggccccgt ggccggggga ctgttgggcg    420
ccatctcctt gcatgcacca ttccttgcgg cggcggtgct caacggcctc aacctactac    480
tgggctgctt cctaatgcag gagtcgcata agggagagcc tcgaatggtg cactctcagt    540
acaatctgct ctgatgccgc atagttaagc cagccccgac accgccaac accgctgac     600
gcgccctgac gggcttgtct gctcccggca tccgcttaca gacaagctgt gaccgtctcc    660
gggagctgca tgtgtcagag gttttcaccg tcatcaccga aacgcgcgag acgaaagggc    720
ctcgtgatac gcctattttt ataggttaat gtcatgataa taatggtttc ttagacgtca    780
ggtggcactt tcggggaaaa tgtgcgcgga acccctattt gtttattttt ctaaatacat    840
tcaaatatgt atccgctcat gagacaataa ccctgataaa tgcttcaata atattgaaaa    900
aggaagagta tgagtattca acatttccgt gtcgccctta ttccctttttt tgcggcattt    960
tgccttcctg ttttgctca cccagaaacg ctggtgaaag taaaagatgc tgaagatcag   1020
ttgggtgcac gagtgggtta catcgaactg gatctcaaca gcggtaagat ccttgagagt   1080
tttcgccccg aagaacgttt tccaatgatg agcactttta aagttctgct atgtggcgcg   1140
gtattatccc gtattgacgc cgggcaagag caactcggtc gccgcataca ctattctcag   1200
aatgacttgg ttgagtactc accagtcaca gaaaagcatc ttacggatgg catgacagta   1260

```
agagaattat gcagtgctgc cataaccatg agtgataaca ctgcggccaa cttacttctg    1320
acaacgatcg gaggaccgaa ggagctaacc gcttttttgc acaacatggg ggatcatgta    1380
actcgccttg atcgttggga accggagctg aatgaagcca taccaaacga cgagcgtgac    1440
accacgatgc ctgtagcaat ggcaacaacg ttgcgcaaac tattaactgg cgaactactt    1500
actctagctt cccggcaaca attaatagac tggatggagg cggataaagt tgcaggacca    1560
cttctgcgct cggcccttcc ggctggctgg tttattgctg ataaatctgg agccggtgag    1620
cgtgggtctc gcggtatcat tgcagcactg gggccagatg gtaagccctc ccgtatcgta    1680
gttatctaca cgacggggag tcaggcaact atggatgaac gaaatagaca gatcgctgag    1740
ataggtgcct cactgattaa gcattggtaa ctgtcagacc aagtttactc atatatactt    1800
tagattgatt taaaacttca ttttaattt aaaaggatct aggtgaagat cctttttgat    1860
aatctcatga ccaaaatccc ttaacgtgag ttttcgttcc actgagcgtc agaccccgta    1920
gaaaagatca aaggatcttc ttgagatcct ttttttctgc gcgtaatctg ctgcttgcaa    1980
acaaaaaaac caccgctacc agcggtggtt tgtttgccgg atcaagagct accaactctt    2040
tttccgaagg taactggctt cagcagagcg cagataccaa atactgttct tctagtgtag    2100
ccgtagttag gccaccactt caagaactct gtagcaccgc ctacatacct cgctctgcta    2160
atcctgttac cagtggctgc tgccagtggc gataagtcgt gtcttaccgg gttggactca    2220
agacgatagt taccggataa ggcgcagcgg tcgggctgaa cggggggttc gtgcacacag    2280
cccagcttgg agcgaacgac ctacaccgaa ctgagatacc tacagcgtga gctatgagaa    2340
agcgccacgc ttcccgaagg gagaaaggcg gacaggtatc cggtaagcgg cagggtcgga    2400
acaggagagc gcacgaggga gcttccaggg ggaaacgcct ggtatcttta tagtcctgtc    2460
gggtttcgcc acctctgact tgagcgtcga ttttgtgat gctcgtcagg ggggcggagc    2520
ctatggaaaa acgccagcaa cgcggccttt ttacggttcc tggccttttg ctggccttt    2580 gctcacatgt tctttcctgc gttatcccct gattctgtgg ataaccgtat taccgccttt    2640
gagtgagctg ataccgctcg ccgcagccga acgaccgagc gcagcgagtc agtgagcgag    2700
gaagcggaag agcgcccaat acgcaaaccg cctctccccg cgcgttggcc gattcattaa    2760
tgcagctggc acgacaggtt tcccgactgg aaagcgggca gtgagcgcaa cgcaattaat    2820
gtgagttagc tcactcatta ggcaccccag gctttacact ttatgcttcc ggctcgtatg    2880
ttgtgtggaa ttgtgagcgg ataacaattt cacacaggaa acagctatga catgattacg    2940
aattctgctt ctcaaggtcc aaaccaaaga tttagtctca ccttcctgtg tttaatgttt    3000
acgcggttct gtttctctct ttttcactcc agaacaaaaa tatacctcca acctgctccg    3060
tttaaggttt ttgcggtaag gaggtggggg tgggagggga tcttttctga aagatattta    3120
aaaaaaggta tcagagcaaa gattaaaaca tggaaaagtg tatgaaagat catgccggcc    3180
taggcgccgc caccgccccg taaaccgac agagacgtca gctgccagaa aagctggtga    3240
cggcagctgg tggctagaat ccccgtacct ccccaacttc ccctttcccg aaaaatccac    3300
accccgagct gctgaccatca cctgctgata aaacaataaa atgccggccc tgtcgagtta    3360
gcggcaccag aagcgttctc ctcctgagac cctcgtgctc agctctcggt cctgagctct    3420
cttgctcccg agaccttctg gtcggctatc cggcagcggt caggtaaggc aaaccacggt    3480
ttggagggtg gttctcggct gagaccaccg cgagctctat ctccggtcct ctgaccgtct    3540
ccacgtggac tctctctctt gcctcctgac cccgcgctcc aagggcgtct ggcttgcacc    3600
cgcgcttgtt tcctgtctta cttttctgttt ctcgcggccc gcgctctctc cttcggcgcc    3660
```

```
ctctagcggc caggagagac cggcaaacaa ttgggggctc gtccgggatt gatcaccccg    3720
gaaccctaac aatcctctgg acccacccc tcggcggcgt tttgggtctt tcctttaaat    3780
tatatcatgg gaaattcccc ctcctataac cccccgctg gtatctcccc ctcagactgg    3840 ctcaacctt tgcaaagcgc gcaaaggctc aatccgcgac cctctcctag cgattttacc    3900
gatttaaaaa attacatcca ttggtttcat aagacccaga aaaaccatg gactttcact    3960 tctggtggcc ccgcctcatg cccacccggg aaattcggcc gggttcccct tgtcttggcc    4020
accctaaacg aagtgctctc aaacgatgag ggcgccccgg gtgcatcggc cccagaagaa    4080
caaccccccc cttatgaccc ccccgccgtt ttgccaatca tatctgaagg gaatcgcaac    4140
cgccatcgcg cttgggcact ccgagaatta caagatatta aaaagaaat tgaaaataag    4200 gcaccgggtt cgcaagtatg gatacaaaca ctacgacttg caatcttgca ggccgaccct    4260
actcctgctg acctagaaca actttgccaa tatattgctt ccccggtcga tcaaacggcc    4320
cacatgacca gcctaacggc agcaatagca gccgctgaag cggccaacac ccttcagggt    4380
tttaatcccc aaaacgggac cctgacccaa caatcagctc agcccaacgc cggggatctt    4440
agaagtcaat atcaaaaacct ttggcttcag gcctggaaaa atctccctac tcgtccttca    4500
gtacaaccct ggtccaccat cgtccaaggc cccgccgaga gctatgtaga gtttgtcaac    4560
cggttacaaa tttcattagc tgacaacctt cccgacggag tccctaaaga acccattatt    4620 gactcccta gctatgctaa tgctaacaaa gaatgccaac aaattttgca ggggcggggc    4680
ctagtggccg ccccggtggg acaaaaactg caggcttgtg cacattgggc ccccaagatt    4740
aaacagcctg caatcctcgt ccacacccca gggcccaaga tgcccgggcc tcggcaaccg    4800 gccccaaaa ggccccccc gggaccatgc tatcgatgcc tcaaagaagg ccattgggcc    4860
cgggactgtc ccaccaagac caccggcccc cctccgggac cttgtcccat atgcaaagat    4920
ccttcccatt ggaaacgaga ctgtccaacc ctcaaatcaa aaaactaata gagggggac    4980 ttagcgcccc ccaaaccgta accctataa cagatcctct tagtgaggct gaattggaat    5040
gcttactttc tattcctctg gctcgcagcc gtccctccgt ggctgtatac ctgtctggcc    5100
cctggctgca gccctctcag aatcaagccc ttatgctcgt ggacaccggg gctgaaaata    5160
cggtcctccc acaaaattgg ctggttcgag attacccacg gatccccgcc gcagtgctcg    5220
gagcgggggg agtctcccgg aacagataca attggctaca aggccctctg accctggctc    5280
taaaaccaga gggtcccttt atcaccatcc caaaaatttt agttgacact ttcgataaat    5340
ggcaaatttt aggacgggac gtcctctccc gcctacaggc ctctatctcc atacctgagg    5400
aggtacgccc cccatggta ggcgtcctag atgcccccc gagccacatt ggattagaac    5460
atttgcccgc cccacctgag gtacctcaat tcccttaaaa ctagaacgcc tccaggccct    5520
tcaagacctg gtccatcgct ctctggaggc aggttatatc tcccctggg acgggccagg    5580 caataatcca gtattcccgg tacgaaaacc aaatggcacc tggaggtttg tgcatgatct    5640
acgagctaca aatgctctta caaagcccat cccggcgctc tccccggac cgccagacct    5700 taccgctatc cctacacacc ttccacatat catttgccta gatctcaaag atgccttctt    5760
ccagattcca gtcgaagacc gcttccgctc ctatttgct tttacccctcc ctaccccgg    5820 gggactccaa cctcatagac gctttgcctg gcgggtccta cctcaaggct tcattaatag    5880
cccggctctt ttcgaacggg cactacagga acccttcgc caagtttccg ccgccttctc    5940
ccagtctctt ctggtgtcct atatggacga tatccttatc gcttcgccta cagaagaaca    6000
```

```
acggtcacaa tgttatcaag ccctggctgc ccgcctccgg gacctagggt tcaggtggc    6060
gtctgaaaag actcgccaga cgccttcgcc cgtcccttc  ctgggacaaa tggtccatga   6120
ccagattgtc acctatcagt ccctacctac cttgcagatc tcatcccaa  tttctcttca   6180
ccaattacag gcggtcttgg gagacctcca gtgggtctcc aggggcacac ctactacccg   6240
ccgacccctg caacttctct actcttccct taaaggcatc gatgaccta  gggccaccat   6300
ccagctttcc ccggaacagc tacaaggcat gcagagctt  cgacaagccc tgtcccataa   6360
cgcaagatct agatataacg agcaagaacc cctgctggcc tacatacacc taacccgggc   6420
ggggtccacc ctggtactct tccaaaaggg cgctcaattt cccctggcct actttcagac   6480
cccccttgact gacaaccaag cctcaccttg gggcctcctt ctcctgctgg gatgccaata   6540
cctgcagact caggccttaa gctcttatgc caagcccata ctcaaatact atcacaatct   6600
tcctaaaacc tctctcgaca attggattca atcatctgag gaccctcgag ttcaggagtt   6660
gttgcgattg tggccccaga tttcctctca gggaatacag cccccgggcc cctggaagac   6720
cttgatcacc agggcagagg ttttttgac  gccccagttc tctcctgaac cgattcctgc   6780
ggcccttgc  ctctttagtg acggggctac aggacgagga gcatattgcc tgtggaaaga   6840
ccaccttttg gactttcagg ccgttccggc tccagagtcc gcccaaaagg gagaactagc   6900
aggtctcttg gcgggcttag cagccgcccc gcctgaacct ttaaatatat gggtagattc   6960
caaataccta tactccttgc tcagaaccct agttctggga gcttggcttc aacctgaccc   7020
cgtaccctcc tatgccctcc tatacaaaag cctcctccga catccagcaa tctttgttgg   7080
tcatgtccgg agccactcct cagcatccca ccctattgct tccctgaaca attatgtaga   7140
tcaactgctc cccttagaaa ctccagagca atggcataag ctcacccact gcaactctcg   7200
ggccttgtct cgatggccga acccacgtat ttcggcctgg gatccccgtt ccccgctac   7260
gctatgtgaa acctgtcaaa agctcaatcc aactggaggt ggaaagatgc gaactattca   7320
gagagggtgg gccccgaatc atatttggca ggccgatata acccattata aatcaaaca   7380
gttcacctac gctttgcacg tgtttgtaga tacttactct ggagctactc atgcctcagc   7440
aaagcgaggg ctcaccactc aaatgaccat tgagggcctt ctggaggcca tagtacatct   7500
gggtcgtcca aaaaagctaa acactgacca aggcgcaaac tacacctcca aaacctttgt   7560
caggttttgc cagcagttcg gagtttccct ttctcatcac gttccctaca ccccacaag    7620
ttcagggttg gtagaacgga caaatggact gctcaaactt cttttgtcta aatatcacct   7680
agacgaaccc caccttccca tgactcaggc ccttttctcga gccctctgga ctcacaatca   7740
gattaacctc ctgccaattc taaagaccag atgggagtta caccattcac ccctacttgc   7800
tgtcatttca gagggcggag aaacacccaa gggctctgat aaactctttt tgtacaagct   7860
ccccgggcaa acaatcgtc  ggtggctagg accactcccg gccctagtcg aagcctcggg   7920
aggcgccctc ctggctacta accccccccgt gtgggttccc tggcgtttgc taaaagcctt   7980
caaatgccca agaacgacg  gtcccgaaga cgccacaac  cgatcatcag atgggtaagt   8040
ctcactctta ctctcctcgc tctctgtcag cccatccaga cttggagatg ctccctgtcc   8100
ctaggaaatc aacaatggat gacaacatat aaccaagagg caaaattttc catcgccatt   8160
gaccaaatac tagaggctca taatcaatcg cctttctgtc ccaggtctcc cagatacacc   8220
ttggactttg taaatggtta tcctaagatc tattggcccc cccacaagg  gcgacgccgg   8280
tttggagcca gggccatggt cacatatgat tgcgagcccc gatgcccta  tgtggggca    8340
gatcacttcg actgccccca ctgggacaat gcttcccagg ccgatcaagg gtccttttat   8400
```

```
gtcaatcatc agattttatt cctgcatctc aaacaatgtc atggaatttt cactctaacc    8460
tgggaaatat ggggatatga tcccctgatc acctttctt tacataaaat ccctgatccc     8520
cctcaacccg acttccctca gctgaacagt gactgggttc cctctgtcag gtcatgggcc    8580
ctgcttttaa atcaaacggc acgggccttc ccagactgtg ctatatgttg ggaaccttcc    8640
cctccctggg ctcccgaaat attagtatat aacaaaacca tctccaactc tggacccggt    8700
ctcgccctcc cggacgccca aatcttctgg gtcaacacgt ccttgtttaa caccacccaa    8760
ggatggcacc acccttccca gaggttgttg ttcaacgttt ctcaaggcaa cgccttatta    8820 ttaccccta tctccctggt taatctctct acggcttcct ccgcccctcc tacccgggtc     8880
agacgcagtc ctgccgcagc cctgaccttg gcctagccc tgtcagtggg gctcactgga     8940
attaatgtag ccgtgtccgc ccttagccat cagagactca cctccctgat ccacgttctg    9000
gagcaagatc agcaacgctt gatcacagca attaaccaga cccactataa tttgcttaat    9060
gtggcctctg tggtcgccca gaaccgacgg gggctagatt ggttgtacat ccggctgggt    9120
tttcaaagcc tatgtcccac gatcaatgaa ccttgctgtt tcctgcgcat tcaaaatgac    9180
tccattatcc gcctcggtga tctccagcct ctctcgcaaa gagtctctac agactggcaa    9240
tggccctgga attgggatct ggggctcacc gcctgggtgc gagaaaccat tcattctgtt    9300
ctaagcctat tcctattagc cctttttttg ctcttcttgg ccccctgcct gataaaatgc    9360
ttgacctctc gccttttaaa actcctccgg caggctcccc acttccctga atctccttc     9420 ccccctaaac ccgattctga ttatcaggcc ttgctaccat ccgcgccaga gatctactct    9480
cacctctccc ccaccaaacc cgattacatc aaccttcgac cctgcccttg acacccccat    9540
gtttcacgca ccctcaggct gtggtggggc actggcttag tggaatagtc agtgtaccat    9600
cacaagcctc ttcttgctgc cagcgccgag ttcgaacaca gccctaccct gagcctctct    9660
gagtgcatga ctgagtgtag cgcagagaga ttgtcgcttc tgcgtgtcac tcagtcattt    9720
tttatagccg attggggttc gcgccctccc gttgcctgtg acacggttaa gacctctctc    9780
acttctgctt caccatcccc ctgccagcgt tggtctagtg gaaagaacta acgctgacgg    9840
gggcgatttc ttgcagctgt gctaagcgag aggctctggt gctggggata agatgcggcc    9900
cctagcacca cagtctctgc gccttttggg ttcgaatctt ccccatgcag cttccgcttt    9960
ttacgccctg ttgcacaccc tttctagaga tacctgaaaa tctcagctcg caccccaagg   10020
aaggttgtgg ctcagaggtt aaaatagctc ggaccgcaac ctccctttct ttttattcca   10080
ccctcgcaag gccccgggtt ctagaccccc taacggaggt tcaaaatttc tctactagg    10140 gggtgctcag gtccaagtgt gcacaacatc tcttccaaaa ggtcctgatg aacatcttcc   10200
catgtaacaa gccccagcag agacattcca gccacatcca gcagcatttg gccgccttc    10260 tctaacagtg cccataaagt cccttctgtt tccacaacgg ctgcctctgc atcttctatt   10320
tccacctcgg caccgactcc cccgccgagc ccttcaagct cttcgggatc cattacctga   10380
taacgacaaa attatttctt gtcttttaag caagtgttgt tggttggggg ccccactctc   10440
tacatgcctg cccggccctg gttttgtcca atgatgtcac catcgatgcc tggtgccccc   10500
tctgcgggcc ccatgaacga ctccaattcg aaaggatcga caccacgctc acctgcgaga   10560
cccaccgtat cacctggacc gccgatggac gacctttcgg cctcaatgga acgttgttcc   10620
ctcgactgca tgtctccgag acccgccccc aagggcccg acgactctgg atcaactgcc   10680
cccttccggc cgttcgcgct cagcccggcc cggtttcact ttccccttc gagcagtccc   10740
```

-continued

```
ccttccagcc ctaccaatgc caattgccct cggcctctag cgatggttgc cccatcatcg    10800
ggcacggcct tcttccctgg aacagcttag taacgcatcc tgtcctcgga aaagtcctta    10860
cattaaatca aatggccaat ttttccttac tcccccectt cgataccctc cttgtggacc    10920
ccctccggct gtccgtcttt gccccggaca ctaggggagc catacgttat ctctccaccc    10980
ttttgacgct atgccagct  acttgtattc taccctagg  cgagcccttc tctcctaatg    11040
tccccatatg ccgctttccc cgggacacca atgaacctcc cctttcagaa ttcgagctgc    11100
cccttatcca aacgcccggc ctgtcttggt ctgtcccgc  gatcgaccta ttcctaaccg    11160 gtccccttc  cccatgcgac cggttacacg tgtggtccag tcctcaggcc ttacaacgct    11220
tcctccatga ccccacgctc acctggtcag aattggttgc tagcgggaaa ctaagacttg    11280 attcacccctt aaaattacag ctgttagaaa atgaatggct ctcccgcctt ttttgagggg   11340
gagtcatttg tatgaaagat catgccggcc taggcgccgc caccgcccg  taaaccagac    11400 agagacgtca gctgccagaa aagctggtga cggcagctgg tggctagaat ccccgtacct    11460
ccccaacttc cccttttcccg aaaaatccac accccgagct gctgacctca cctgctgata   11520
aaacaataaa atgccggccc tgtcgagtta gcggcaccag aagcgttctc ctcctgagac    11580
cctcgtgctc agctctcggt cctgagctct cttgctcccg agaccttctg gtcggctatc    11640
cggcagcggt caggtaaggc aaaccacggt ttggagggtg gttctcggct gagaccaccg    11700
cgagctctat ctccggtcct ctgaccgtct ccacgtggac tctctctctt gcctcctgac    11760
cccgcgctcc aagggcgtct ggcttgcacc cgcgcttgtt tcctgtctta ctttctgttt    11820
ctcgcggccc gcgctctctc cttcggcgcc ctctagcggc caggagagac cggcaaacag    11880
aaaagttgta cacacatttt acttacaatg tctaacgagg ttttaaaccg tcgactgtca    11940
acgtcaggag agcccttcga gcgttctttc tgcttcaaga cgcggggctg cacccctcgg    12000
acgccgccga actgaacgtc gccccgtccc tgcccacgtg atggagacct ccgcggggag    12060
ggtaggcgcc cgcggaatgc tgggactggt aggcgccggc tcctcccct  cctccccag    12120 gcgtcacccc cggctccact cccccagcag cccgcggctg ggcgggaggc tggaggcgtg    12180
gggagagcag ggacagaacc gcaaaggctc ccagcgttct cgcagttgcg ctgctctctg    12240
acctgaaggc agacatctct gcaacatatt ggagggccct ggaattggtg aatggccaga    12300
gaggcctggc gcagcccttg gggtcgcaga gtcggacacg actgaacgac agaactgaac    12360
tgaaccgagc ccttaaaaaa cctaaagctc agaggcttga ggaaccaatg gaaccaacgc    12420
agtgagcggc actagccaat gataatggca agcaccggtc aagcttgtat tc           12472
```

VACCINE AGAINST BOVINE LEUKEMIA VIRUS

RELATED APPLICATIONS

This application is a continuation of U.S. patent application Ser. No. 14/832,863, filed Aug. 21, 2015, now U.S. Pat. No. 10,029,006, which is a continuation of International Patent Application No. PCT/EP2014/053855, filed Feb. 27, 2014, which claims priority to U.S. Provisional Patent Application Ser. No. 61/769,971, filed Feb. 27, 2013, and European Patent Application No. 13156921.2, filed Feb. 27, 2013, the entire disclosures of which are hereby incorporated herein by reference in their entirety.

FIELD

The invention is in the medical field, especially in the veterinary field, and particularly pertains to vaccines, more particularly to vaccines against bovine leukemia virus. The invention more specifically relates to recombinant bovine leukemia viruses that have an attenuated phenotype, nucleic acids encoding such viruses, vectors comprising such nucleic acids, host cells comprising such nucleic acids or vectors, applications of these agents in medicine, particularly as vaccines, non-human animals vaccinated therewith, materials derived from such non-human animals, and downstream uses of such materials.

BACKGROUND

Although eradicated from Europe, bovine leukemia virus (BLV) is responsible for important economic losses worldwide. The great majority of BLV-infected animals are asymptomatic carriers of the virus. Approximately one-third of BLV-infected bovines develop a benign polyclonal proliferation of B cells called persistent lymphocytosis (PL), characterised by an increase in the absolute number of peripheral blood circulating B lymphocytes associated with an inversion of the B/T lymphocyte ratio. PL is usually stable for several years but can also progress to a tumour phase.

The most conspicuous clinical manifestation of BLV infection is the development of lymphoid tumours. Fatal lymphoma or lymphosarcoma (LS), characterised by mono- or oligo-clonal B cell expansion, occurs in less than 5-10% of infected animals, predominantly in adult cattle older than 4-5 years old. Local proliferation of B cells, called lymphosarcoma, can occur within different organs and tissues leading to a series of defects that are finally incompatible with the survival of the animal. In addition, transformed B cells can also induce the enlargement of lymph nodes and cause lymphoma. Besides an impact on survival, BLV infection also impairs the immune system leading to opportunistic infections.

Several attempts have been undertaken to develop vaccines against BLV, such as vaccines based on chemically inactivated BLV, vaccines based on lysates from, e.g., BLV-infected cells or BLV tumours, vaccines comprising BLV subunits, such as, e.g., the gp51 envelope glycoprotein. Other attempts used vaccinia virus as a vehicle and introduced BLV genes encoding, e.g., BLV envelope proteins, into its genome (i.e., recombinant vaccinia virus or RVV). Short peptides mimicking B and T cell epitopes of BLV proteins were also tested as immunogens. DNA vaccines comprising BLV genes, e.g., the env gene under the control of the cytomegalovirus promoter, were also developed. These 'traditional' vaccine candidates faced problems of inter alia efficacy (i.e., only an inadequately low fraction of vaccinated animals were protected), persistence (i.e., rapid decrease of immune protection in the vaccinated animals), cost (e.g., high cost of production of purified proteins), and/or safety (e.g., use of genetically modified hybrid viruses, such as RVV).

In an attempt to address the shortcomings of these earlier approaches, numerous attenuated BLV mutants were developed, e.g., by deleting genes dispensable for infectivity but required for efficient replication of the virus (Willems et al. 1993. J. Virol. 67: 4078-4085). Among these, an attenuated BLV provirus, pBLV6073, was obtained by introducing a mutation to an immunoreceptor tyrosine-based activation motif localised in the cytoplasmic tail of the transmembrane gp30 envelope glycoprotein (Willems et al. 1995. J. Virol. 69: 4137-4141). Another attenuated BLV provirus, pBLVDX, was constructed by deleting the R3 and G4 sequences (Willems et al. 1993. J. Virol. 67: 4078-4085). These BLV mutants (pBLV6073 and pBLVDX) were evaluated in Kerkhofs et al. 2000. J. Gen. Virol. 81: 957-963; Reichert et al. 2000. J. Gen. Virol. 81: 965-969; and Florins et al. 2007. J. Virol. 81: 10195-10200.

SUMMARY

The present inventors have conducted extensive studies of existing attenuated BLV proviruses, and have confirmed that these BLV proviruses, including inter alia pBLV6073 and pBLVDX, do remain pathogenic at a level that may prevent their widespread use as vaccines in veterinary practice. For example, pathogenicity was observed in one sheep among 20 that have been infected with the pBLVDX provirus after a latency period of 7 years. Also, as summarised in Table 1 of Florins et al. 2007 supra, pathogenicity was observed in one sheep among 8 that have been infected with the pBLVDX provirus after a latency period of 7.5 years. Furthermore, the pBLV6073 provirus induced leukemia in 1 out of 4 sheep after 83 months of latency (also see Table 1 of Florins et al. 2007 supra).

Hence, the previously existing attenuated BLV proviruses are still at least weakly pathogenic.

Moreover, protection achieved by previously existing attenuated BLV proviruses has been reported as not effective enough and comparatively short-term. For example, one of two cows vaccinated using the pBLVDX provirus and evaluated in Kerkhofs et al. 2000 supra became infected by wild-type BLV 12 months after challenge. One of three sheep vaccinated using the pBLVDX provirus and evaluated in Reichert et al. 2000 supra became infected by BLV from a naturally infected cow. Further importantly, as shown in the experimental section, cow #269 vaccinated using the pBLV6073 provirus and evaluated in Kerkhofs et al. 2000 supra also became infected by wild-type BLV 24 months after challenge.

The present invention addresses one or more of such problems observed by the inventors.

As corroborated by the experimental section, which illustrates certain representative embodiments of the invention, the inventors have realised that by combining specific mutations in a BLV (pro)virus, greatly improved vaccines may be obtained. Hence, the inventors accomplished recombinant BLV proviruses which were infectious, but which replicated at desirably low levels in target animals, such as specifically in cows.

At least some embodiments of the present recombinant BLV proviruses display one or more further advantages improving their use as vaccines. For example, such recombinant BLV proviruses may display one or more or preferably all of the following advantages: they elicit a strong anti-BLV immune response comparable to an immune response to wild-type BLV; they do not spread to uninfected sentinels maintained for prolonged periods of time in the same herd (i.e., satisfactory biosafety as a vaccine); they lead to production of antibodies that are transmitted to the newborn calves via the maternal colostrum, whereby the anti-viral passive immunity persists during several months in the calves; they do not transmit from cows to calves; they cause the vaccinated animals to resist a challenge by a wild type BLV provirus.

In particular, vaccines provided for by the recombinant BLV proviruses in accordance with aspects and embodiments of the present invention are highly effective, preferably achieving long-term protection (e.g., protection for at least 18 months or for at least 24 months or for at least 36 months or for at least 48 months post-vaccination) of virtually all tested animals (e.g., at least 90%, preferably at least 95%, such as 98%, or 99%, or even 100%), more preferably of cattle, from infection by wild-type BLV. Hence, in contrast to previously existing vaccines, the present recombinant BLV proviruses are effective in bovids, such as more particularly in cows, rendering the present vaccines particularly advantageous for controlling BLV infections in cattle.

Accordingly, in an aspect the invention provides a recombinant attenuated bovine leukemia virus (BLV) characterised in that the virus comprises:

(i) at least one mutation selected from the group consisting of:
  a mutation in the nucleic acid sequence encoding the most N-terminal YXXL signalling motif of the cytoplasmic domain of the transmembrane subunit (TM) of the envelope protein, said mutation disrupting the signal transduction activity of the motif, and
  a mutation in the X region of the BLV nucleic acid sequence, said mutation abolishing the production of at least one or preferably all microRNA encoded by said X region; and (ii) at least one mutation selected from the group consisting of:
  a mutation in G4 restricting the propagation of the BLV in vivo, and
  a mutation in R3 restricting the propagation of the BLV in vivo.

Further aspects of the invention provide:
The recombinant attenuated BLV encoded by the plasmid as deposited under the Budapest Treaty with the Belgian Coordinated Collections of Microorganisms BCCM/LMBP Collection under accession number LMBP 8166 on Feb. 5, 2013 (see Table 2B);
The recombinant attenuated BLV encoded by the plasmid as deposited under the Budapest Treaty with the Belgian Coordinated Collections of Microorganisms BCCM/LMBP Collection under accession number LMBP 8167 on Feb. 5, 2013 (see Table 2C);
The recombinant attenuated BLV encoded by the plasmid as deposited under the Budapest Treaty with the Belgian Coordinated Collections of Microorganisms BCCM/LMBP Collection under accession number LMBP 8713 on Oct. 25, 2013 (see Table 2D);
A recombinant nucleic acid encoding the recombinant attenuated BLV as disclosed herein;
A vector comprising the recombinant nucleic acid encoding the recombinant attenuated BLV as disclosed herein;
The plasmid as deposited under the Budapest Treaty with the Belgian Coordinated Collections of Microorganisms BCCM/LMBP Collection under accession number LMBP 8166 on Feb. 5, 2013 (see Table 2B);
The plasmid as deposited under the Budapest Treaty with the Belgian Coordinated Collections of Microorganisms BCCM/LMBP Collection under accession number LMBP 8167 on Feb. 5, 2013 (see Table 2C);
The plasmid as deposited under the Budapest Treaty with the Belgian Coordinated Collections of Microorganisms BCCM/LMBP Collection under accession number LMBP 8713 on Oct. 25, 2013 (see Table 2D);
A recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8166 on Feb. 5, 2013 (see Table 2B);
A recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8167 on Feb. 5, 2013 (see Table 2C);
A recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8713 on Oct. 25, 2013 (see Table 2D);
A vector comprising a recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8166 on Feb. 5, 2013 (see Table 2B);
A vector comprising a recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8167 on Feb. 5, 2013 (see Table 2C);
A vector comprising a recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8713 on Oct. 25, 2013 (see Table 2D);
A host cell comprising the recombinant attenuated BLV, the recombinant nucleic acid, the vector, or the plasmid as disclosed herein;

A pharmaceutical composition comprising the recombinant attenuated BLV, the recombinant nucleic acid, the vector, the plasmid, or the host cell as disclosed herein;

The recombinant attenuated BLV, the recombinant nucleic acid, the vector, the plasmid, or the host cell as disclosed herein for use in medicine;

The recombinant attenuated BLV, the recombinant nucleic acid, the vector, the plasmid, the host cell, or the pharmaceutical composition as disclosed herein, for use as a vaccine, in particular for use as a vaccine against a BLV-associated disease, more in particular for use as a prophylactic vaccine against a BLV-associated disease;

Use of the recombinant attenuated BLV, the recombinant nucleic acid, the vector, the plasmid, the host cell, or the pharmaceutical composition as disclosed herein, for the manufacture of a vaccine, in particular for the manufacture of a vaccine against a BLV-associated disease, more in particular for the manufacture of a prophylactic vaccine against a BLV-associated disease;

A method of vaccination of a subject in need of said vaccination, in particular vaccination against a BLV-associated disease, more in particular prophylactic vaccination against a BLV-associated disease, comprising the administration of an immunologically effective amount, more in particular of a prophylactically effective amount, of the recombinant attenuated BLV, the recombinant nucleic acid, the vector, the plasmid, the host cell, or the pharmaceutical composition as disclosed herein to the subject;

The recombinant attenuated BLV, the recombinant nucleic acid, the vector, the plasmid, the host cell, or the pharmaceutical composition as disclosed herein, for use in treatment of a BLV-associated disease, in particular for use in prevention (i.e., preventative treatment, prophylactic treatment, prophylaxis) of a BLV-associated disease;

Use of the recombinant attenuated BLV, the recombinant nucleic acid, the vector, the plasmid, the host cell, or the pharmaceutical composition as disclosed herein, for the manufacture of a medicament for treatment of a BLV-associated disease, in particular for the manufacture of a medicament for prevention of a BLV-associated disease;

A method of treating a BLV-associated disease in a subject in need of said treatment, in particular a method of preventing a BLV-associated disease in a subject in need of said prevention, comprising the administration of a therapeutically or prophylactically effective amount of the recombinant attenuated BLV, the recombinant nucleic acid, the vector, the plasmid, the host cell, or the pharmaceutical composition as disclosed herein to the subject;

A non-human animal, preferably a non-human mammal, more preferably a bovid, even more preferably a bovine, such as cattle, to which the recombinant attenuated BLV, the recombinant nucleic acid, the vector, the plasmid, the host cell, or the pharmaceutical composition as disclosed herein has been administered;

A method for obtaining a non-human animal material which comprises obtaining material from said non-human animal to which the recombinant attenuated BLV, the recombinant nucleic acid, the vector, the plasmid, the host cell, or the pharmaceutical composition as disclosed herein has been administered, and optionally further processing said material into a non-human animal-derived product;

Non-human animal-derived material or a non-human animal-derived product obtainable or directly obtained from said non-human animal, or obtainable or directly obtained by said method;

Said non-human animal-derived material or said non-human animal-derived product for use as a vaccine, in particular for use as a vaccine against a BLV-associated disease, more in particular for use as a prophylactic vaccine against a BLV-associated disease;

Use of said non-human animal-derived material or said non-human animal-derived product for the manufacture of a vaccine, in particular for the manufacture of a vaccine against a BLV-associated disease, more in particular for the manufacture of a prophylactic vaccine against a BLV-associated disease;

A method of vaccination of a subject in need of said vaccination, in particular vaccination against a BLV-associated disease, more in particular prophylactic vaccination against a BLV-associated disease, comprising the administration of an immunologically effective amount, more in particular of a prophylactically effective amount, of said non-human animal-derived material or said non-human animal-derived product to the subject;

Said non-human animal-derived material or said non-human animal-derived product for use in treatment of a BLV-associated disease, in particular for use in prevention of a BLV-associated disease;

Use of said non-human animal-derived material or said non-human animal-derived product for the manufacture of a medicament for treatment of a BLV-associated disease, in particular for the manufacture of a medicament for prevention of a BLV-associated disease;

A method of treating a BLV-associated disease in a subject in need of said treatment, in particular a method of preventing a BLV-associated disease in a subject in need of said prevention, comprising the administration of a therapeutically or prophylactically effective amount of said non-human animal-derived material or said non-human animal-derived product to the subject;

These and further aspects and preferred embodiments of the invention are described in the following sections and in the appended claims. The subject-matter of the appended claims is hereby specifically incorporated in this specification.

BRIEF DESCRIPTION OF DRAWINGS

FIGS. 1A-1J Schematic representations of BLV proviruses. (FIG. 1A) Wild-type BLV provirus is inserted into plasmid pSP64 (Promega Corp., Madison, Wis., USA; cat. no. P1241, Genbank acc. no. X65328.2), which comprises Ori and $amp^R$ for propagation and selection, respectively, in a bacterial host cell. Ori: origin of replication; $amp^R$: ampicillin resistance marker; LTR: long terminal repeats. Xba1 sites at positions 6614 and 6731 and Kpn1 site at position 2111 are restriction sites. (FIG. 1B) Structure of the wild-type BLV provirus. The provirus is flanked by two identical long terminal repeat sequences (LTRs) and comprises the open reading frames (ORFs) corresponding to gag, pol, env, R3, G4, Tax and Rex. The "mRNA" panel illustrates alternative splicing of the pre-mRNA precursors to yield the respective mRNA molecules, whereby exons are marked as straight horizontal lines, and introns intervening between the exons and spliced away from pre-mRNA precursors are noted as V-shaped horizontal lines. The white boxes indicate the location of protein-coding sequences present in the respective mRNA molecules, and of the region encoding BLV miRNAs. The "Proteins" panel illustrates the various proteins translated from the BLV mRNA molecules. (FIG. 1C) A schematic representation of the portion of wild-type BLV provirus genome including the env open reading frame (box "ENV"), the portion of the R3 open reading frame contained in exon 3 of R3 (box "R3"), the portion of the G4 open reading frame contained in exon 2 of G4 (box "G4"), and the portion of Tax and Rex open reading frames contained in exon 3 of Tax and Rex (boxes "Tax" and "Rex"). The exemplary BLV genomic positions indicated in the drawing are based on numbering of the BLV sequence as adopted by Rice et al. 1987 (Sequence analysis of the Bovine Leukemia Virus Genome. In A. Burney and M. Mammerickx (ed.), Enzootic bovine leukosis and bovine leukemia virus. Martinus Nijhof, Leiden, The Netherlands, pp. 115-144). In particular, the drawing indicates from 5' to 3': the codon at positions 6073-6075 encoding the most N-terminal YXXL signalling motif of the cytoplasmic domain of the transmembrane subunit (TM) of the envelope protein; the env stop codon (TGA) at positions 6160-6162; the microRNA region (represented as iii) interposed between env stop codon and exon 3 of R3; the sequence AAAG/GTCC (positions 6809-6816) defining the intron 2-exon 3 boundary of R3 and the first nucleotide of exon 3 of R3 at position 6813; the sequence TTCC/AGCC (positions 6857-6864) defining the intron 1-exon 2 boundary of G4 and the first nucleotide of exon 2 of G4 at position 6861; the R3 stop codon (TAA) at positions 6894-6896; the sequence TAAG/CAAG (positions 7038-7045) defining the intron 2-exon 3 boundary of Tax/Rex and the first nucleotide of exon 3 of Tax/Rex at position 7042; and the G4 stop codon (TGA) at positions 7103-7105. (FIG. 1D) An exemplary BLV genomic sequence, from position 5790 to position 7409, as reproduced from Rice et al. 1987 supra (SEQ ID NO: 16). The TAT codon at positions 6073-6075 is underlined. (FIG. 1E) Another representation of a schematic structure of wild-type BLV provirus. (FIG. 1F) Schematic structure of the 'BLVDX' provirus. The BLVDX provirus comprises deletions in the R3 and G4 ORFs. (FIG. 1G) Schematic structure of the 'BLV6073' provirus. The BLV6073 provirus comprises a substitution at position 6073 in an immunoreceptor tyrosine-based activation motif (ITAM) located in the transmembrane protein gp30 of the envelope. (FIG. 1H) Schematic structure of the 'BLV6073DX' provirus. The BLV6073DX provirus comprises both the mutation at position 6073 of BLV6073 and the deletions in the R3 and G4 ORFs of BLVDX. (FIG. 1I) Schematic structure of the 'BLV6073GPDX' provirus. The BLV6073DX provirus comprises the mutation at position 6073 of BLV6073 and a deletion in the miRNA, R3 and G4 ORFs. (FIG. 1J) A schematic representation of the specific mutations present in BLV6073DX shown on the schematic representation of a wild-type BLV provirus genome as shown in FIG. 1C. The BLV genomic positions are based on numbering of the BLV sequence as adopted by Rice et al. 1987 supra. The BLV6073DX provirus carries a substitution of a T nucleotide at position 6073 of the BLV nucleic acid sequence with a G nucleotide and further comprises a double oligonucleotide segment composed of two hybridised oligonucleotides with the sequences 5'-CTAGAAAGCTTG-3' (SEQ ID NO: 1) and 5'-GATCCAAGCTTT-3' (SEQ ID NO: 2), respectively, replacing the nucleic acid segment between XbaI site at position 6614 and BamHI site at position 6997 of the BLV nucleic acid sequence.

Figure 2A:
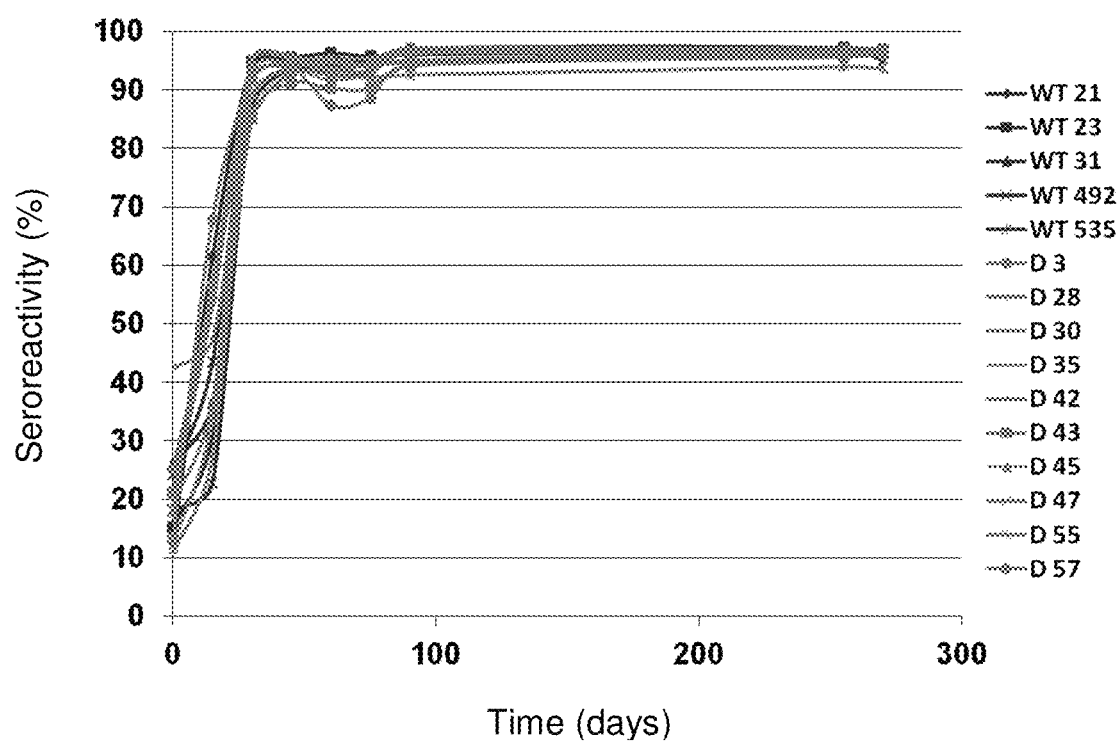
Figure 2B:
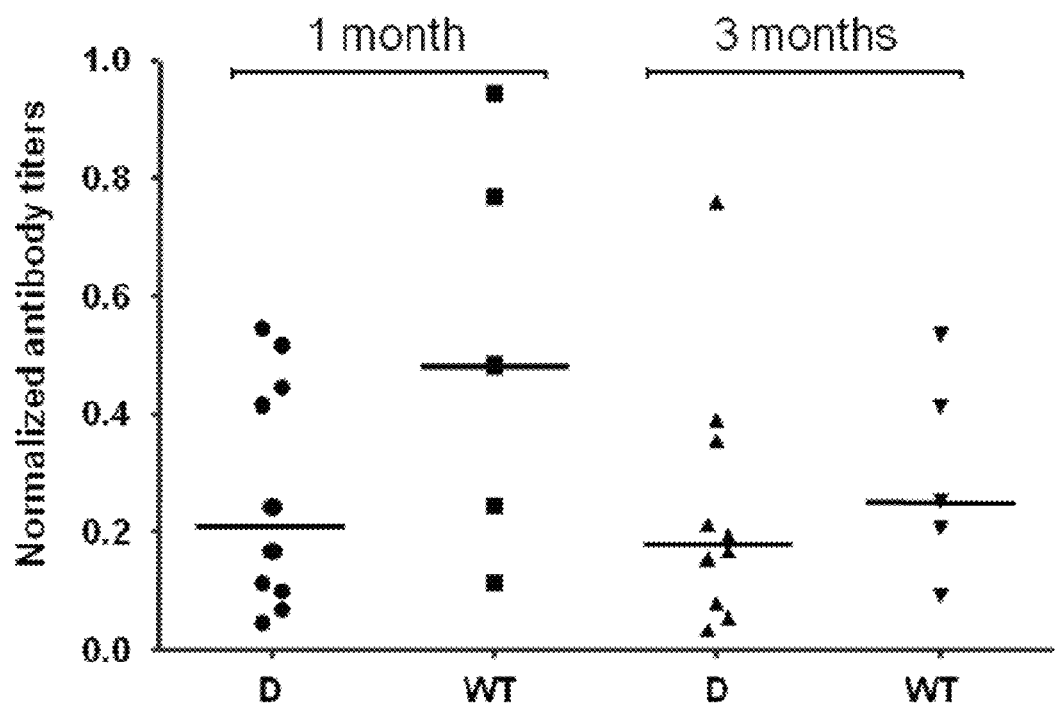

FIGS. 2A-2B Infectivity of and immune response against recombinant BLV6073DX provirus and wild-type BLV pro-virus. Cows were infected with recombinant BLV6073DX provirus (D) or wild-type provirus (WT) and kept in a herd of 74-82 animals among which 15-30% were naturally infected with wild-type BLV Argentinean strain. Kinetics, expressed as percentage seroreactivity (compared to a negative control) in function of time (FIG. 2A), and antibody titres expressed as normalized antibody titres (FIG. 2B) of the antiviral antibody response were determined by a competitive ELISA test (ELISA Bovine Leukosis Serum blocking test, Institut Pourquier). The test measures optical density (OD) at 450 nm. The antiviral antibody response is expressed as percentage seroreactivity compared to a negative control and is calculated as the ratio of the OD of the test sample to the OD of the negative control (100% means that the ratio of the sample OD/negative control OD is 1). A sample is considered to be positive providing that this ratio is higher than a threshold arbitrarily set to 40%. Antibody titres are expressed as the inverted dilution of the serum that yields 50% of the maximal OD and normalized antibody titres are calculated as the ratio of the inverted dilution that yields 50% of the maximal OD of the test sample to the inverted dilution that yields 50% of the maximal OD of an arbitrarily chosen positive control.

Figure 3:
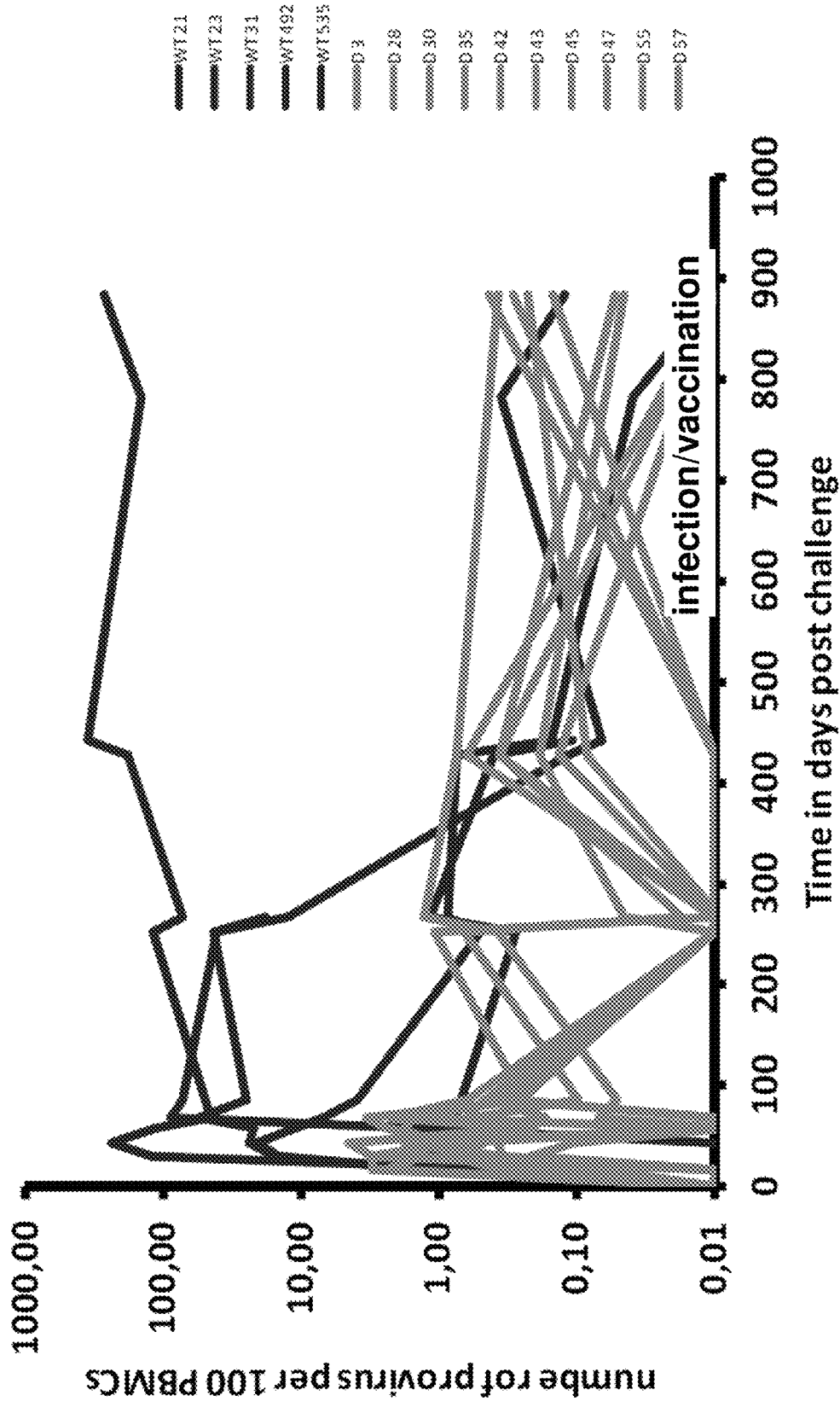

FIG. 3 Replication level of recombinant BLV6073DX vs. wild type provirus. Cows were infected with recombinant BLV6073DX provirus (D) or wild-type provirus (WT) and kept in a herd of 74-82 animals among which 15-30% were naturally infected with wild-type BLV Argentinean strain. Proviral loads were determined by measuring the proviral copies in peripheral blood mononuclear cells (PBMC). Proviral load is expressed as number of proviral copies per 100 PBMCs.

Figure 4A:
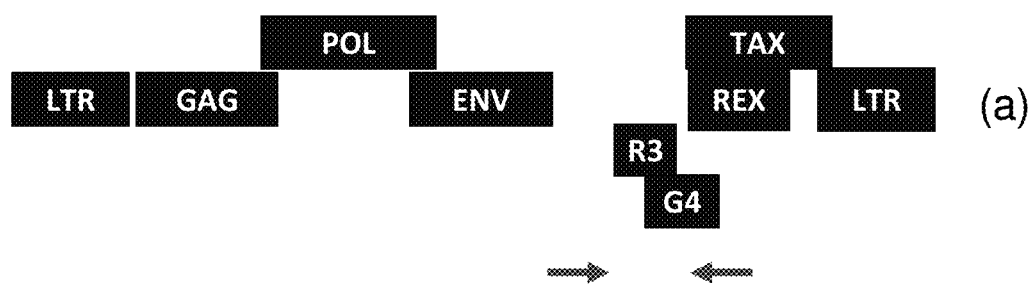
Figure 4B:
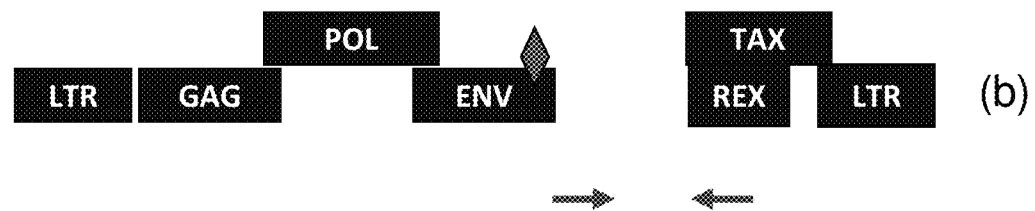

FIGS. 4A-4B Schematic representation of PCR amplification used to identify vaccinated animals. (FIG. 4A) Primers that flank the deletion in the R3 and G4 ORFs of BLV6073DX provirus were designed. (FIG. 4B) Depending on the presence of the deletion, different amplicons can be observed after gel electrophoresis of the PCR amplification products. The presence of the small and large amplicon identifies vaccinated (b) and WT-infected (a) animals, respectively. Detection of both amplicons reveals that a vaccinated animal has become infected with a wild-type BLV (c). The absence of amplicons indicates that the animal was neither vaccinated nor infected with a wild-type BLV (d).

Figure 5:
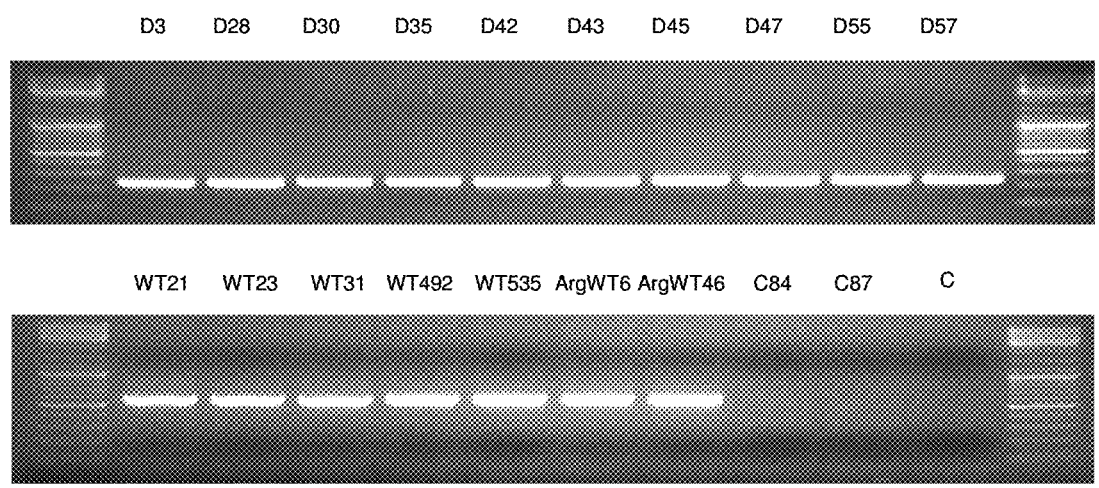

FIG. 5 Effect of vaccination with recombinant BLV6073DX provirus on infection by wild-type BLV in herd conditions. Cows were infected with recombinant BLV6073DX provirus (D) or wild-type provirus (WT) and kept in a herd of 74-82 animals among which 15-30% were naturally infected with wild-type BLV Argentinean strain (ArgWT). Calves (C84 and C87) were born from cows infected with recombinant BLV6073DX provirus. PCR amplification in the absence of DNA (water) was performed as a control (C). PCR amplification was performed using primers flanking the deletion in the R3 and G4 ORFs of BLV6073DX provirus and the amplicons are shown.

Figure 6A:
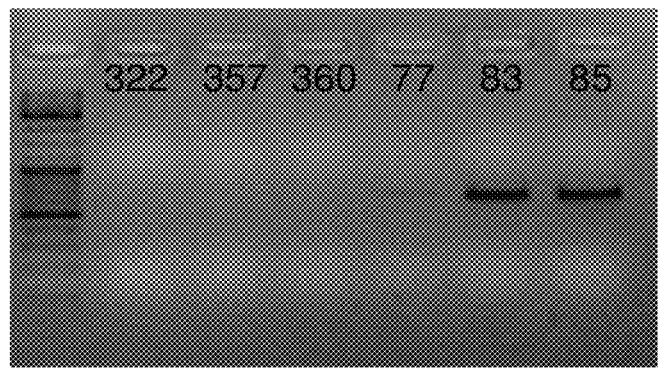
Figure 6B:
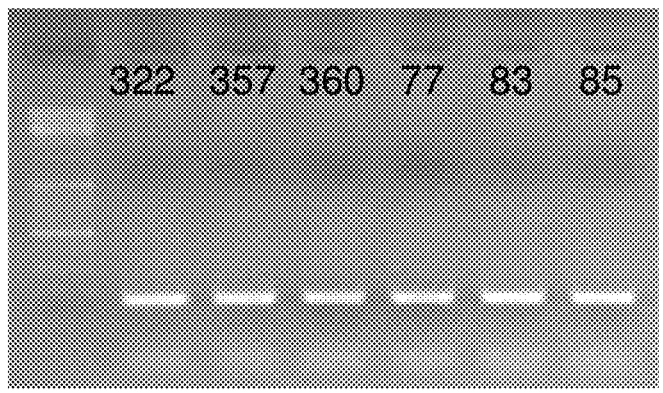

FIGS. 6A-6B Effect of vaccination with recombinant BLV6073DX provirus on challenge by wild-type BLV. Animals infected with recombinant BLV6073DX provirus (#322, #357 and #360) or uninfected animals (#77, #83 and #85) were challenged with wild-type BLV provirus by injection of HeLa cells transfected with wild-type BLV provirus plasmid. Infection with wild-type BLV was assessed by nested PCR using BLV primers (FIG. 6A). Actin primers were used as control (FIG. 6B). Amplicons are shown.

Figure 7A:
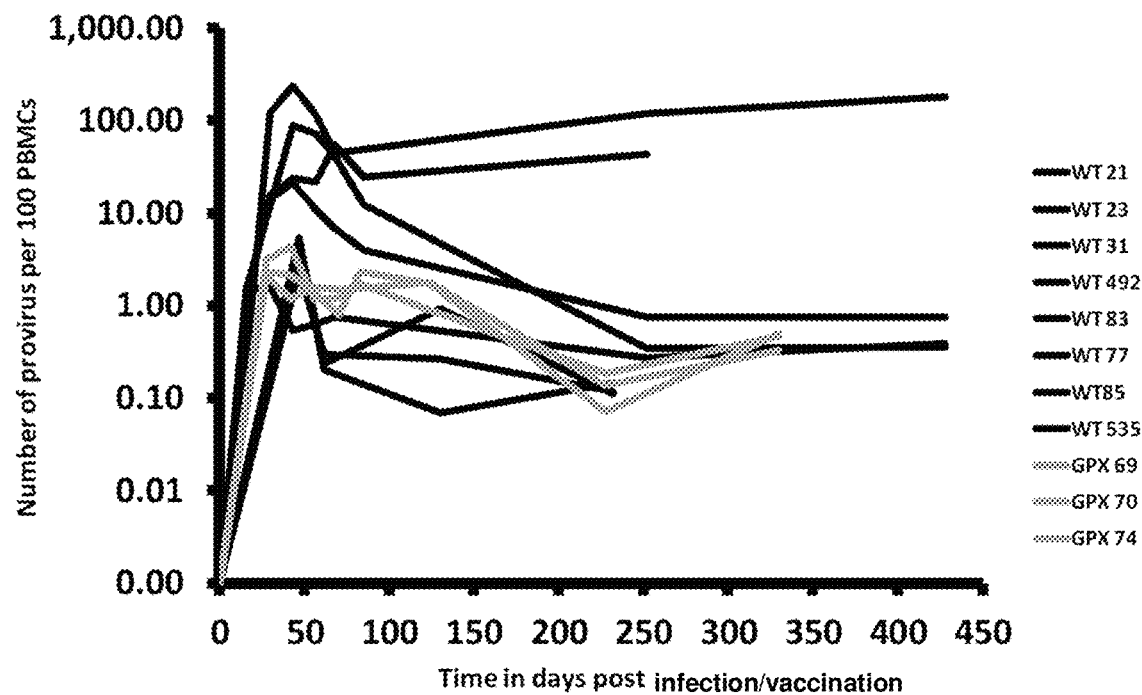
Figure 7B:
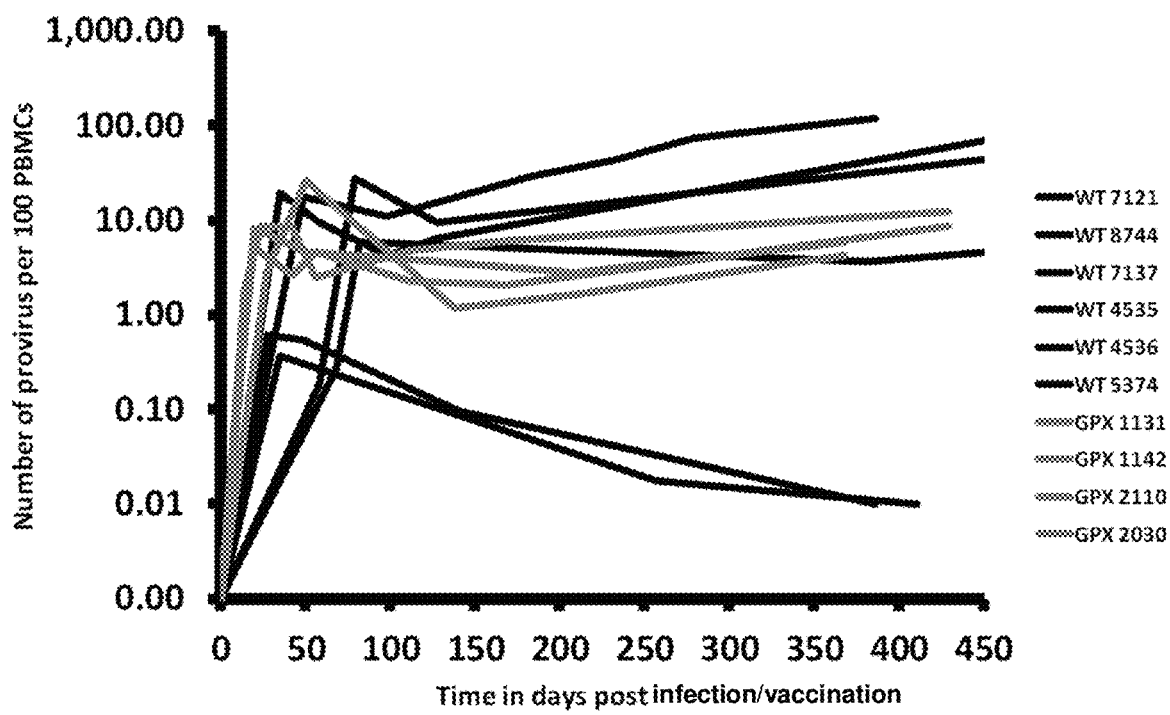

FIGS. 7A-7B Infectivity of recombinant BLVGPX provirus in vivo. Cows (FIG. 7A) or sheep (FIG. 7B) were infected with recombinant BLVGPX provirus (GPX) or wild-type provirus (WT). Proviral loads were determined by measuring the proviral copies in peripheral blood mononuclear cells (PBMC). Proviral load is expressed as number of proviral copies per 100 PBMCs.

FIGS. 8A-8B Wild-type BLV infection in cow #269 inoculated by BLV6073. Schematic representation of the position of primer pairs 6073S+7049R (1), 5719S+7049R (2), and 5719S+7000R (3) in wild-type ("WT") and pBLV6073 ("Mutant 6073") sequences (FIG. 8A). Amplification products obtained by PCR using the primer pairs 6073S+7049R (lane 1), 5719S+7049R (lane 2), and 5719S+7000R (lane 3) on nucleic acids isolated from the blood of pBLV6073-vaccinated cow #269 (Kerkhofs et al. 2000 supra) at 18 months (left panel) and 24 months (right panel) after challenge with wild-type BLV (FIG. 8B).

Figure 9:
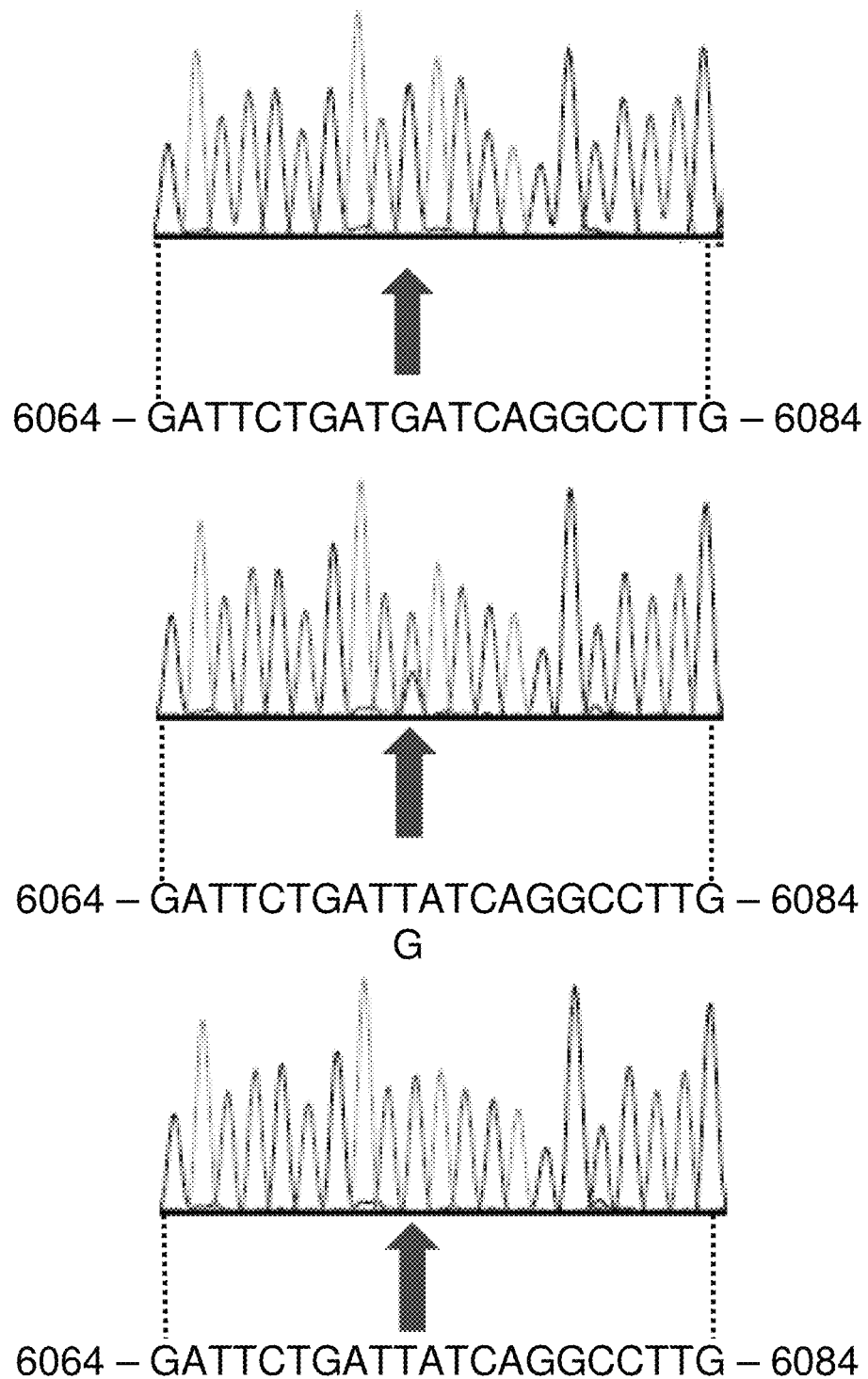

FIG. 9 Wild-type BLV infection in cow #269 inoculated by BLV6073. Sequence reads of positions 6064 through 6084 of the BLV sequence on nucleic acids isolated from the blood of pBLV6073-vaccinated cow #269 (Kerkhofs et al. 2000 supra) at 18 months (top panel) and 24 months (middle panel) after challenge with wild-type BLV, and on control env gene from a wild-type BLV virus (bottom panel). Arrows indicate the nucleotide at nucleotide position 6073.

Figure 10:
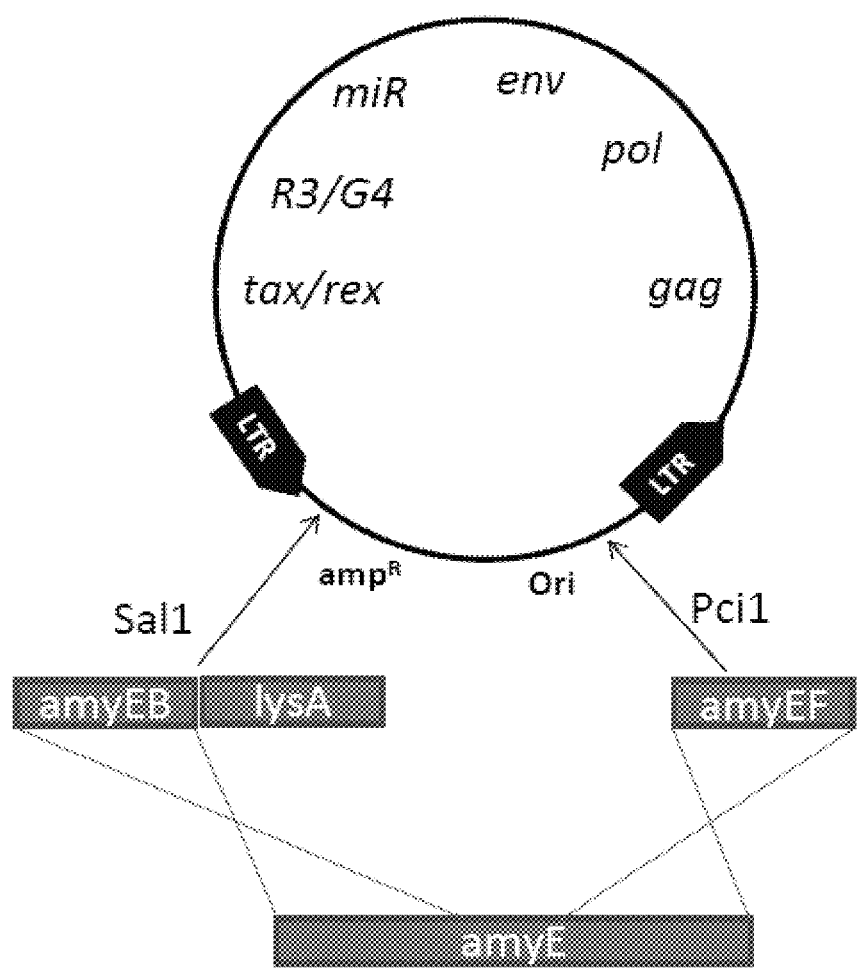

FIG. 10 Schematic representation of the introduction of pBLV6073GPDX into *Bacillus subtilis*. amyEB, lysA and amyEF sequences were introduced into pBLV6073GPDX and the resulting construct recombined into amyE locus of *Bacillus subtilis* strain 168 (amyE+ lysA−), resulting in amyE− lysA+ phenotype.

FIGS. 11A-11H Complete genomic sequence of BLV 344 provirus from pBLV344H (SEQ ID NO: 39). Positions 3159-11879 in the sequence shown in FIGS. 11A-11H correspond to the sequence of the provirus (including here at the 5' end 211 nucleotides of the U3 region 5' of the transcriptional start site). The TAT codon at positions 6073-6075 of the provirus (positions 9442-9444 in the sequence shown in FIGS. 11A-11H) is underlined.

DESCRIPTION OF EMBODIMENTS

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

As noted, the inventors have realised that by combining certain mutations in the BLV genome an attenuated BLV may be obtained useful for the production of greatly improved vaccines. These attenuated BLV are infectious, thus facilitating their introduction into the to-be-vaccinated subjects, but replicate at desirably low levels in the vaccinated subjects.

Accordingly, in an aspect the invention provides a recombinant attenuated bovine leukemia virus (BLV) characterised in that the virus comprises:
- at least one mutation selected from the group consisting of:
  - a mutation in the nucleic acid sequence encoding the most N-terminal YXXL signalling motif of the cytoplasmic domain of the transmembrane subunit (TM) of the envelope protein, said mutation disrupting the signal transduction activity of the motif, and
  - a mutation in the X region of the BLV nucleic acid sequence, said mutation abolishing the production of at least one or preferably all microRNA encoded by said X region; and
- at least one mutation selected from the group consisting of:
  - a mutation in G4 restricting the propagation of the BLV in vivo, and
  - a mutation in R3 restricting the propagation of the BLV in vivo.

Unexpectedly, the combinations of the mutations in the resulting recombinant BLV, rather than being deleterious for the recombinant BLV (e.g., completely destroying its infectivity in animals, particularly in cattle), preserves satisfactory levels of infectivity of the recombinant BLV and reduces or eliminates its pathogenicity, thereby achieving greatly improved attenuated vaccines in animals, particularly in cattle.

In certain preferred embodiments, the recombinant attenuated BLV may comprise:
- at least one mutation selected from the group consisting of:
  - the mutation in the nucleic acid sequence encoding the most N-terminal YXXL signalling motif of the cytoplasmic domain of the transmembrane subunit (TM) of the envelope protein, said mutation disrupting the signal transduction activity of the motif, and
  - the mutation in the X region of the BLV nucleic acid sequence, said mutation abolishing the production of at least one or preferably all microRNA encoded by said X region; and
- both of the following mutations:
  - the mutation in G4 restricting the propagation of the BLV in vivo, and
  - the mutation in R3 restricting the propagation of the BLV in vivo.

In certain further preferred embodiments, the recombinant attenuated BLV may comprise:
- both of the following mutations:
  - the mutation in the nucleic acid sequence encoding the most N-terminal YXXL signalling motif of the cytoplasmic domain of the transmembrane subunit (TM) of the envelope protein, said mutation disrupting the signal transduction activity of the motif, and
  - the mutation in the X region of the BLV nucleic acid sequence, said mutation abolishing the production of at least one or preferably all microRNA encoded by said X region; and
- at least one mutation selected from the group consisting of:
  - the mutation in G4 restricting the propagation of the BLV in vivo, and
  - the mutation in R3 restricting the propagation of the BLV in vivo.

In certain particularly preferred embodiments, the recombinant attenuated BLV may comprise: the mutation in the nucleic acid sequence encoding the most N-terminal YXXL signalling motif of the cytoplasmic domain of the transmembrane subunit (TM) of the envelope protein, said mutation disrupting the signal transduction activity of the motif, the mutation in G4 restricting the propagation of the BLV in vivo, and the mutation in R3 restricting the propagation of the BLV in vivo. Unexpectedly, whereas protection achieved by the previously existing attenuated BLV proviruses pBLVDX and pBLV6073 has been reported as not effective enough and comparatively short-term, the recombinant attenuated BLV in accordance with these embodiments, combining mutations in the N-terminal YXXL signalling motif of the cytoplasmic domain of TM of the envelope protein, in G4 and in R3, such as for example BLV6073DX described elsewhere in this specification, are highly effective and provide for long-term protection. Surprisingly, the combination of the mutations, rather than being deleterious for the recombinant BLV (e.g., completely destroying its infectivity, such as the infectivity of BLV6073DX in animals, particularly in cattle), preserves satisfactory levels of infectivity of the recombinant BLV and reduces or eliminates its pathogenicity, thereby achieving greatly improved attenuated vaccines in animals, particularly in cattle.

In certain further particularly preferred embodiments, the recombinant attenuated BLV may comprise: the mutation in the X region of the BLV nucleic acid sequence, said mutation abolishing the production of at least one or preferably all microRNA encoded by said X region, the mutation in G4 restricting the propagation of the BLV in vivo, and the mutation in R3 restricting the propagation of the BLV in vivo.

In certain further preferred embodiments, the recombinant attenuated BLV may comprise: the mutation in the nucleic acid sequence encoding the most N-terminal YXXL signalling motif of the cytoplasmic domain of the transmembrane subunit (TM) of the envelope protein, said mutation disrupting the signal transduction activity of the motif, the mutation in the X region of the BLV nucleic acid sequence, said mutation abolishing the production of at least one or preferably all microRNA encoded by said X region, and the mutation in G4 restricting the propagation of the BLV in vivo.

In certain further preferred embodiments, the recombinant attenuated BLV may comprise: the mutation in the nucleic acid sequence encoding the most N-terminal YXXL signalling motif of the cytoplasmic domain of the transmembrane subunit (TM) of the envelope protein, said mutation disrupting the signal transduction activity of the motif, the mutation in the X region of the BLV nucleic acid sequence, said mutation abolishing the production of at least one or preferably all microRNA encoded by said X region, and the mutation in R3 restricting the propagation of the BLV in vivo.

In yet further particularly preferred embodiments, the recombinant attenuated BLV may comprise: the mutation in the nucleic acid sequence encoding the most N-terminal YXXL signalling motif of the cytoplasmic domain of the transmembrane subunit (TM) of the envelope protein, said mutation disrupting the signal transduction activity of the motif, the mutation in the X region of the BLV nucleic acid sequence, said mutation abolishing the production of at least one or preferably all microRNA encoded by said X region, the mutation in G4 restricting the propagation of the BLV in vivo, and the mutation in R3 restricting the propagation of the BLV in vivo.

In various embodiments, the recombinant attenuated BLV may comprise combinations of mutations as individualised in Table 1.

TABLE 1

Design of certain embodiments of recombinant
attenuated BLV proviruses as taught herein.

| BLV provirus embodiment #* | Mutations present |
|---|---|
| 1 | mut TM + mut R3 |
| 2 | mut TM + mut G4 |
| 3 | mut TM + mut R3 + mut G4 |
| 4 | mut microRNA + mut R3 |
| 5 | mut microRNA + mut G4 |
| 6 | mut microRNA + mut R3 + mut G4 |
| 7 | mut TM + mut microRNA + mut R3 |
| 8 | mut TM + mut microRNA + mut G4 |
| 9 | mut TM + mut microRNA + mut R3 + mut G4 |

*consecutive numbering solely for the purposes of Table 1.

For the purposes of Table 1, "mut TM" denotes the mutation in the nucleic acid sequence encoding the most N-terminal YXXL signalling motif of the cytoplasmic domain of the transmembrane subunit (TM) of the envelope protein, said mutation disrupting the signal transduction activity of the motif; "mut G4" denotes the mutation in G4 restricting the propagation of the BLV in vivo; "mut R3" denotes the mutation in R3 restricting the propagation of the BLV in vivo; and "mut microRNA" denotes the mutation in the X region of the BLV nucleic acid sequence, said mutation abolishing the production of at least one or preferably all microRNA encoded by said X region.

Preferred embodiments of those individualised in Table 1 may be embodiments #3 and #6 to #9, more preferred #3, #6 and #9, even more preferred #3 and #9.

The term "bovine leukemia virus" or "BLV" refers to a naturally occurring oncogenic, B-lymphotropic retrovirus that mainly infects cattle, preferably domestic cattle. It is a member of the Oncovirinae subfamily and belongs to the Deltaretrovirus genus, which also includes the human T-cell leukemia virus types 1 and 2 (HTLV-1 and-2). The term encompasses BLV of any and all geographical origins, such as without limitation BLV originating from (e.g., isolated or isolatable from cattle in) Argentina, Belgium, Brazil, Costa Rica, France, Iran, Japan, Russia, Ukraine, or USA. The term further encompasses any and all variants, clones, strains, isolates and genotypes of BLV. A useful but non-limiting overview of previously identified BLV isolates and genotypes, which may be useful in performing the present invention, is found inter alia in Rodriguez et al. 2009 (J Gen Virol. 90: 2788-97) and references cited therein.

Upon infecting a host cell, preferably a B lymphocyte, the viral +mRNA genome is reverse transcribed into DNA and integrated as a provirus into the genome of the BLV-infected host cell. The provirus can persist integrated into the host cell genome, thereby inducing a persistent or latent infection with diverse outcomes, ranging from asymptomatic to persistent lymphosis, lymphosarcoma and lymphoma. BLV can be transmitted through the transfer of BLV-infected cells (such as, e.g., B-lymphocytes and monocytes/macrophages) present in, e.g., blood or milk. Routes of transmission may include cattle management procedures involving transfer of infected blood such as dehorning, ear tattooing, rectal palpation, or the use of infected needles.

A non-limiting example of BLV is BLV clone 344 isolated as a provirus from a BLV-induced tumour (Van den Broeke et al. 1988, Proc. Natl. Acad. Sci. USA 85: 9263-9267). BLV 344 provirus is available inter alia cloned in the pSP64 plasmid, thereby yielding the plasmid pBLV344H as described in Willems et al. 1993 (J. Virol. 67: 4078-4085). The plasmid pBLV344H has been deposited under the Budapest Treaty with the Belgian Coordinated Collections of Microorganisms BCCM/LMBP Collection under accession number LMBP 8165 on Feb. 5, 2013 (see Table 2A). The complete sequence of the BVL 344 provirus as sequenced from plasmid pBLV344H is shown in FIGS. 11A-11H. Another non-limiting example of BLV is as described by Sagata et al. 1985 (Proc. Natl. Acad. Sci. USA 82: 677-681). A further non-limiting example of BLV is as sequenced by Rice et al. 1987 (Sequence analysis of the Bovine Leukemia Virus Genome. In A. Burney and M. Mammerickx (ed.), Enzootic bovine leukosis and bovine leukemia virus. Martinus Nijhof, Leiden, The Netherlands, pp. 115-144). Additional non-limiting example of BLV includes the BLV deposited under American Type Culture Collection ATCC® (Culture Collection Corporation) accession no. VR-1315. In certain embodiments, the BLV for carrying out the aspects and embodiments of the present invention may be the BLV isolate 344 as described by Van den Broeke et al. 1988 supra. As mentioned, the BLV 344 provirus has been deposited in plasmid pBLV344H under the Budapest Treaty with the Belgian Coordinated Collections of Microorganisms BCCM/LMBP Collection under accession number LMBP 8165 on Feb. 5, 2013 (see Table 2A).

In certain other embodiments, the BLV for performing the present invention may be the BLV isolate LS2 (complete proviral genome sequence annotated under GenBank acc. no. HE967302.1); BLV isolate LS3 (complete proviral genome sequence annotated under GenBank acc. no. HE967303.1); BLV isolate LS1 (complete proviral genome sequence annotated under GenBank acc. no. HE967301.1); BLV isolate of which the complete genome sequence is annotated under GenBank acc. no. NC_001414.1; BLV isolate of which the gag and pol genes sequence is annotated under GenBank acc. no. M10987.1; BLV isolate of which the env gene and post-env region sequence is annotated under GenBank acc. no. K02251.1; BLV isolate of which the complete genome sequence is annotated under GenBank acc. no. AF033818.1; BLV strain Arg41 (complete genome sequence annotated under GenBank acc. no. FJ914764.1); BLV isolate of which the complete genome sequence is annotated under GenBank acc. no. AF257515.1; BLV isolate of which the complete genome sequence is annotated under GenBank acc. no. K02120.1; BLV isolate of which the complete genome sequence is annotated under GenBank acc. no. D00647.1; or BLV isolate pBLV913 (complete proviral genome sequence annotated under GenBank acc. no. EF600696.1).

The term "recombinant" is generally used to indicate that the material (e.g., a virus, a nucleic acid, a genetic construct or a protein) has been altered by technical means (i.e., non-naturally) through human intervention. The term "recombinant nucleic acid" can commonly refer nucleic acids comprised of segments joined together using recombinant DNA technology. As used herein, the term may preferably denote material (e.g., a virus, a nucleic acid, a genetic construct or a protein) that has been altered by technical means of mutagenesis.

The term "attenuated" is well-known in the field of vaccination and when used in combination with a virus, preferably a bovine leukemia virus, denotes a virus variant or mutant which exhibits a substantially lower degree of virulence compared to a wild-type virus, preferably a virus variant or mutant exhibiting reduced propagation in the host (i.e., in vivo), e.g., due to slower growth rate and/or a reduced level of replication compared to a wild-type virus.

Propagation of an attenuated virus in the host (i.e., in vivo) may be at least about 10 fold, e.g., at least about 25 fold, or at least about 50 fold, or at least about 75 fold, preferably at least about 100 fold, less than that of a wild-type virus.

Suitable methods for measuring the propagation of a virus, in particular attenuated BLV or wild-type BLV, in the host include without limitation determining the proviral loads in the challenged host. For example, the number of BLV proviral copies may be determined using a suitable methodology, e.g., quantitative PCR, per a given number, e.g., 100, of peripheral blood mononuclear cells at a given time or times, i.e., in function of time, following the challenge of the host, in particular cattle such as a cow, with the virus. See Example 3 for a specific, non-limiting application of this approach.

Typically, such attenuated virus will not induce symptoms of viral infection or will induce only mild symptoms upon infecting, preferably through vaccination, a subject, but severe symptoms of viral infection do not typically occur in the infected, preferably vaccinated, subject.

The terms "mutation" and "mutagenesis" and the like generally refer to changes in nucleic acid sequences. Such changes may naturally occur, e.g., due to errors that occur during nucleic acid replication, mitosis or meiosis, or due to insertion of transposons or viral sequences. They may also be artificially (i.e., non-naturally) introduced by technical means through human intervention, e.g., by chemicals, irradiation, or recombinant DNA technology. As used herein, the terms preferably refer to such 'artificial' mutations.

Mutations in general may either have no effect (e.g., silent mutations) or they may have an effect on a given transcription product and/or translation product, e.g., they may result in the production of no transcription and/or translation product, or may result in the production of a transcription and/or translation product that is substantially not functioning or not functioning properly (i.e., not as the wild-type product).

In the present specification, the term "mutation" may particularly refer to a sequence change in the nucleic acid of a BLV (i.e., mutated BLV, BLV mutant) compared to the nucleic acid of a BLV that has not been so-mutated, such as, preferably, compared to the nucleic acid of a wild-type BLV. "Wild-type" BLV as used herein may suitably refer to naturally occurring, pathogenic BLV found in or isolated from BLV-infected hosts. The term also includes wild-type BLV proviruses, isolated forms thereof and genetic constructs containing such.

Optionally, a BLV carrying the mutation(s) as taught by the present invention may also comprise one or more other mutations not specified herein, e.g., one or more other mutations vis-à-vis a wild-type BLV. Such one or more other mutations may be in any one of the BLV genes, for example, in any one or more of the gag, pol, env, microRNA, R3, G4, Tax and Rex genes. Preferably such one or more other mutations do not interfere with replication of the BLV, in particular such one or more other mutations do not restrict the propagation of the BLV in vivo.

Mutations affecting a given BLV polypeptide (e.g., the level of production and/or the amino acid sequence of the polypeptide) may reside in nucleic acid sequence(s) comprised in the open reading frame (ORF) coding for said polypeptide, and/or such mutations may reside in nucleic acid sequence(s) comprised in the non-coding portions (untranslated regions) of the messenger RNA (mRNA) encoding said polypeptide, and/or such mutations may reside in nucleic acid sequence(s) comprised in precursor RNA (pre-mRNA) encoding said polypeptide, but removed (spliced out) from the mature mRNA encoding said polypeptide.

An "open reading frame" or "ORF" as used herein refers to a succession of coding nucleotide triplets (codons) starting with a translation initiation codon and closing with a translation termination codon known per se, and not containing any internal in-frame translation termination codon, and potentially capable of encoding a protein or polypeptide. Reference to the "level" of a BLV polypeptide encompasses the quantity and/or the availability (e.g., availability for performing its biological function) of the BLV polypeptide, e.g., in a cell, tissue, organ or an organism.

By means of an example and without limitation, a mutation in G4 as intended herein, which may also be denoted as a mutation in G4 gene, which affects the G4 polypeptide (e.g., the level of production and/or the amino acid sequence of the G4 polypeptide) may reside in nucleic acid sequence(s) comprised in the ORF coding for the G4 polypeptide, and/or such mutation may reside in nucleic acid sequence(s) comprised in the non-coding portions of the mRNA encoding the G4 polypeptide, and/or such mutation may reside in nucleic acid sequence(s) comprised in pre-mRNA encoding the G4 polypeptide, but removed (spliced out) from the mature mRNA encoding the G4 polypeptide. Hence, "a mutation in G4" that may be denoted as "a mutation in G4 gene" may also be denoted as a mutation in the nucleic acid sequence encoding G4, in the sense that the mutation may be the nucleic acid sequence encoding G4 pre-mRNA, G4 mRNA and/or G4 ORF.

Similarly, by means of an example and without limitation, a mutation in R3 as intended herein, which may also be denoted as a mutation in R3 gene, which affects the R3 polypeptide (e.g., the level of production and/or the amino acid sequence of the R3 polypeptide) may reside in nucleic acid sequence(s) comprised in the ORF coding for the R3 polypeptide, and/or such mutation may reside in nucleic acid sequence(s) comprised in the non-coding portions of the mRNA encoding the R3 polypeptide, and/or such mutation may reside in nucleic acid sequence(s) comprised in pre-mRNA encoding the R3 polypeptide, but removed (spliced out) from the mature mRNA encoding the R3 polypeptide. Hence, "a mutation in R3" that may be denoted as "a mutation in R3 gene" may also be denoted as a mutation in the nucleic acid sequence encoding R3, in the sense that the mutation may be the nucleic acid sequence encoding R3 pre-mRNA, R3 mRNA and/or R3 ORF.

Any types of mutations achieving the intended effects, such as affecting a given BLV polypeptide (e.g., the level of production and/or the amino acid sequence of the polypeptide), are contemplated herein. For example, suitable mutations may include deletions, insertions, and/or substitutions, The term "deletion" refers to a mutation wherein one or more nucleotides, typically consecutive nucleotides, of a nucleic acid are removed, i.e., deleted, from the nucleic acid. The term "insertion" refers to a mutation wherein one or more nucleotides, typically consecutive nucleotides, are added, i.e., inserted, into a nucleic acid. The term "substitution" refers to a mutation wherein one or more nucleotides of a nucleic acid are each independently replaced, i.e., substituted, by another nucleotide.

In certain embodiments, a mutation may introduce a premature in-frame stop codon into the ORF coding for a given BLV polypeptide. Such premature stop codon may lead to production of a C-terminally truncated form of said polypeptide (this may preferably affect, such as diminish or abolish, some or all biological function(s) of the polypeptide) or, especially when the stop codon is introduced close to (e.g., about 20 or less, or about 10 or less amino acids downstream of) the translation initiation codon of the ORF, the stop codon may effectively abolish the production of the polypeptide. Various ways of introducing a premature in-frame stop codon in the ORF coding for the BLV polypeptide are apparent to a skilled person. For example but without limitation, a suitable insertion, deletion or substitution of one or more nucleotides in the ORF may introduce the premature in-frame stop codon.

In other embodiments, a mutation may introduce a frame shift (e.g., +1 or +2 frame shift) in the ORF coding for a given BLV polypeptide. Typically, such frame shift may lead to a previously out-of-frame stop codon downstream of the mutation becoming an in-frame stop codon. Hence, such frame shift may lead to production of a form of the polypeptide having an alternative C-terminal portion and/or a C-terminally truncated form of said polypeptide (this may preferably affect, such as diminish or abolish, some or all biological function(s) of the polypeptide) or, especially when the mutation is introduced close to (e.g., about 20 or less, or about 10 or less amino acids downstream of) the translation initiation codon of the ORF, the frame shift may effectively abolish the production of the polypeptide. Various ways of introducing a frame shift in the ORF coding for the BLV polypeptide are apparent to a skilled person. For example but without limitation, a suitable insertion or deletion of one or more (not multiple of 3) nucleotides in the ORF may lead to a frame shift.

In further embodiments, a mutation may delete at least a portion of the ORF coding for a given BLV polypeptide. Such deletion may lead to production of an N-terminally truncated form, a C-terminally truncated form and/or an internally deleted form of said polypeptide (this may preferably affect, such as diminish or abolish, some or all biological function(s) of the polypeptide). Preferably, the deletion may remove about 20% or more, or about 50% or more of the ORF's nucleotides. Especially when the deletion removes a sizeable portion of the ORF (e.g., about 50% or more, preferably about 60% or more, more preferably about 70% or more, even more preferably about 80% or more, still more preferably about 90% or more of the ORF's nucleotides) or when the deletion removes the entire ORF, the deletion may effectively abolish the production of the polypeptide. The skilled person can readily introduce such deletions.

In certain other embodiments, a mutation may be a substitution of one or more nucleotides in the ORF coding for a given BLV polypeptide resulting in substitution of one or more amino acids of said BLV polypeptide. Such mutation may typically preserve the production of the polypeptide, and may preferably affect, such as diminish or abolish, some or all biological function(s) of the polypeptide. The skilled person can readily introduce such substitutions.

In certain preferred embodiments, a mutation may abolish native splicing of a pre-mRNA encoding a given BLV polypeptide. In the absence of native splicing, the pre-mRNA may be degraded, or the pre-mRNA may be alternatively spliced, yielding mRNA(s) encoding other BLV polypeptide(s), or the pre-mRNA may be spliced improperly employing latent splice site(s) if available. Hence, such mutation may typically effectively abolish the production of the polypeptide's mRNA and thus the production of the polypeptide. Various ways of interfering with proper splicing are available to a skilled person, such as for example but without limitation, mutations which alter the sequence of one or more sequence elements required for splicing to render them inoperable, or mutations which comprise or consist of a deletion of one or more sequence elements required for splicing.

The terms "splicing", "splicing of a gene", "splicing of a pre-mRNA" and similar as used herein are synonymous and have their art-established meaning. By means of additional explanation, splicing denotes the process and means of removing intervening sequences (introns) from pre-mRNA in the process of producing mature mRNA. The reference to splicing particularly aims at native splicing such as occurs under normal physiological conditions. The terms "pre-mRNA" and "transcript" are used herein to denote RNA species that precede mature mRNA, such as in particular a primary RNA transcript and any partially processed forms thereof. Sequence elements required for splicing refer particularly to cis elements in the sequence of pre-mRNA which direct the cellular splicing machinery (spliceosome) towards correct and precise removal of introns from the pre-mRNA. Sequence elements involved in splicing are generally known per se and can be further determined by known techniques including inter alia mutation or deletion analysis. By means of further explanation, "splice donor site" or "5' splice site" generally refer to a conserved sequence immediately adjacent to an exon-intron boundary at the 5' end of an intron. Commonly, a splice donor site may contain a dinucleotide GU, and may involve a consensus sequence of about 8 bases at about positions +2 to −6. "Splice acceptor site" or "3' splice site" generally refers to a conserved sequence immediately adjacent to an intron-exon boundary at the 3' end of an intron. Commonly, a splice acceptor site may contain a dinucleotide AG, and may involve a consensus sequence of about 16 bases at about positions −14 to +2.

Reference herein to a mutation which abolishes splicing of a given gene, such as in particular splicing at a given exon-intron or intron-exon boundary, may in particular encompass a mutation involving the respective splice donor site or a mutation involving the respective splice acceptor site, whereby splicing at said splice donor site or splice acceptor site is abolished due to said mutation.

For example, a mutation involving a splice donor site may comprise or consist of a deletion, insertion and/or substitution of one or more nucleotides, thereby changing the sequence of the splice donor site. The change in the sequence the splice donor site may involve a change of any one or more nucleotides constituting the splice donor consensus sequence, more preferably may involve a change of any one or both of the 5' most two nucleotides of an intron. For example, a deletion of a given splice donor site may refer to a deletion of any one or both of the 5' most two nucleotides of an intron, e.g., a deletion of at least 1, at least 2, at least 3, at least 4, at least 5, at least 6, or at least 10 5' most nucleotides of an intron, and optionally an additional deletion of at least 1, at least 2, at least 3, at least 4, at least 5, at least 6, or at least 10 3' most nucleotides of the upstream exon.

For example, a mutation involving a splice acceptor site may comprise or consist of a deletion, insertion and/or substitution of one or more nucleotides, thereby changing the sequence of the splice acceptor site. The change in the sequence the splice acceptor site may involve a change of any one or more nucleotides constituting the splice acceptor consensus sequence, more preferably may involve a change of any one or both of the 3' most two nucleotides of an intron. For example, a deletion of a given splice acceptor site may refer to a deletion of any one or both of the 3' most two nucleotides of an intron, e.g., a deletion of at least 1, at least 2, at least 3, at least 4, at least 5, at least 6, or at least 10 3' most nucleotides of an intron, and optionally an additional deletion of at least 1, at least 2, at least 3, at least 4, at least 5, at least 6, or at least 10 5' most nucleotides of the downstream exon.

A skilled reader shall appreciate that various combinations of such exemplary types of mutations as mentioned above are foreseen herein.

The recombinant attenuated BLV and related aspects as disclosed herein comprise certain mutations as specified herein. The mutations are configured such as to not affect or not detrimentally affect BLV polypeptides (e.g., the level of production and/or the amino acid sequence of such BLV polypeptides) or other products, such as miRNA (e.g., the level of production and/or the nucleic acid sequence of such miRNA), which are not specified to be mutated.

Hence, for example, a mutation in the X region of the BLV nucleic acid sequence, said mutation abolishing the production of at least one or preferably all microRNA encoded by said X region, may be configured such as to not affect or not detrimentally affect BLV polypeptides encoded by gag, pol, env, R3, G4, Tax and Rex. Particular care when introducing a mutation in the miRNA region of BLV may need to be given to not affect or not detrimentally affect BLV polypeptides encoded by env and R3, which are adjacent to the miRNA region of BLV. In another example, a mutation in G4 restricting the propagation of the BLV in vivo may be configured such as to not affect or not detrimentally affect BLV polypeptides encoded by gag, pol, env, R3, Tax and Rex, and BLV miRNAs. Particular care when introducing a mutation in G4 may need to be given to not affect or not detrimentally affect BLV polypeptides encoded by R3, Tax and Rex, which are adjacent to/overlapping with G4. In a further example, a mutation in R3 restricting the propagation of the BLV in vivo may be configured such as to not affect or not detrimentally affect BLV polypeptides encoded by gag, pol, env, G4, Tax and Rex, and BLV miRNAs. Particular care when introducing a mutation in R3 may need to be given to not affect or not detrimentally affect BLV polypeptides encoded by G4, Tax and Rex, which are adjacent to/overlapping with R3.

Notwithstanding, it shall be understood that where mutations in two or more of miRNA region, R3, and G4 are specified, such as mutations in R3 and G4, or mutations in miRNA region and R3, or mutations in miRNA region, R3 and G4, a single mutation (e.g., a single deletion) may suitably affect (span) both or all three so-specified genes or regions.

The skilled reader is well aware how mutation(s) intended herein may be configured such as to not affect or not detrimentally affect BLV polypeptides or other products, such as miRNA, which are not specified to be mutated. Preferably, the mutation(s) may be located such as not to modify the transcription, splicing, translation and amino acid sequence of such non-mutated BLV polypeptides or not to modify the transcription and nucleic acid sequence of the non-mutated miRNA. For example, in order to not modify the amino acid sequence of the non-mutated BLV polypeptides, the mutation(s) may be located such as to avoid the ORFs of the non-mutated BLV polypeptides, or if present in the ORFs, to be silent, i.e., to not produce any amino acid change in the non-mutated BLV polypeptides. For example, in order to not modify the splicing of the pre-mRNA encoding the non-mutated BLV polypeptides, the mutation(s) may be located such as to avoid sequence elements required for splicing of the pre-mRNA encoding the non-mutated BLV polypeptides. For example, in order to not modify the nucleic acid sequence of the non-mutated miRNAs, the mutation(s) may be located such as to avoid the sequence(s) encoding the non-mutated miRNAs.

Techniques for introducing mutations into nucleic acids are well-known to the skilled person and include, for example, but without limitation site-directed mutagenesis by PCR, homologous recombination, restriction enzyme digestion and ligation, etc. Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); Innis et al., PCR Protocols: A Guide to Methods and Applications, Academic Press: San Diego, 1990.

Figure 1B:
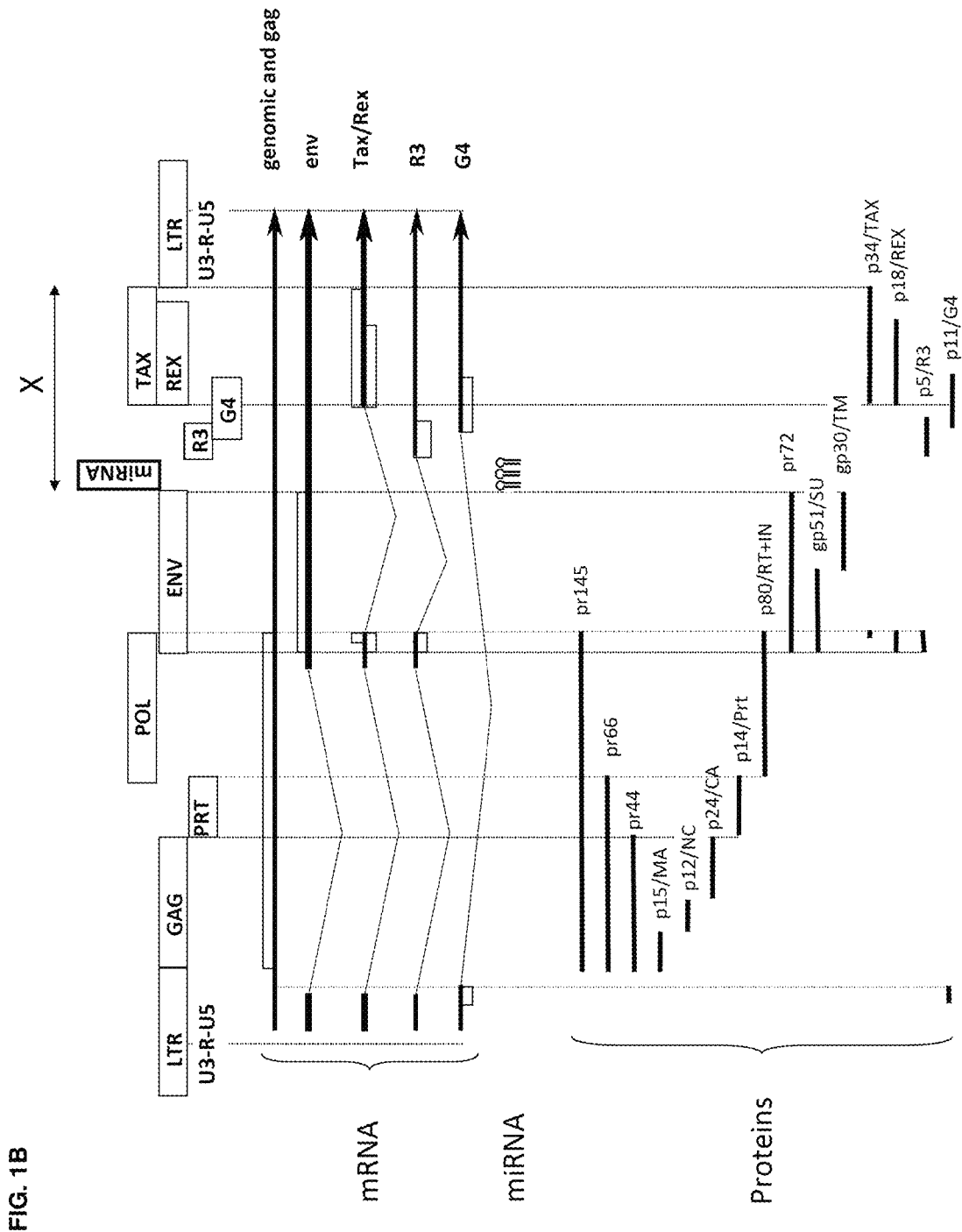
Figure 1C:
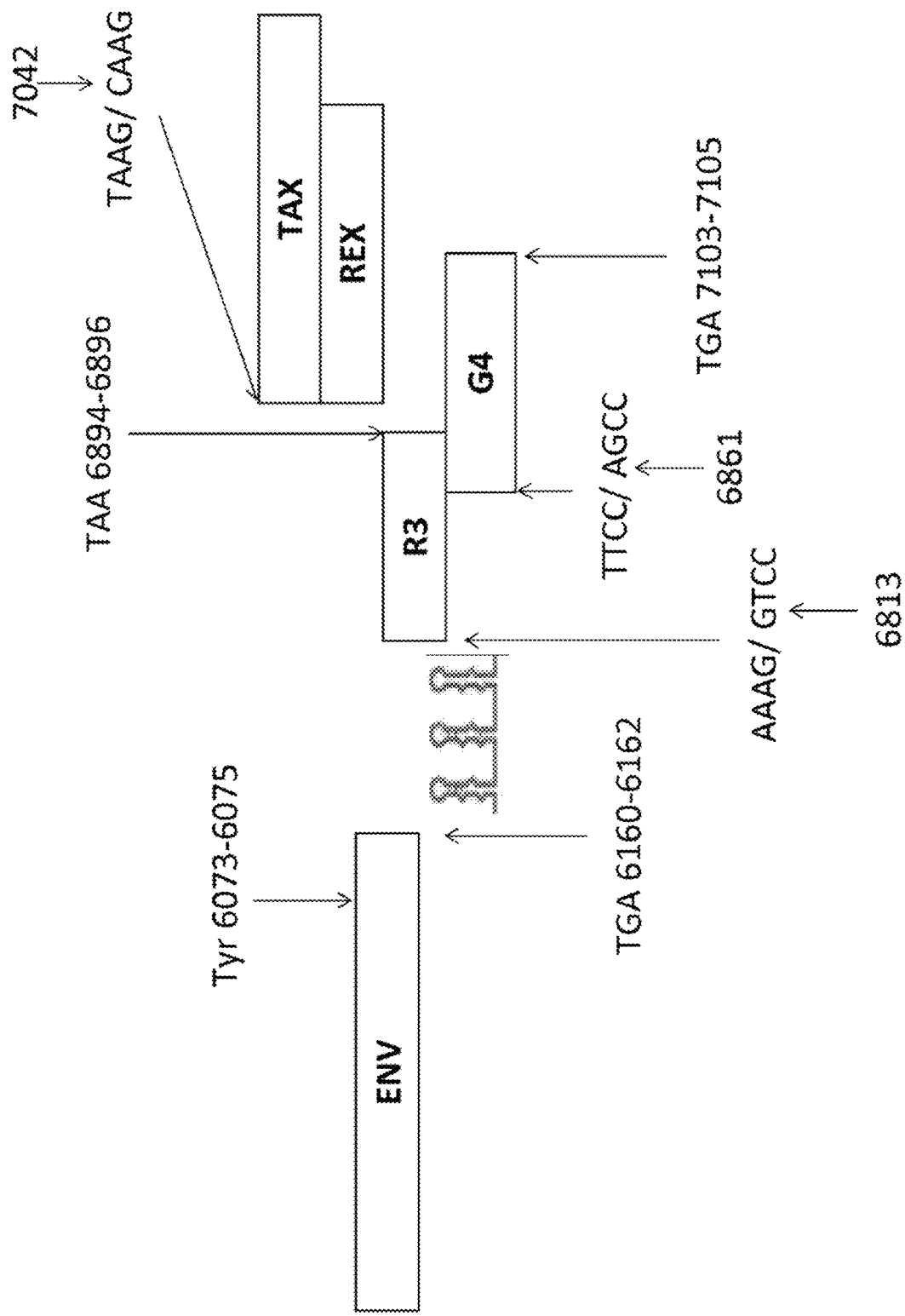
Figure 1E:
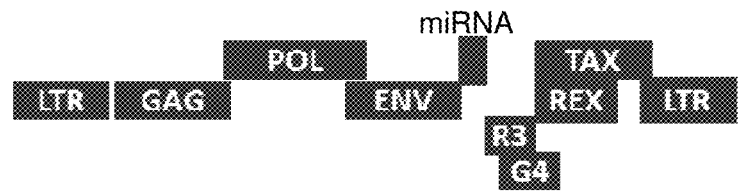
Figure 1F:

The BLV genome comprises long terminal repeats (LTRs) bordering the genome at its 5' terminus and its 3' terminus (FIG. 1B). The BLV genome further comprises structural gag, prt, pol and env genes required for the synthesis of the viral particle. In addition, the BLV genome contains a region between the 3' end of the env gene and the 3' LTR, referred to as the X region, which comprises from 5' to 3' a region encoding microRNAs and open reading frames encoding, the accessory proteins R3 and G4, Tax and Rex (FIG. 1B, 1C).

The term "envelope" as used herein refers to the BLV envelope encoded by the env gene of the BLV genome. The BLV envelope is a multimeric complex comprising an extracellular subunit gp51 (SU) associated with a transmembrane protein gp30 (TM) through disulfide bonds. Both subunits are glycosylated polypeptides (glycoproteins). Nucleotide sequence of the envelope gene portion coding for the gp30 glycoprotein is located from position 5518 to position 6162 (stop codon at 6160-6162, FIG. 1C).

Note that as a suitable point of reference, numbering of nucleotides or amino acids throughout the present disclosure are according to the sequence described in Rice et al. 1987 (Sequence analysis of the Bovine Leukemia Virus Genome. In A. Burney and M. Mammerickx (ed.), Enzootic bovine leukosis and bovine leukemia virus. Martinus Nijhof, Leiden, The Netherlands, pp. 115-144): nucleotide 1 is the first at the 5' end of the R region of the 5' long terminal repeat (LTR). A certain portion of the "Rice" sequence (nucleotides 5790 to position 7409) that may particularly aid the perusal of the present specification is reproduced in FIG. 1D. Further, the complete genomic sequence of BLV 344 provirus from pBLV344H is reproduced in FIGS. 11A-11H (SEQ ID NO: 39). As described in the experimental section, BLV proviruses according to certain embodiments of the invention have been derived form pBLV344H.

Understandably, due to natural sequence variation occurring between various BLV strains, variants, clones, isolates and genotypes, the sequence elements and features referred to herein may be located at different positions in such other BLV than they are in the BLV sequence published by Rice et al. 1987 supra. Hence, the "Rice" numbering adopted herein is not intended to be limiting, but rather is intended to aid the perusal of this specification. The skilled person can readily determine the actual positions of the sequence elements and features referred to herein in the respective sequences of such other BLV strains, variants, clones, isolates and genotypes.

The term "ITAM" or "immunoreceptor tyrosine-based activation motif" generally refers to a conserved YXXL sequence of amino acids, wherein X represents a variable residue, and is involved in signal transduction, in particular signal transduction in immune cells. As used herein, the term specifically refers to the YXXL motifs present in the cytoplasmic tail of the transmembrane envelope protein. The C-terminal cytoplasmic tail of gp30 contains three such YXXL motifs, which are involved in signal transduction (Willems et al. 1995. J. Virol. 69: 4137-4141). In the "Rice" sequence, nucleotide sequence encoding the most N-terminal YXXL motif of gp30 is located from position 6073 to position 6084 of (FIG. 1C).

The term "R3 polypeptide" refers herein to the accessory protein R3 which might have a regulatory function of viral expression, in particular by inhibiting the post-transcriptional regulator of viral expression Rex (Alexandersen et al. 1993. J. Virol. 67: 39-52). The R3 gene and R3 pre-mRNA contain 3 exons (herein consecutively numbered from 5' as exon 1, 2, 3), which are present in R3 mRNA, and two intervening introns (herein consecutively numbered from 5' as intron 1, 2), which are spliced out of R3 mRNA (FIG. 1B). The first two exons of R3 are common with the Tax/Rex mRNA. The R3 ORF starts in exon 2 and continues into exon 3 (FIG. 1B). Hence, the 44-amino-acid R3 polypeptide is composed of an N-terminal region of 17 amino acids coded for by the second exon, which region is identical to that of the Rex polypeptide, and 27 amino acids coded for by exon 3. In the "Rice" sequence, the sequence AAAG/GTCC (positions 6809-6816) defines the intron 2-exon 3 boundary of R3 and the first nucleotide of exon 3 of R3 at position 6813 (FIG. 1C), The term "G4 polypeptide" refers herein to the accessory protein G4 which has oncogenic potential (Lefèbvre et al. 2002. J. Virol. 76: 1400-1414). The G4 gene and G4 pre-mRNA contain 2 exons (herein consecutively numbered from 5' as exon 1, 2), which are present in G4 mRNA, and one intervening intron (herein numbered as intron 1), which is spliced out of G4 mRNA (FIG. 1B). The G4 ORF starts in the first exon in the R region of the 5' LTR and continues into the second exon (FIG. 1B), yielding a protein of 105 amino acids. In the "Rice" sequence, the sequence TTCC/AGCC (positions 6857-6864) defines the intron 1-exon 2 boundary of G4 and the first nucleotide of exon 2 of G4 at position 6861 (FIG. 1C).

The terms "microRNA" or "miRNA" generally refer to short RNA molecules of 22 nucleotides on average. They are generally involved in post-transcriptional regulation of gene expression through binding to complementary sequences on target messenger RNA transcripts, usually resulting in translational repression or target degradation and gene silencing. They are often implicated in disease states, including cancer. As used herein, the term specifically refers to the miRNAs encoded by the BLV genome. The miRNA encoding region is located in the X region of the BLV genome (as noted previously, X region defines the region between the 3' end of the env gene and the 3' LTR), in particular between the 3' end of the env gene and the start of the R3 ORF region located in the X region (Cullen, 2012. PNAS 109: 2695-2696). In the "Rice" sequence, the miRNA encoding region may be deemed as located from 6163 to position 6812.

By means of further guidance, Kincaid et al. 2012 (Proc Natl Acad Sci USA 109(8): 3077-82) has recently mapped eight BLV-encoded miRNA sequences—annotated as BLV-mir-B1-3p, BLV-mir-B2-5p, BLV-mir-B2-3p, BLV-mir-B3-5p, BLV-mir-B3-3p, BLV-mir-B4-3p, BLV-mir-B5-5p, BLV-mir-B5-3p—to the above-mentioned miRNA encoding region of the BLV nucleic acid sequence. Kincaid et al. 2012 proposed the following consensus sequences for these miRNA's:

```
                                        (SEQ ID NO: 20)
BLV-mir-B1-3p:    TCAGTGTACCATCACAAGCCTCT (SEQ ID NO: 21)
BLV-mir-B2-5p:    ATGACTGAGTGTAGCGCAGAGA (SEQ ID NO: 22)
BLV-mir-B2-3p:    TGCGTGTCRCTCAGTCATTTT (SEQ ID NO: 23)
BLV-mir-B3-5p:    ATCCCCCTGCCAGCGTTGGTC (SEQ ID NO: 24)
BLV-mir-B3-3p:    TAACGCTGACGGGGGCGATTTCT (SEQ ID NO: 25)
BLV-mir-B4-3p:    TAGCACCAYVGTCTCTGCGCCTTT (SEQ ID NO: 26)
BLV-mir-B5-5p:    AGGARGGTTGTGGCTCAGAGGT (SEQ ID NO: 27)
BLV-mir-B5-3p:    CTCGRRCCGCAACCTCCCTTTCT.
```

Rosewick et al. 2013 (Proc Natl Acad Sci USA, PMID: 23345446) confirmed these findings and further identified BLV-mir-B1-5p and BLV-mir-B4-5p, with the following consensus sequences:

```
                                        (SEQ ID NO: 28)
BLV-mir-B1-5p:    AGGCTGTGGTGGBGCRCTGGCT (SEQ ID NO: 29)
BLV-mir-B4-5p:    AAGCGRGAGGCTCTGGTGCTGG.
```

Rosewick et al. 2013 further determined that the BLV miRNAs resulted from the transcription of five independent transcriptional units encoding five hairpin structures in the BLV miRNA encoding region.

The terms "Tax polypeptide" and "Rex polypeptide" refer herein to the regulatory proteins Tax and Rex. Tax, the transactivating protein, stimulates the 5' long terminal repeat to promote viral transcription and may be involved in tumorigenesis. Rex is involved in the transition from early expression of regulatory proteins to later expression of viral structural proteins. The Tax/Rex gene and Tax/Rex pre-mRNA contain 3 exons (herein consecutively numbered from 5' as exon 1, 2, 3), which are present in Tax/Rex mRNA, and two intervening introns (herein consecutively numbered from 5' as intron 1, 2), which are spliced out of Tax/Rex mRNA (FIG. 1B). The Tax ORF and Rex ORF both start in exon 2 and continue into exon 3 (FIG. 1B), but employ distinct translation initiation codons, distinct stop codons, and encode distinct proteins of 309 (Tax) and 156 (Rex) amino acids. In the "Rice" sequence, the sequence TAAG/CAAG (positions 7038-7045) defines the intron 2-exon 3 boundary of Tax/Rex and the first nucleotide of exon 3 of Tax/Rex at position 7042 (FIG. 1C).

As noted, the recombinant attenuated BLV and related aspects as disclosed herein may comprise a mutation in the nucleic acid sequence encoding the most N-terminal YXXL signalling motif of the cytoplasmic domain of the transmembrane subunit (TM) of the envelope protein, said mutation disrupting the signal transduction activity of the motif.

To assess the signal transduction activity of the YXXL motif, calcium responses and cytokine production may be analysed in a lymphoid cell line, such as a B or T cell line, which has been stably transfected with a chimeric molecule comprising the extracellular and transmembrane portions of CD8 fused to the cytoplasmic tail of TM, in response to an anti-CD8 antibody as described in Beaufils et al. (1993. EMBO J. 12: 5105-5112).

In preferred embodiments, the mutation in the most N-terminal YXXL signalling motif of the cytoplasmic domain of the transmembrane subunit (TM) of the envelope protein disrupting the signal transduction activity of the motif is a substitution of the tyrosine residue of the motif, i.e., the tyrosine residue at position 186 of the BLV TM protein. The tyrosine residue may be substituted by any other amino acid residue, preferably by any other naturally occurring amino acid residue, more preferably wherein such residue does not comprise a hydroxyl moiety. Particularly suitable substitutions of the tyrosine residue include substitutions of the tyrosine residue with alanine or aspartic acid residues, preferably with aspartic acid residue (i.e., Y186D, resulting in the motif DXXL).

Accordingly, in preferred embodiments the mutation in the most N-terminal YXXL signalling motif of the cytoplasmic domain of the transmembrane subunit (TM) of the envelope protein as intended herein is a mutation of the TAT codon at positions 6073-6075 of the nucleic acid encoding BLV into a codon encoding an amino acid residue other than tyrosine, i.e., a codon other than TAT and TAC, preferably into a codon encoding alanine (GCT, GCC, GCA, or GCG) or aspartic acid (GAT or GAC) residues, preferably into a codon encoding aspartic acid residue (GAT or GAC). In certain embodiments, the mutation may be a missense point mutation (i.e., a mutation of a single nucleotide changing the amino acid encoding by the codon), in a particularly preferred example a point mutation of the T nucleotide at position 6073 of the nucleic acid encoding BLV, preferably BLV provirus, to a G nucleotide (i.e., TAT→GAT, resulting in Tyr→Asp).

As noted, the recombinant attenuated BLV and related aspects as disclosed herein may comprise a mutation in G4 restricting the propagation of the BLV in vivo.

As also noted, the recombinant attenuated BLV and related aspects as disclosed herein may comprise a mutation in R3 restricting the propagation of the BLV in vivo.

In these contexts, the phrase "restricting the propagation of the BLV in vivo" denotes that a BLV virus carrying the mutation in G4 or in R3, or in both G4 and R3, exhibits reduced propagation in a host, i.e., in vivo, compared to a reference BLV virus which is otherwise identical but does not comprise the mutation in G4 or in R3, or in both G4 and R3, respectively, preferably compared to a reference BLV virus which is otherwise identical but comprises wild-type G4 or R3, or both G4 and R3, respectively. The host may be as defined elsewhere in this specification, such as particularly cattle, such as more particularly a cow. The propagation of the virus in the host may be at least about 2 fold, e.g., at least about 5 fold, or preferably at least about 10 fold, e.g., at least about 20 fold, or more preferably at least about 50 fold, e.g., at least about 100 fold or less than that of the reference virus. Suitable methods for measuring the propagation of a virus, in particular BLV, in the host include without limitation determining the proviral loads in the challenged host. For example, the number of BLV proviral copies may be determined using a suitable methodology, e.g., quantitative PCR, per a given number, e.g., 100, of peripheral blood mononuclear cells at a given time or times, i.e., in function of time, following the challenge of the host. See Example 3 for a specific, non-limiting application of this approach.

In certain embodiments, the mutation in G4 restricting the propagation of the BLV in vivo may abolish the production of G4 polypeptide.

In certain other embodiments, the mutation in G4 restricting the propagation of the BLV in vivo may result in production of a C-terminally truncated G4 polypeptide lacking at least 20 C-terminal amino acids of G4 polypeptide (e.g., ≥21, ≥22, ≥23, ≥24, ≥25, ≥26, ≥27, ≥28, ≥29) or may result in production of a C-terminally truncated G4 polypeptide lacking at least 30 C-terminal amino acids of G4 polypeptide (e.g., ≥31, ≥32, ≥33, ≥34, ≥35, ≥36, ≥37, ≥38, ≥39), such as may result in production of a C-terminally truncated G4 polypeptide lacking between about 30 and about 40, e.g., between about 33 and about 47, e.g., about 35 C-terminal amino acids of G4 polypeptide.

In certain other embodiments, the mutation in G4 restricting the propagation of the BLV in vivo may inactivate G4 polypeptide such as to at least abolish the oncogenic potential of G4 polypeptide. The oncogenic potential of G4 may be assessed through testing its transforming potential in vitro. For example, tumour formation may be examined in immunocompromised mice, such as, e.g., thymus-less nude mice, injected with embryonic cells, such as, e.g., rat embryonic fibroblasts, that have been co-transfected with nucleic acid encoding BLV G4 and an expression vector comprising an oncogene, preferably Ha-ras (Kerkhofs et al. 1998. J. Virol. 72: 2554-2559).

Care when introducing a mutation in G4 may need to be given to not affect or not detrimentally affect R3 (where R3 mutation as taught herein is not specified), Tax and Rex, as explained elsewhere in this specification. Hence, the mutation is compatible with production of functional Tax and Rex proteins.

A suitable mutation in G4 restricting the propagation of the BLV in vivo may be located in any exon (e.g., exon 1 or 2) and/or intron 1 of G4. For example, the mutation may be located in any exon (e.g., exon 1 or 2) of G4. In a further example, the mutation may be located in G4 ORF, such as in the portion of G4 ORF present in exon 1 or in the portion of G4 ORF present in exon 2.

Without limitation, a suitable mutation in G4 restricting the propagation of the BLV in vivo may be located in exon 1 of G4, preferably in the portion of G4 ORF present in exon 1. For example, a premature in-frame stop codon or a frame shift mutation introduced in the portion of G4 ORF present in exon 1 would abolish production of G4. Such mutation does not affect or does not detrimentally affect the function of the 5' LTR or the production of other BLV polypeptides or products.

Also without limitation, a suitable mutation in G4 restricting the propagation of the BLV in vivo may be located in the splice donor site of intron 1 of G4 and may abolish native splicing of G4 pre-mRNA and thereby abolish production of G4 polypeptide, e.g., a deletion comprising or consisting of a deletion of said splice donor site of intron 1 of G4.

Preferably, the mutation in G4 restricting the propagation of the BLV in vivo may be located in the X region of the BLV nucleic acid sequence. In particular, the portions of G4 present in the X region of the BLV nucleic acid sequence include a 3' portion of intron 1 and exon 2.

Without limitation, a suitable mutation in G4 restricting the propagation of the BLV in vivo may be located in the splice acceptor site of intron 1 of G4 and may abolish native splicing of G4 pre-mRNA and thereby abolish production of G4 polypeptide, e.g., a deletion comprising or consisting of a deletion of said splice acceptor site of intron 1 of G4.

Also without limitation, a suitable mutation in G4 restricting the propagation of the BLV in vivo may be located in exon 2 of G4, preferably in the portion of G4 ORF present in exon 2. For example, a premature in-frame stop codon, a frame shift mutation, a deletion or a substitution introduced in the portion of G4 ORF present in exon 2 could produce C-terminally truncated G4 polypeptide or G4 polypeptide with altered amino acid sequence having diminished or abolished biological function(s), such as for example at least abolished oncogenic potential, or could abolish the production of G4.

Particular care especially when introducing a mutation in G4 in the X region of the BLV nucleic acid sequence may need to be given to not affect or not detrimentally affect the miRNA region (where miRNA mutation as taught herein is not specified), R3 (where R3 mutation as taught herein is not specified), Tax and Rex, as explained elsewhere in this specification. Hence, the mutation is compatible with production of functional Tax and Rex proteins.

More preferably, the mutation in G4 restricting the propagation of the BLV in vivo may be located in the region of the BLV nucleic acid sequence between the stop codon of R3 and the splice acceptor site of intron 2 of Tax/Rex. Advantageously, mutating this portion of G4 can ensure that no detrimental changes are introduced into the R3 (where R3 mutation as taught herein is not specified), Tax and Rex. This region corresponds to positions 6897 to 7039 according to the "Rice" sequence numbering, starting at the first nucleotide downstream of the R3 stop codon located at 6894-6896 and extending to nucleotide −3 of the intron 2-exon 3 boundary of Tax/Rex at position 7039, i.e., excluding the last two nucleotides of intron 2 of Tax/Rex at positions 7040-7041.

Without limitation, a premature in-frame stop codon, a frame shift mutation, a deletion or a substitution introduced in the region of the BLV nucleic acid sequence between the stop codon of R3 and the splice acceptor site of intron 2 of Tax/Rex could produce C-terminally truncated G4 polypeptide or G4 polypeptide with altered amino acid sequence having diminished or abolished biological function(s), such as for example at least abolished oncogenic potential, or could abolish the production of G4.

Also without limitation, a deletion in G4 may remove a sizeable portion of the region of the BLV nucleic acid sequence between the stop codon of R3 and the splice acceptor site of intron 2 of Tax/Rex, such as, e.g., about 50% or more, preferably about 60% or more, more preferably about 70% or more, even more preferably about 80% or more, still more preferably about 90% or more of the nucleotides constituting this region. Hence, without limitation, a deletion in G4 may remove a sizeable portion of the region of the BLV nucleic acid sequence between the stop codon of R3 and the splice acceptor site of intron 2 of Tax/Rex, such as, e.g., about 70 nucleotides or more, preferably about 90 nucleotides or more, more preferably about 110 nucleotides or more, even more preferably about 130 nucleotides or more, of the nucleotides constituting this region. This could produce C-terminally truncated or internally deleted G4 polypeptide having diminished or abolished biological function(s), such as for example at least abolished oncogenic potential, or could abolish the production of G4.

Preferably, the mutation in G4 restricting the propagation of the BLV in vivo may comprise or consist of an insertion of an in-frame stop codon in the G4 open reading frame. This can produce C-terminally truncated G4 polypeptide having diminished or abolished biological function(s), such as for example at least abolished oncogenic potential, or can abolish the production of G4.

Particularly preferably, the mutation in G4 restricting the propagation of the BLV in vivo may comprise or consist of an insertion of an in-frame stop codon in the G4 open reading frame in the region of the BLV nucleic acid sequence between the stop codon of R3 and the splice acceptor site of intron 2 of Tax/Rex. This can produce C-terminally truncated G4 polypeptide having diminished or abolished biological function(s), such as for example at least abolished oncogenic potential, or can abolish the production of G4.

In exemplary non-limiting embodiments, an in-frame stop codon may be introduced, with reference to the "Rice" sequence numbering, between positions 6947 and 7037, such as between positions 6957 and 7037, such as particularly between positions 6967 and 7027, such as more particularly between positions 6977 and 7017, such as even more particularly between positions 6987 and 7007, such as at about position 6997 of the BLV nucleic acid sequence.

In certain embodiments, the mutation in R3 restricting the propagation of the BLV in vivo may abolish the production of R3 polypeptide.

Care when introducing a mutation in R3 may need to be given to not affect or not detrimentally affect G4 (where G4 mutation as taught herein is not specified), Tax and Rex, as explained elsewhere in this specification. Hence, the mutation is compatible with production of functional Tax and Rex proteins.

A suitable mutation in R3 restricting the propagation of the BLV in vivo may be located in any exon (e.g., exon 1, 2 or 3) and/or any intron (e.g., intron 1 or 2) of R3. For example, the mutation may be located in any exon (e.g., exon 1, 2 or 3) of R3. In a further example, the mutation may be located in R3 ORF, such as in the portion of R3 ORF present in exon 2 or in the portion of R3 ORF present in exon 3.

Because exon 1 and 2 of R3 are common with the Tax/Rex mRNA, and the portion of R3 ORF present in exon 2 of R3 is identical to that of Rex, a suitable mutation in R3 restricting the propagation of the BLV may be advantageously located in the 3' portion of intron 2 of R3 or in exon 3 of R3. However, as noted already, mutations in exon 1 or 2 of R3 and in intron 1 or in the 5' portion of intron 2 of R3 that are compatible with production of functional Tax and Rex proteins are also possible and contemplated herein.

Preferably, the mutation in R3 restricting the propagation of the BLV in vivo may be located in the X region of the BLV nucleic acid sequence. In particular, the portions of R3 present in the X region of the BLV nucleic acid sequence include a 3' portion of intron 2 and exon 3.

Without limitation, a suitable mutation in R3 restricting the propagation of the BLV in vivo may be located in the splice acceptor site of intron 2 of R3 and may abolish native splicing of R3 pre-mRNA and thereby abolish production of R3 polypeptide, e.g., a deletion comprising or consisting of a deletion of said splice acceptor site of intron 2 of R3.

Also without limitation, a suitable mutation in R3 restricting the propagation of the BLV in vivo may be located in exon 3 of R3, preferably in the portion of R3 ORF present in exon 3. For example, a premature in-frame stop codon, a frame shift mutation, a deletion or a substitution introduced in the portion of R3 ORF present in exon 3 could produce C-terminally truncated R3 polypeptide or R3 polypeptide with altered amino acid sequence having diminished or abolished biological function(s) or could abolish the production of R3.

Particular care especially when introducing a mutation in R3 in the X region of the BLV nucleic acid sequence may need to be given to not affect or not detrimentally affect the miRNA region (where miRNA mutation as taught herein is not specified), G4 (where G4 mutation as taught herein is not specified), Tax and Rex, as explained elsewhere in this specification. Hence, the mutation is compatible with production of functional Tax and Rex proteins.

For example, the mutation in R3 restricting the propagation of the BLV in vivo may be located in the region of the BLV nucleic acid sequence between the end of the miRNA encoding region and the splice acceptor site of intron 1 of G4, e.g., in the region of the BLV nucleic acid sequence between about 250 nucleotides upstream of the splice acceptor site of intron 2 of R3 and the splice acceptor site of intron 1 of G4).

Advantageously, mutating this portion of R3 can ensure that no detrimental changes are introduced into the miRNA region (where miRNA mutation as taught herein is not specified), G4 (where G4 mutation as taught herein is not specified), Tax and Rex.

For example, a premature in-frame stop codon, a frame shift mutation, a deletion or a substitution introduced in the portion of R3 ORF present in exon 3 upstream of the splice acceptor site of intron 1 of G4 (i.e., the region corresponding to positions 6813 to 6858 according to the "Rice" sequence numbering, starting at the first nucleotide of exon 3 of R3 stop codon located at 6813 and extending to nucleotide −3 of the intron 1-exon 2 boundary of G4 at 6858, i.e., excluding the last two nucleotides of intron 1 of G4 at positions 6859-6860) could produce C-terminally truncated R3 polypeptide or R3 polypeptide with altered amino acid sequence having diminished or abolished biological function(s) or could abolish the production of R3.

For example, a deletion in R3 may remove a sizeable portion of the portion of R3 ORF present in exon 3 upstream of the splice acceptor site of intron 1 of G4, i.e., the region corresponding to positions 6813 to 6858 according to the "Rice" sequence numbering. A sizeable portion of this region may be for example about 50% or more, preferably about 60% or more, more preferably about 70% or more, even more preferably about 80% or more, still more preferably about 90% or more of the nucleotides constituting this region. This could produce C-terminally truncated or internally deleted R3 polypeptide having diminished or abolished biological function(s) or could abolish the production of R3.

Preferably, the mutation in R3 restricting the propagation of the BLV in vivo may abolish splicing at the intron 2-exon 3 boundary of R3 pre-messenger RNA. Hereby, native splicing of R3 pre-mRNA and production of R3 polypeptide can be abolished. Any mutation involving the splice acceptor site of intron 2 of R3 is contemplated herein. Preferably, the mutation may comprise or consist of a deletion of the splice acceptor site of intron 2 of R3.

Particularly preferably, the mutation in R3 restricting the propagation of the BLV in vivo may be a deletion of at least a portion of the region of the BLV nucleic acid sequence between the end of the miRNA encoding region and the splice acceptor site of intron 1 of G4, more particularly between about 250 nucleotides upstream of the intron 2-exon 3 boundary of R3 and the splice acceptor site of intron 1 of G4, wherein the mutation abolishes splicing at the intron 2-exon 3 boundary of R3 pre-messenger RNA, as explained above. Advantageously, mutating this portion of R3 can ensure that no detrimental changes are introduced into the miRNA region (where miRNA mutation as taught herein is not specified), G4 (where G4 mutation as taught herein is not specified), Tax and Rex.

For example, the 5' boundary of the deletion may be located between about 250 nucleotides upstream of the intron 2-exon 3 boundary of R3 and at the intron 2-exon 3 boundary of R3, or between about 250 and about 10 nucleotides upstream of the intron 2-exon 3 boundary of R3, or between about 250 and about 50 nucleotides upstream of the intron 2-exon 3 boundary of R3, or between about 250 and about 100 nucleotides upstream of the intron 2-exon 3 boundary of R3. For example, the 5' boundary of the deletion may be located between about 249 and about 149, or between about 239 and about 159, or between about 229 and about 169, or between about 219 and about 179, or between about 209 and about 189, or at about 199 nucleotides upstream of the intron 2-exon 3 boundary of R3.

Any of such exemplary 5' boundaries of the deletion listed in the previous paragraph may be combined with a 3' boundary of the deletion located between about 45 and about 3 nucleotides upstream of the intron 1-exon 2 boundary of G4, or any of such exemplary 5' boundaries of the deletion listed in the previous paragraph may be combined with a 3' boundary of the deletion located between about 33 and about 3 nucleotides upstream of the intron 1-exon 2 boundary of G4, or any of such exemplary 5' boundaries of the deletion listed in the previous paragraph may be combined with a 3' boundary of the deletion located between about 23 and about 3 nucleotides upstream of the intron 1-exon 2 boundary of G4, or any of such exemplary 5' boundaries of the deletion listed in the previous paragraph may be combined with a 3' boundary of the deletion at about 13 nucleotides upstream of the intron 1-exon 2 boundary of G4.

For example, the 5' boundary of the deletion may be located between about 249 and about 149, or preferably between about 239 and about 159, or more preferably between about 229 and about 169, or even more preferably between about 219 and about 179, or still more preferably between about 209 and about 189, or particularly preferably at about 199 nucleotides upstream of the intron 2-exon 3 boundary of R3, and the 3' boundary of the deletion may be located between about 45 and about 3, or preferably between about 33 and about 3, or more preferably between about 23 and about 3, or still more preferably at about 13 nucleotides upstream of the intron 1-exon 2 boundary of G4.

In a particular example, the 5' boundary of the deletion may be located between about 209 and about 189, e.g., at about 209, nucleotides upstream of the intron 2-exon 3 boundary of R3 and the 3' boundary of the deletion may be located between about 23 and about 3, e.g., at about 13, nucleotides upstream of the intron 1-exon 2 boundary of G4.

In further preferred embodiments, the 5' boundary of the deletion may be located between positions 6564 and 6664, or preferably between positions 6574 and 6654, or more preferably between positions 6584 and 6644, or even more preferably between positions 6594 and 6634, or still more preferably between positions 6604 and 6624, or particularly preferably at about position 6614 of the BLV nucleic acid sequence according to "Rice" sequence numbering and the 3' boundary of the deletion may be located between positions 6816 and 6858, or preferably between positions 6828 and 6858, or more preferably between positions 6838 and 6858, or still more preferably at about position 6828 of the BLV nucleic acid sequence according to "Rice" sequence numbering. In a particular example, the 5' boundary of the deletion may be located between positions 6604 and 6624, e.g., at about position 6614, of the BLV nucleic acid sequence and the 3' boundary of the deletion may be located between positions 6838 and 6858, e.g., at about position 6848, of the BLV nucleic acid sequence.

In certain embodiments, the recombinant BLV may comprise the mutation in both G4 and R3, said mutation restricting the propagation of the BLV in vivo.

In preferred embodiments, the mutation in both G4 and R3 may abolish the production of both G4 and R3 polypeptides. Preferably, the mutation may be located in the X region of the BLV nucleic acid sequence.

Care when introducing a mutation in both G4 and R3, particularly when introducing such mutation in the X region of the BLV nucleic acid sequence, may need to be given to not affect or not detrimentally affect the miRNA region (where miRNA mutation as taught herein is not specified), Tax and Rex, as explained elsewhere in this specification. Hence, the mutation is compatible with production of functional Tax and Rex proteins.

In certain embodiments, the recombinant BLV may comprise the mutation in G4 restricting the propagation of the BLV in vivo, and the mutation in R3 restricting the propagation of the BLV in vivo, wherein said mutations abolish splicing at the intron 2-exon 3 boundary of R3 pre-messenger RNA and at the intron 1-exon 2 boundary of G4 pre-messenger RNA. Hereby, native splicing of R3 pre-mRNA and production of R3 polypeptide and native splicing of G4 pre-mRNA and production of G4 polypeptide can be abolished. Any mutation involving the splice acceptor site of intron 2 of R3 and any mutation involving the splice acceptor site of intron 1 of G4 is contemplated herein. Preferably, the mutations may comprise or consist of a deletion of the splice acceptor site of intron 2 of R3 and a deletion of the splice acceptor site of intron 1 of G4.

Particularly preferably, said mutations in G4 and in R3 restricting the propagation of the BLV in vivo may be a deletion of at least a portion of the region of the BLV nucleic acid sequence between the end of the miRNA encoding region and the splice acceptor site of intron 2 of Tax/Rex, more particularly between about 250 nucleotides upstream of the intron 2-exon 3 boundary of R3 and the splice acceptor site of intron 2 of Tax/Rex, whereby the splice acceptor site of intron 2 of R3 and the splice acceptor site of intron 1 of G4 are deleted, such that the mutations abolish splicing at the intron 2-exon 3 boundary of R3 pre-messenger RNA and at the intron 1-exon 2 boundary of G4 pre-messenger RNA, as explained above.

For example, the 5' boundary of the deletion may be located between about 250 nucleotides upstream of the intron 2-exon 3 boundary of R3 and at the intron 2-exon 3 boundary of R3, or between about 250 and about 10 nucleotides upstream of the intron 2-exon 3 boundary of R3, or between about 250 and about 50 nucleotides upstream of the intron 2-exon 3 boundary of R3, or between about 250 and about 100 nucleotides upstream of the intron 2-exon 3 boundary of R3. For example, the 5' boundary of the deletion may be located between about 249 and about 149, or between about 239 and about 159, or between about 229 and about 169, or between about 219 and about 179, or between about 209 and about 189, or at about 199 nucleotides upstream of the intron 2-exon 3 boundary of R3.

Any of such exemplary 5' boundaries of the deletion listed in the previous paragraph may be combined with a 3' boundary of the deletion located between about 178 and about 3 nucleotides upstream of the intron 2-exon 3 boundary of Tax/Rex, or any of such exemplary 5' boundaries of the deletion listed in the previous paragraph may be combined with a 3' boundary of the deletion located between about 100 and about 3 nucleotides upstream of the intron 2-exon 3 boundary of Tax/Rex, or any of such exemplary 5' boundaries of the deletion listed in the previous paragraph may be combined with a 3' boundary of the deletion located between about 55 and about 35 nucleotides upstream of the intron 2-exon 3 boundary of Tax/Rex, or any of such exemplary 5' boundaries of the deletion listed in the previous paragraph may be combined with a 3' boundary of the deletion at about 45 nucleotides upstream of the intron 2-exon 3 boundary of Tax/Rex.

For example, the 5' boundary of the deletion may be located between about 249 and about 149, or preferably between about 239 and about 159, or more preferably between about 229 and about 169, or even more preferably between about 219 and about 179, or still more preferably between about 209 and about 189, or particularly preferably at about 199 nucleotides upstream of the intron 2-exon 3 boundary of R3, and the 3' boundary of the deletion may be located between about 178 and about 3, or preferably between about 100 and about 3, or more preferably between about 55 and about 35, or still more preferably at about 45 nucleotides upstream of the intron 2-exon 3 boundary of Tax/Rex.

In a particular example, the 5' boundary of the deletion may be located between about 209 and about 189, e.g., at about 209, nucleotides upstream of the intron 2-exon 3 boundary of R3 and the 3' boundary of the deletion may located between about 55 and about 35, e.g., at about 45, nucleotides upstream of the intron 2-exon 3 boundary of Tax/Rex.

In further preferred embodiments, the 5' boundary of the deletion may be located between positions 6564 and 6664, or preferably between positions 6574 and 6654, or more preferably between positions 6584 and 6644, or even more preferably between positions 6594 and 6634, or still more preferably between positions 6604 and 6624, or particularly preferably at about position 6614 of the BLV nucleic acid sequence according to "Rice" sequence numbering and the 3' boundary of the deletion may be located between positions 6957 and 7037, or preferably between positions 6967 and 7027, or more preferably between positions 6977 and 7017, or even more preferably between positions 6987 and 7007, or still more preferably at about position 6997 of the BLV nucleic acid sequence according to "Rice" sequence numbering. In a particular example, the 5' boundary of the deletion may be located between positions 6604 and 6624, e.g., at about position 6614, of the BLV nucleic acid sequence and the 3' boundary of the deletion may be located between positions 6987 and 7007, e.g., at about position 6997, of the BLV nucleic acid sequence.

As noted, the recombinant attenuated BLV and related aspects as disclosed herein may comprise a mutation in the X region of the BLV nucleic acid sequence abolishing the production of at least one or preferably all microRNA encoded by said X region. Any mutations, including deletions, insertions and/or substitutions, abolishing the production of at least one or preferably all microRNA encoded by said X region are contemplated herein.

By means of example and not limitation, the mutation in the X region of the BLV nucleic acid sequence abolishing the production of at least one or preferably all microRNA encoded by said X region may abolish the production of—in order of increasing preference—one or more, two or more, three or more, four or more, five or more, six or more, seven or more, eight or more, nine or more, or all ten BLV-encoded miRNA selected from the group consisting of BLV-mir-B1-5p, BLV-mir-B1-3p, BLV-mir-B2-5p, BLV-mir-B2-3p, BLV-mir-B3-5p, BLV-mir-B3-3p, BLV-mir-B4-5p, BLV-mir-B4-3p, BLV-mir-B5-5p, BLV-mir-B5-3p, as defined elsewhere in this specification.

Preferably, the mutation in the X region of the BLV nucleic acid sequence abolishing the production of at least one or preferably all microRNA encoded by said X region may be a deletion of at least a portion of the region of the BLV nucleic acid sequence between the stop codon of the transmembrane subunit (TM, gp30 glycoprotein) of the envelope protein and the splice acceptor site of intron 2 of R3. This region contains the nucleic acid encoding the miRNAs and may be suitably denoted as miRNA region or miRNA encoding region herein.

For example, the mutation in the X region of the BLV nucleic acid sequence abolishing the production of at least one or preferably all microRNA encoded by said X region may be a deletion of at least a portion of the region of the BLV nucleic acid sequence between the stop codon of TM and about 10 or about 20 or about 30 or about 40 or about 50 or about 60 or about 70 or about 80 or about 90 or about 100 or about 150 or about 200 nucleotides upstream of the intron 2-exon 3 boundary of R3.

For example, the 5' boundary of the deletion may be located between about 1 and about 50, preferably between about 1 and about 40, more preferably between about 1 and about 30, even more preferably between about 1 and about 20, still more preferably between about 1 and about 11, such as at about 7, nucleotides downstream of the stop codon of TM and the 3' boundary of the deletion may be located between about 200 and about 3, preferably between about 132 and about 32, more preferably between about 122 and about 42, even more preferably between about 112 and about 52, still more preferably between about 102 and about 62, yet more preferably between about 92 and about 72 nucleotides upstream of the intron 2-exon 3 boundary of R3.

In further preferred embodiments, the 5' boundary of the deletion may be located between positions 6163 and 6213, or preferably between positions 6163 and 6203, or more preferably between positions 6163 and 6193, or even more preferably between positions 6163 and 6183, or still more preferably between positions 6163 and 6173, or particularly preferably at about position 6169 of the BLV nucleic acid sequence according to "Rice" sequence numbering and the 3' boundary of the deletion may be located between positions 6681 and 6781, or preferably between positions 6691 and 6771, or more preferably between positions 6701 and 6761, or even more preferably between positions 6711 and 6751, or still more preferably between positions 6721 and 6741, or particularly preferably at about position 6731 of the BLV nucleic acid sequence according to "Rice" sequence numbering. In a particular example, the 5' boundary of the deletion may be located between positions 6163 and 6173, e.g., at about position 6169, of the BLV nucleic acid sequence and the 3' boundary of the deletion may be located between positions 6721 and 6741, e.g., at about position 6731, of the BLV nucleic acid sequence.

In certain embodiments, the recombinant BLV may comprise a mutation in both G4 and R3, said mutation restricting the propagation of the BLV in vivo, and a mutation in the X region of the BLV nucleic acid sequence abolishing the production of at least one or preferably all microRNA encoded by said X region. In preferred embodiments, the mutation in both G4 and R3 may abolish the production of both G4 and R3 polypeptides; preferably, the mutation may be located in the X region of the BLV nucleic acid sequence. Hence, in certain embodiments, the recombinant BLV may comprise a mutation in the X region of the BLV nucleic acid sequence abolishing the production of both G4 and R3 and abolishing the production of at least one or preferably all microRNA encoded by said X region.

Care when introducing a mutation in miRNA, G4 and R3, particularly when the mutation in both G4 and R3 is in the X region of the BLV nucleic acid sequence, may need to be given to not affect or not detrimentally affect Tax and Rex, as explained elsewhere in this specification. Hence, the mutation is compatible with production of functional Tax and Rex proteins.

In certain embodiments, the recombinant attenuated BLV may comprise the mutation in G4 restricting the propagation of the BLV in vivo, and the mutation in R3 restricting the propagation of the BLV in vivo, and the mutation in the X region of the BLV nucleic acid sequence abolishing the production of at least one or preferably all microRNA encoded by said X region, wherein said mutations are a deletion of at least a portion of the region of the BLV nucleic acid sequence between the stop codon of TM and the splice acceptor site of intron 2 of Tax/Rex, whereby the splice acceptor site of intron 2 of R3 and the splice acceptor site of intron 1 of G4 are deleted. In further embodiments, such recombinant attenuated BLV may further comprise the mutation in the nucleic acid sequence encoding the most N-terminal YXXL signalling motif of the cytoplasmic domain of the transmembrane subunit (TM) of the envelope protein, said mutation disrupting the signal transduction activity of the motif, as disclosed herein.

For example, the 5' boundary of the deletion may be located between about 1 and about 50, preferably between about 1 and about 40, more preferably between about 1 and about 30, even more preferably between about 1 and about 20, still more preferably between about 1 and about 11, such as at about 7, nucleotides downstream of the stop codon of TM.

Any of such exemplary 5' boundaries of the deletion listed in the previous paragraph may be combined with a 3' boundary of the deletion located between about 178 and about 3 nucleotides upstream of the intron 2-exon 3 boundary of Tax/Rex, or any of such exemplary 5' boundaries of the deletion listed in the previous paragraph may be combined with a 3' boundary of the deletion located between about 100 and about 3 nucleotides upstream of the intron 2-exon 3 boundary of Tax/Rex, or any of such exemplary 5' boundaries of the deletion listed in the previous paragraph may be combined with a 3' boundary of the deletion located between about 55 and about 35 nucleotides upstream of the intron 2-exon 3 boundary of Tax/Rex, or any of such exemplary 5' boundaries of the deletion listed in the previous paragraph may be combined with a 3' boundary of the deletion at about 45 nucleotides upstream of the intron 2-exon 3 boundary of Tax/Rex.

For example, the 5' boundary of the deletion may be located between about 1 and about 50, preferably between about 1 and about 40, more preferably between about 1 and about 30, even more preferably between about 1 and about 20, still more preferably between about 1 and about 11, such as at about 7, nucleotides downstream of the stop codon of TM, and the 3' boundary of the deletion may be located between about 178 and about 3, or preferably between about 100 and about 3, or more preferably between about 55 and about 35, or still more preferably at about 45 nucleotides upstream of the intron 2-exon 3 boundary of Tax/Rex.

In a particular example, the 5' boundary of the deletion may be located between about 1 and about 11, e.g., at about 7, nucleotides downstream of the stop codon of TM and the 3' boundary of the deletion may located between about 55 and about 35, e.g., at about 45, nucleotides upstream of the intron 2-exon 3 boundary of Tax/Rex.

In further preferred embodiments, the 5' boundary of the deletion may be located between positions 6163 and 6213, or preferably between positions 6163 and 6203, or more preferably between positions 6163 and 6193, or even more preferably between positions 6163 and 6183, or still more preferably between positions 6163 and 6173, or particularly preferably at about position 6169 of the BLV nucleic acid sequence according to "Rice" sequence numbering and the 3' boundary of the deletion may be located between positions 6957 and 7037, or preferably between positions 6967 and 7027, or more preferably between positions 6977 and 7017, or even more preferably between positions 6987 and 7007, or still more preferably at about position 6997 of the BLV nucleic acid sequence according to "Rice" sequence numbering.

In a particular example, the 5' boundary of the deletion may be located between positions 6163 and 6173, e.g., at about position 6169, of the BLV nucleic acid sequence and the 3' boundary of the deletion may be located between positions 6987 and 7007, e.g., at about position 6997, of the BLV nucleic acid sequence.

In certain embodiments, the invention provides the recombinant attenuated BLV as taught herein, preferably wherein the BLV is BLV isolate 344, and wherein one of the following applies:

the recombinant attenuated BLV comprises a substitution of a T nucleotide at position 6073 of the BLV nucleic acid sequence with a G nucleotide and further comprises a deletion of the BLV nucleic acid sequence between positions 6614 and 6848; or the recombinant attenuated BLV comprises a substitution of a T nucleotide at position 6073 of the BLV nucleic acid sequence with a G nucleotide and further comprises a double oligonucleotide segment comprising a stop codon inserted into the BamHI site at position 6997 of the BLV nucleic acid sequence such that said stop codon is in-frame to the G4 ORF, preferably wherein the double oligonucleotide segment is composed of two hybridised oligonucleotides each with the sequence 5'-GATCTAGGCTAGAATTCTAGCCTA-3' (SEQ ID NO: 3), inserted into the BamHI site at position 6997 of the BLV nucleic acid sequence; or the recombinant attenuated BLV comprises a substitution of a T nucleotide at position 6073 of the BLV nucleic acid sequence with a G nucleotide and further comprises a double oligonucleotide segment replacing the nucleic acid segment between XbaI site at position 6614 and BamHI site at position 6997 of the BLV nucleic acid sequence, preferably wherein the double oligonucleotide segment is composed of two hybridised oligonucleotides with the sequences 5'-CTAGAAAGCTTG-3' (SEQ ID NO: 1) and 5'-GATCCAAGCTTT-3' (SEQ ID NO: 2), respectively, replacing the nucleic acid segment between XbaI site at position 6614 and BamHI site at position 6997 of the BLV nucleic acid sequence; or
- the recombinant attenuated BLV comprises a deletion of the BLV nucleic acid sequence between positions 6169 and 6997, preferably the recombinant attenuated BLV comprises the nucleic acid sequence 5'-TCTAGAAAGCTT-3' (SEQ ID NO: 4) replacing the nucleic acid sequence from position 6170 to position 6996 of the BLV nucleic acid sequence; or
- the recombinant attenuated BLV comprises a substitution of a T nucleotide at position 6073 of the BLV nucleic acid sequence with a G nucleotide and further comprises a deletion of the BLV nucleic acid sequence between positions 6169 and 6997, preferably the recombinant attenuated BLV comprises a substitution of a T nucleotide at position 6073 of the BLV nucleic acid sequence with a G nucleotide and further comprises the nucleic acid sequence 5'-TCTAGAAAGCTT-3' (SEQ ID NO: 4) replacing the nucleic acid sequence from position 6170 to position 6996 of the BLV nucleic acid sequence.

As already noted, aspect of the invention provides the recombinant attenuated BLV encoded by the plasmid as deposited under the Budapest Treaty with the Belgian Coordinated Collections of Microorganisms BCCM™/LMBP Collection under accession number LMBP 8166 on Feb. 5, 2013 (see Table 2B). This encodes the BLV6073DX provirus as described in the experimental section.

As already noted, aspect of the invention provides the recombinant attenuated BLV encoded by the plasmid as deposited under the Budapest Treaty with the Belgian Coordinated Collections of Microorganisms BCCM/LMBP Collection under accession number LMBP 8166 on Feb. 5, 2013 (see Table 2B). This encodes the BLV6073DX provirus as described in the experimental section.

As also already noted, aspect of the invention provides the recombinant attenuated BLV encoded by the plasmid as deposited under the Budapest Treaty with the Belgian Coordinated Collections of Microorganisms BCCM/LMBP Collection under accession number LMBP 8167 on Feb. 5, 2013 (see Table 2C). This encodes the BLVGPDX provirus as described in the experimental section.

As also already noted, aspect of the invention provides the recombinant attenuated BLV encoded by the plasmid as deposited under the Budapest Treaty with the Belgian Coordinated Collections of Microorganisms BCCM/LMBP Collection under accession number LMBP 8713 on Oct. 25, 2013 (see Table 2D). This encodes the BLV6073GPDX provirus as described in the experimental section.

A further aspect provides a recombinant nucleic acid encoding the recombinant attenuated BLV as disclosed herein.

By "nucleic acid" is meant oligomers and polymers of any length composed essentially of nucleotides, e.g., deoxyribonucleotides and/or ribonucleotides. Nucleic acids can comprise purine and/or pyrimidine bases and/or other natural (e.g., xanthine, inosine, hypoxanthine), chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted sugars and/or one or more modified or substituted phosphate groups.

Modifications of phosphate groups or sugars may be introduced to improve stability, resistance to enzymatic degradation, or some other useful property. A "nucleic acid" can be for example double-stranded, partly double stranded, or single-stranded. Where single-stranded, the nucleic acid can be the sense strand or the antisense strand. In addition, nucleic acid can be circular or linear. The term "nucleic acid" as used herein preferably encompasses DNA and RNA, specifically including RNA, genomic RNA, cDNA, DNA, provirus, pre-mRNA and mRNA.

The term "oligonucleotide" as used herein refers to a nucleic acid oligomer or polymer as defined herein. Preferably, an oligonucleotide is (substantially) single-stranded. Oligonucleotides as intended herein may be preferably between about 10 and about 100 nucleoside units (i.e., nucleotides) in length, preferably between about 15 and about 50, more preferably between about 15 and about 40, also preferably between about 20 and about 30.

With the term "provirus" is meant herein the reverse transcribed genome of a virus, in particular a retrovirus, that is integrated into the DNA genome of a host cell. The term also includes isolated forms of proviruses and genetic constructs containing such.

In preferred embodiments, the recombinant nucleic acid encoding the recombinant attenuated BLV disclosed herein is recombinant DNA. By means of example, said DNA may comprise, consist essentially of or consist of isolated provirus.

In a further aspect, the invention provides a vector comprising the recombinant nucleic acid disclosed herein.

The term "vector" encompasses nucleic acid molecules, typically DNA, to which nucleic acid fragments, preferably the recombinant nucleic acid disclosed herein, may be inserted and cloned, i.e., propagated. Hence, a vector will typically contain one or more unique restriction sites, and may be capable of autonomous replication in a defined host or vehicle organism such that the cloned sequence is reproducible. A vector may also preferably contain a selection marker, such as e.g. an antibiotic resistance gene, to allow selection of recipient cells that contain the vector. Vectors may include, without limitation, plasmids, phagemids, bacteriophages, bacteriophage-derived vectors, PAC, BAC, linear nucleic acids, e.g., linear DNA, etc., as appropriate (see, e.g., Sambrook et al., 1989; Ausubel 1992).

Factors of importance in selecting a particular vector include inter alia: choice of recipient host cell, ease with which recipient cells that contain the vector may be recognised and selected from those recipient cells which do not contain the vector; the number of copies of the vector which are desired in particular recipient cells; whether it is desired for the vector to integrate into the chromosome or to remain extra-chromosomal in the recipient cells; and whether it is desirable to be able to "shuttle" the vector between recipient cells of different species.

Preferred vectors comprise a selection marker. Preferably, the selection marker is not an ampicillin resistance gene, which helps to avoid issues of subject sensitivity to beta-lactams. A suitable selection marker may include, for example, but without limitation, a kanamycin resistance gene. Another suitable selection marker may include an auxotrophic selection marker for use with auxotrophic recipient cells as known per se. The auxotrophic growth-based selection system is based on the restoration of growth of auxotrophic recipient cells (i.e., recipient cells that lack a functional essential gene for growth) upon introducing a plasmid that allows expression of the functional gene product (i.e., a plasmid comprising an auxotrophic selection marker). The recipient cells are first modified, e.g., by introducing a deletion or a nonsense point mutation into an essential or conditionally essential chromosomal gene, resulting in auxotrophy, and the plasmid comprises e.g., the deleted gene or encodes a suppressor tRNA which allows a complete translation of the truncated gene product.

Preferred vectors are plasmids, more preferably bacterial plasmids or yeast shuttle vectors.

Non-limiting examples of suitable bacterial plasmids are those capable of replication in *E. coli*, such as, for example, pSP64.

With the term "yeast shuttle vector" is meant herein a plasmid capable of cloning in yeast, preferably *Saccharomyces cerevisiae*, but also capable of replication in a bacterial host, preferably *E. coli*. Such shuttle vectors typically comprise a genetic element, preferably an origin of replication, which enable the plasmid to be propagated in a bacterial host, preferably *E. coli*, a selectable marker for the bacterial host, a selectable marker for the yeast, and a multiple cloning site.

Preferred yeast shuttle vectors are yeast integrative plasmids, yeast episomal plasmids, or yeast centromeric plasmids.

With the term "yeast integrative plasmid" is meant herein a yeast plasmid which by homologous recombination is integrated into the host genome. A non-limiting example of a yeast integrative plasmid is pRS306.

With "yeast episomal plasmids" are meant herein yeast plasmids which maintain as episomes in the host. Such episomal plasmids typically comprise part of the 2μ plasmid DNA sequence necessary for autonomous replication. A non-limiting example of a yeast episomal plasmid is pRS426.

The term "yeast centromeric plasmid" denotes a yeast plasmid which replicates autonomously and controlled in a way that the copy number of the self-replicated plasmid is just one. A yeast centromeric plasmid may typically comprise a yeast origin of replication (ARS sequence) and a centromeric sequence which guarantees stable mitotic segregation. A non-limiting example of a yeast centromeric plasmid is pRS316.

In preferred embodiments, the vector disclosed herein may be selected from the group comprising or consisting of: a bacterial plasmid, a yeast integrative plasmid, a yeast episomal plasmid, and a yeast centromeric plasmid.

A further aspect provides the plasmid as deposited under the Budapest Treaty with the Belgian Coordinated Collections of Microorganisms BCCM/LMBP Collection under accession number LMBP 8166 on Feb. 5, 2013 (see Table 2B). The plasmid corresponds to the pBLV6073DX plasmid as described in the experimental section.

A further aspect provides the plasmid as deposited under the Budapest Treaty with the Belgian Coordinated Collections of Microorganisms BCCM/LMBP Collection under accession number LMBP 8167 on Feb. 5, 2013 (see Table 2C). The plasmid corresponds to the pBLVGPDX plasmid as described in the experimental section.

A further aspect provides the plasmid as deposited under the Budapest Treaty with the Belgian Coordinated Collections of Microorganisms BCCM/LMBP Collection under accession number LMBP 8713 on Oct. 25, 2013 (see Table 2D). The plasmid corresponds to the pBLV6073GPDX plasmid as described in the experimental section.

Further aspects provide a recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8166 on Feb. 5, 2013 (see Table 2B), and a vector comprising the recombinant nucleic acid.

Further aspects provide a recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8167 on Feb. 5, 2013 (see Table 2C), and a vector comprising the recombinant nucleic acid.

Further aspects provide a recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8713 on Oct. 25, 2013 (see Table 2D), and a vector comprising the recombinant nucleic acid.

The invention further provides a host cell comprising the recombinant attenuated BLV, the recombinant nucleic acid, the vector, or the plasmid as taught herein. The terms "host cell" and may suitably refer to cells encompassing both prokaryotic cells, such as bacteria, and eukaryotic cells, such as yeast, fungi, protozoan, plant and animal cells. A host cell may particularly refer to an isolated host cell, e.g., a host cell maintained and/or propagated in laboratory conditions, e.g., in microbiological culture or in cell or tissue culture.

In preferred embodiments, the host cell may be a bacterial cell, a yeast cell, an animal cell, or a mammalian cell.

Non-limiting examples of suitable bacterial cells include *Escherichia coli*, such as, e.g., *E. coli* strain STBL2™ (competent cells) (Invitrogen; genotype and background: [F-mcrA Δ(mcrBC-hsdRMSmrr) recA1 endA1 gyrA96 thi supE44 relA1λ-Δ(lac-proAB)]) or SURE (Stratagene; genotype and background: e14-(McrA-) Δ(mcrCB-hsdSMR-mrr) 171 endA1 gyrA96 thi-1 supE44 relA1 lac recB recJ sbcC umuC:Tn5 (Kanr) uvrC [F' proAB lacIqZΔM15 Tn10 (Tetr)]); *Yersinia enterocolitica*; or *Brucella* sp., such as, e.g., *Brucella abortus* strain S19 or strain RB51. Other non-limiting examples of suitable bacterial cells include, e.g., *Salmonella* tymphimurium, *Serratia marcescens*, or *Bacillus subtilis*. Preferably, such bacteria, e.g., *E. coli*, may carry at least the recA, in order to reduce or prevent recombination of direct repeats in the BLV provirus plasmid.

A non-limiting example of a suitable yeast cell includes yeast of the genera *Saccharomyces, Schizosaccharomyces*, or *Pichia*, e.g., *Saccharomyces cerevisiae, Schizosaccharomyces pombe*, or *Pichia pastoris*.

Non-limiting examples of suitable animal cells may include human and non-human animal cells, such as vertebrate animal cells, mammalian cells, primate cells, human cells or insect cells.

Animal cells, such as mammalian cells, such as human or non-human mammalian cells, may include primary cells, secondary, tertiary etc. cells, or may include immortalised cell lines, including clonal cell lines. Preferred animal cells can be readily maintained and transformed in tissue culture.

Preferred but non-limiting example of human cells include the human HeLa (cervical cancer) cell line. Other human cell lines common in tissue culture practice include inter alia DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), U87 (glioblastoma), SHSY5Y (neuroblastoma), or Saos-2 cells (bone cancer).

A non-limiting example of primate cells are Vero (African green monkey Chlorocebus kidney epithelial cell line) cells.

Non-limiting examples of rodent cells are rat GH3 (pituitary tumor) or PC12 (pheochromocytoma) cell lines, or mouse MC3T3 (embryonic calvarium) cell line.

Non-limiting examples of insect cells include cells derived from *Drosophila melanogaster* such as Schneider 2 cells, cell lines derived from the army worm *Spodoptera frugiperda*, such as Sf9 and Sf21 cells, or cells derived from the cabbage looper *Trichoplusia ni*, such as High Five cells.

Methods for introducing nucleic acids, including vectors, into a host cell (i.e., transfection or transformation) are known to the person skilled in the art, and may include calcium phosphate co-precipitation, electroporation, microinjection, lipofection, transfection employing polyamine transfection reagents, bombardment of cells by nucleic acid-coated tungsten micro projectiles, etc.

The host cells as taught herein may be live or may be inactivated (i.e., dead) by a suitable cell inactivation procedure, e.g. by freeze-drying, sonication or irradiation.

The recombinant attenuated BLV, the recombinant nucleic acid, the vector, the plasmid or the host cell as taught herein may be formulated in a pharmaceutical composition with a pharmaceutically acceptable excipient, i.e., one or more pharmaceutically acceptable carrier substances and/or additives, e.g., buffers, carriers, excipients, stabilisers, etc. The term "pharmaceutically acceptable" as used herein is consistent with the art and means compatible with the other ingredients of the pharmaceutical composition and not deleterious to the recipient thereof.

Accordingly, in a further aspect the invention provides a pharmaceutical composition comprising the recombinant attenuated BLV, the recombinant nucleic acid, the vector, the plasmid, or the host cell as disclosed herein.

In a related aspect the invention provides the recombinant attenuated BLV, the recombinant nucleic acid, the vector, the plasmid, or the host cell as disclosed herein for use in medicine.

Also disclosed herein is the use of the recombinant attenuated BLV, the recombinant nucleic acid, the vector, the plasmid, or the host cell as taught herein, for the production of a medicament.

For example, host cells as disclosed herein may be allowed to produce and optionally secrete recombinant attenuated BLV particles, which require expression of the proviral sequence, packaging of the viral genome into a capsid, a complex formation of envelope proteins with cell membranes and budding of the virion similar to natural infection. The harvested viral particles may optionally after further purification and/or processing steps such as lyophilisation, suspended in a medium suitable for administration. The recombinant attenuated BLV particles may be lyophilized in the presence of common excipients such as lactose, other sugars, alkaline and/or alkali earth stearate, carbonate and/or sulphate (for example, magnesium stearate, sodium carbonate and sodium sulphate), kaolin, silica, flavourants and aromas.

In another example, the vectors disclosed herein, preferably the proviral plasmids disclosed herein (i.e., plasmids comprising recombinant BLV provirus), may be allowed to propagate into an appropriate host cell, after which the purified vectors may be formulated with cationic liposomes, such as, e.g., N-(1-(2,3-dioleoyloxy)propyl)-N,N,N-trimethylammonium methylsulfate (DOTAP), in a medium suitable for administration.

In yet another example, the host cell disclosed herein may be cultured, upon which the harvested cells, optionally after further purification and/or processing steps, such as freeze-drying, sonication or irradiation to inactivate them, can be used to prepare the formulation. Such formulations include but are not limited to live or inactivated (i.e., dead), e.g., by freeze-drying, sonication or irradiation, bacteria, yeast or mammalian cells, such as, e.g., HeLa cells, comprising a proviral DNA plasmid or episome or proviral DNA integrated in their genome and a medium suitable for administration.

In preferred embodiments, the pharmaceutical composition may be a vaccine.

In a related aspect the invention provides the recombinant attenuated BLV, the recombinant nucleic acid, the vector, the plasmid, the host cell, or the pharmaceutical composition as disclosed herein, for use as a vaccine, in particular for use as a vaccine against a BLV-associated disease, more in particular for use as a prophylactic vaccine against a BLV-associated disease. As discussed elsewhere in this specification, such vaccine may advantageously be intended for long-term protection (e.g., protection for at least 18 months or for at least 24 months or for at least 36 months or for at least 48 months post-vaccination) of animals, preferably bovids, more preferably cattle, from infection by wild-type BLV (which may be heterologous to the vaccine). Such vaccine may so-protect virtually all animals, preferably bovids, more preferably cattle, e.g., at least 90%, preferably at least 95%, such as 98%, or 99%, or even 100% of the vaccinated animals.

Also disclosed herein is the use of the recombinant attenuated BLV, the recombinant nucleic acid, the vector, the plasmid or the host cell as taught herein, for the production of such vaccine.

A vaccine may typically comprise an immunologically effective amount of an immunogenic substance or composition.

The term "immunologically effective amount" refers to an amount of an immunogenic substance or composition effective to enhance the immune response of a subject against a subsequent exposure to the immunogen. Levels of induced immunity can be determined, e.g. by measuring amounts of neutralizing secretory and/or serum antibodies, e.g., by plaque neutralization, complement fixation, enzyme-linked immunosorbent, or microneutralization assay.

By means of example, an immunologically effective amount of the recombinant nucleic acid, the vector, or the plasmid as taught herein may comprise at least about 25 ng nucleic acid, or at least at least about 50 ng nucleic acid, or at least about 100 ng nucleic acid, or at least at least about 250 ng nucleic acid, or at least at least about 500 ng nucleic acid, or at least at least about 750 ng nucleic acid, or at least at least about 1 µg nucleic acid, or at least at least about 2 µg nucleic acid, or at least at least about 5 µg nucleic acid, or at least at least about 10 µg nucleic acid, or at least at least about 50 µg nucleic acid, or at least at least about 100 µg nucleic acid, e.g., in a single or repeated dose. Dosages of the nucleic acid for administration will vary depending upon any number of factors including the type of BLV mutant, the subject, the route of administration to be used, prevalence of the disease to be treated, etc. Thus, precise dosages cannot be defined for each and every embodiment of the invention, but will be readily apparent to those skilled in the art once armed with the present invention.

By means of example, an immunologically effective amount of a vaccine comprising host cells, e.g., bacteria, comprising proviral plasmid may comprise at least $10^4$ bacteria, or at least $10^5$ bacteria, or at least $10^6$ bacteria, or at least $10^7$ bacteria, or at least $10^8$ bacteria, or at least $10^9$, or at least $10^{10}$, or at least $10^{11}$, or at least $10^{12}$, or at least $10^{13}$, or at least $10^{14}$, or at least $10^{15}$, or more bacteria, e.g., in a single or repeated dose. Dosages of host cells for administration will vary depending upon any number of factors including the type of host cell, expression levels, the route of administration to be used, prevalence of the disease to be treated, etc. Thus, precise dosages cannot be defined for each and every embodiment of the invention, but will be readily apparent to those skilled in the art once armed with the present invention.

The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), *Corynebacterium parvum*, and the synthetic adjuvant QS-21.

Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In preferred embodiments the vaccine as taught herein may comprise one or more further immunogenic substances or compositions.

Any substance or composition capable of eliciting an immune response may be added to the vaccine. By means of example, but without limitation, such immunogenic substance may be a recombinant nucleic acid, e.g. a plasmid, comprising coding sequences for epitopes or antigens; or live attenuated viruses, e.g. in the form of a proviral plasmid; or live attenuated bacteria. For example, vaccines comprising host cells, e.g. bacteria, as disclosed herein may comprise a BLV proviral plasmid and one or more plasmids comprising coding sequences for antigens or epitopes.

Such combination vaccines may be aimed at preventing several diseases or one disease caused by different variants of the same organism causing the disease.

Suitable immunogenic substances for use in a combination with the vaccine disclosed herein are without limitation live attenuated bovine herpesvirus, such as e.g. live attenuated bovine herpesvirus type I, or live attenuated *Clostridium* sp.

The invention further provides the recombinant attenuated BLV, the recombinant nucleic acid, the vector, the plasmid, the host cell, or the pharmaceutical composition as disclosed herein, for use in treatment of a BLV-associated disease, in particular for use in prevention (i.e., preventative treatment, prophylactic treatment, prophylaxis) of a BLV-associated disease.

The term "BLV-associated disease" as intended herein generally encompasses any disease and disorder caused by BLV infection.

BLV-associated diseases include inter alia and preferably enzootic bovine leukosis, which may include bovine persistent lymphosis, bovine lymphosarcoma and bovine lymphoma.

As used herein, the terms "treat" or "treatment" refer to both therapeutic treatment and prophylactic or preventative measures. The terms "treatment", "treating", and the like, as used herein include amelioration or elimination of a developed disease or condition once it has been established or alleviation of the characteristic symptoms of such disease or condition. As used herein these terms preferably encompass, depending on the condition of the subject, preventing the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement.

In preferred embodiments, the treatment is prophylactic treatment, such as preferably prophylactic vaccination, whereby (super)infection with another BLV virus may be prevented.

The recombinant attenuated BLV, the recombinant nucleic acid, the vector, the plasmid, the host cell, or the pharmaceutical composition such as vaccine as disclosed herein may in certain embodiments benefit from more than one administration to a subject. Hence, in such embodiments, following an initial administration of the recombinant attenuated BLV, the recombinant nucleic acid, the vector, the plasmid, the host cell, or the pharmaceutical composition such as vaccine as disclosed herein to a subject (such initial administration may be denoted as primary antigen stimulation or "priming"), one or more subsequent administrations (such subsequent administration(s) may be denoted as "boosting") of the recombinant attenuated BLV, the recombinant nucleic acid, the vector, the plasmid, the host cell, or the pharmaceutical composition such as vaccine as disclosed herein to the subject may be advantageous to sustain or preferably increase the anti-viral immune response in the subject.

In certain embodiments, such "boosting" may involve repeated administrations of the recombinant attenuated BLV, the recombinant nucleic acid, the vector, the plasmid, the host cell, or the pharmaceutical composition such as vaccine as disclosed herein at regular intervals following the initial administration, e.g., at a regular interval of about 0.5 year, or about 1.0 year, or about 1.5 year or about 2.0 years or about 2.5 years, or about 3 years, or about 4 years, or about 5 years, preferably at an interval of about 1.0 year or about 2.0 years, even more preferably at an interval of about 1.0 year. In this context, such "repeated" administrations may mean for example two or more administrations, three or more administrations, four or more administrations or five or more administrations following the initial administration. In an example, "repeated" administrations may mean that such administrations are repeated throughout the entire lifetime of a subject.

The term "subject" as used herein particularly refers to animals, more particularly to mammals, such as non-human mammals, and most particularly to bovides. Bovides are cloven-hoofed ruminant mammals belonging to the Bovidae family. Members include, for example, but without limitation bison, African buffalo, water buffalo, antelopes, gazelles, sheep, goats, muskoxen, and domestic cattle. Preferred bovides are bovines, such as, e.g., buffalos, zebus and domestic cattle, particularly animals belonging to the genus *Bos*, more particularly *Bos primigenius*, including cattle (cows), more preferably cattle (cows). Hence, in preferred embodiments, the subject is a bovid, more preferably a bovine, even more preferably cattle, such as a cow.

The invention further pertains to a non-human animal, preferably a non-human mammal, more preferably a bovid, even more preferably a bovine, such as cattle, to which the recombinant attenuated BLV, the recombinant nucleic acid, the vector, the plasmid, the host cell, or the pharmaceutical composition as disclosed herein has been administered. Examples of non-human animals useful in this context include without limitation cows, pigs, donkeys, horses, rabbits, goats, sheep, guinea pigs, rats, mice, and the like.

Such non-human animal may harbour in the genome of at least some of its cells, preferably in the genome of at least some of its peripheral blood mononuclear cells (PBMC), a provirus encoding the recombinant attenuated bovine leukemia virus as taught herein.

The invention thus also provides methods for preparing a non-human animal-derived material, comprising obtaining material from the non-human animal as taught here above (e.g., by milking, or by slaughtering the animal), and optionally further processing said material into a non-human animal-derived product (e.g., portioning, treating with preservatives, packaging, etc.).

The invention further provides a non-human animal-derived material or a non-human animal-derived product obtainable or directly obtained from said non-human animal, or obtainable or directly obtained by said method.

In preferred embodiments, the non-human animal-derived material or the non-human animal-derived product may comprise, consist of or may be isolated from a secretion of the mammary gland of the non-human animal or a part thereof, in particular wherein the material or product comprises, consists of or is isolated from milk or colostrum.

In other preferred embodiments, the non-human animal-derived material or the non-human animal-derived product may comprise, consist of or may be isolated from whole blood of the non-human animal, in particular wherein the material or product comprises, consists of or is whole blood, or fraction of whole blood, such as plasma or serum.

The invention further pertains to said non-human animal-derived material or said non-human animal-derived product for use as a vaccine, in particular for use as a vaccine against a BLV-associated disease, more in particular for use as a prophylactic vaccine against a BLV-associated disease.

It shall be appreciated that such non-human animal-derived material or said non-human animal-derived product may thus contain the attenuated BLV virus, or the BLV provirus or cells containing such, or may contain antibodies that have been raised against the attenuated BLV virus in the subject from which the material or product is obtained (i.e., passive immunisation).

Deposits of Biological Material

The following Tables 2A, 2B, 2C and 2D summarise the requisite indications relating to deposited microorganisms or other biological material referred to throughout this specification.

TABLE 2A

| Indications relating to the deposited plasmid pBLV344H. | |
|---|---|
| Accession number given by depositary institution | LMBP 8165 |
| Identification reference given by the depositor | pBLV344H |
| Suitable host organism identified by the depositor | *E. coli* STBL2 ™ (competent cells) (Invitrogen) or SURE (Stratagene) |
| Name of depositary institution | Belgian Coordinated Collections of Microorganisms (BCCM) Universiteit Gent Vakgroep Moleculaire Biologie - Plasmidecollectie (BCCM/LMBP) |
| Address of depositary institution | Technologiepark 927 B-9052 Zwijnaarde Belgium |
| Date of deposit | Feb. 5, 2013 |

TABLE 2A-continued

Indications relating to the deposited plasmid pBLV344H.

| | |
|---|---|
| Name of depositor | University of Liège (Université de Liège) |
| Address of depositor | Gembloux Agro-Bio Tech |
| | Place du 20 août, 7 |
| | 4000 Liège |
| | Belgium |
| Scientific description of the deposited material | The plasmid contains a wild-type bovine leukemia virus (strain 344) and flanking cellular sequences cloned into pSP64 (Van den Broeke et al. 1988, Proc. Natl. Acad. Sci. USA 85: 9263-9267). BLV 344 provirus is cloned in the plasmid pSP64 (Promega Corp., Madison, WI, USA; Cat. no. P1241; GenBank acc. no. X65328.2), which comprises ori and $amp^R$ for propagation and selection, thereby yielding the plasmid pBLV344H as described in Willems et al. 1993 (J. Virol. 67: 4078-4085). Diagnostic restriction sites are HindIII (1 fragment of 12.5 KB and absence of any other bands generated by undesired recombination; if present, perform DNA isolation ("minipreps") and isolate individual clones lacking recombined plasmid), EcoRI (4.4 KB + 8.1 KB) and BamHI (7.4 KB + 2 KB + 3.1 KB). |

TABLE 2B

Indications relating to the deposited plasmid pBLV6073DX.

| | |
|---|---|
| Accession number given by depositary institution | LMBP 8166 |
| Identification reference given by the depositor | pBLV6073DX |
| Suitable host organism identified by the depositor | *E. coli* STBL2 ™ (competent cells) (Invitrogen) or SURE (Stratagene) |
| Name of depositary institution | Belgian Coordinated Collections of Microorganisms (BCCM) Universiteit Gent Vakgroep Moleculaire Biologie - Plasmidecollectie (BCCM/LMBP) |
| Address of depositary institution | Technologiepark 927 |
| | B-9052 Zwijnaarde |
| | Belgium |
| Date of deposit | Feb. 5, 2013 |
| Name of depositor | University of Liège (Université de Liège) |
| Address of depositor | Gembloux Agro-Bio Tech |
| | Place du 20 août, 7 |
| | 4000 Liège |
| | Belgium |
| Scientific description of the deposited material | The plasmid contains an attenuated bovine leukemia virus (strain 344) and flanking cellular sequences cloned into pSP64. The recombinant attenuated BLV comprises a substitution of a T nucleotide at position 6073 (according to Rice et al. 1987, "Sequence analysis of the bovine leukemia virus genome", In A. BURNEY and M. MAMMERICKX (ed.), Enzootic bovine leukosis and bovine leukemia virus. Martinus Nijhof, Leiden, The Netherlands, pp. 115-144) of the BLV nucleic acid sequence with a G nucleotide and further comprises a double oligonucleotide segment (5'-CTAGAAAGCTTG-3' and 5'-GATCCAAGCTTT-3') replacing the nucleic acid segment between XbaI site at position 6614 AND BamHI site at position 6997 of the BLV nucleic acid sequence. Diagnostic restriction sites are KpnI (1 fragment of 12.1 KB and absence of any other bands generated by undesired recombination; if present, perform DNA isolation ("minipreps") and isolate individual clones lacking recombined plasmid), HindIII (2.1 KB + 10 KB), EcoRI (4.4 KB + 7.7 KB) and BamHI (7.4 KB + 2 KB + 2.7 KB). |

TABLE 2C

Indications relating to the deposited plasmid pBLVGPDX.

| | |
|---|---|
| Accession number given by depositary institution | LMBP 8167 |
| Identification reference given by the depositor | pBLVGPDX |
| Suitable host organism identified by the depositor | *E. coli* STBL2 ™ (competent cells) (Invitrogen) or SURE (Stratagene) |
| Name of depositary institution | Belgian Coordinated Collections of Microorganisms (BCCM) Universiteit Gent Vakgroep Moleculaire Biologie - Plasmidecollectie (BCCM/LMBP) |

TABLE 2C-continued

Indications relating to the deposited plasmid pBLVGPDX.

| | |
|---|---|
| Address of depositary institution | Technologiepark 927<br>B-9052 Zwijnaarde<br>Belgium |
| Date of deposit | Feb. 5, 2013 |
| Name of depositor | University of Liège (Université de Liège) |
| Address of depositor | Gembloux Agro-Bio Tech<br>Place du 20 août, 7<br>4000 Liège<br>Belgium |
| Scientific description of the deposited material | The plasmid contains an attenuated bovine leukemia virus (strain 344) and flanking cellular sequences cloned into pSP64. The recombinant attenuated BLV comprises a double oligonucleotide segment composed of two hybridised oligonucleotides with the sequences 5'-CTAGAAAGCTTG-3' (SEQ ID NO: 1) and 5'-GATCCAAGCTTT-3' (SEQ ID NO: 2), respectively, replacing the nucleic acid segment between XbaI site at position 6169 and BamHI site at position 6997 of the BLV nucleic acid sequence. Diagnostic restriction sites are KpnI (1 fragment of 11.6 KB and absence of any other bands generated by undesired recombination; if present, perform DNA isolation ("minipreps") and isolate individual clones lacking recombined plasmid), HindIII (2.1 KB + 9.5 KB), EcoRI (4.4 KB + 7.2 KB) and BamHI (7.4 KB + 2 KB + 2.3 KB). |

TABLE 2D

Indications relating to the deposited plasmid pBLV6073GPDX.

| | |
|---|---|
| Accession number given by depositary institution | LMBP 8713 |
| Identification reference given by the depositor | pBLV6073GPDX |
| Suitable host organism identified by the depositor | *E. coli* STBL2 ™ (competent cells) (Invitrogen) or SURE (Stratagene) |
| Name of depositary institution | Belgian Coordinated Collections of Microorganisms (BCCM)<br>Universiteit Gent Vakgroep Moleculaire Biologie - Plasmidecollectie (BCCM/LMBP) |
| Address of depositary institution | Technologiepark 927<br>B-9052 Zwijnaarde<br>Belgium |
| Date of deposit | Oct. 25, 2013 |
| Name of depositor | University of Liège (Université de Liège) |
| Address of depositor | ULg Gembloux Agro-Bio Tech<br>Place du 20 août, 7<br>4000 Liège<br>Belgium |
| Scientific description of the deposited material | The plasmid contains an attenuated bovine leukemia virus (strain 344) and flanking cellular sequences cloned into pSP64. The recombinant attenuated BLV comprises a substitution of a T nucleotide at position 6073 (according to Rice et al. 1987, "Sequence analysis of the bovine leukemia virus genome", In A. BURNEY and M. MAMMERICKX (ed.), Enzootic bovine leukosis and bovine leukemia virus. Martinus Nijhof, Leiden, The Netherlands, pp. 115-144) of the BLV nucleic acid sequence with a G nucleotide. The recombinant attenuated BLV further comprises a double oligonucleotide segment composed of two hybridised oligonucleotides with the sequences 5'-CTAGAAAGCTTG-3' (SEQ ID NO: 1) and 5'-GATCCAAGCTTT-3' (SEQ ID NO: 2), respectively, replacing the nucleic acid segment between XbaI site at position 6169 and BamHI site at position 6997 of the BLV nucleic acid sequence. Diagnostic restriction sites are KpnI (1 fragment of 11.6 KB and absence of any other bands generated by undesired recombination; if present, perform DNA isolation ("minipreps") and isolate individual clones lacking recombined plasmid), HindIII (2.1 KB + 9.5 KB), EcoRI (4.4 KB + 7.2 KB) and BamHI (7.4 KB + 2 KB + 2.3 KB). |

EXAMPLES

Example 1 Design and Construction of Wild-Type and Mutant BLV Provirus Plasmids The recombinant bovine leukemia virus (BLV) provirus plasmid pBLV6073DX is derived from the plasmid pBLV344H described in Willems et al. 1993 (J. Virol. 67: 4078-4085), specifically incorporated by reference herein. pBLV344H comprises complete wild-type BLV provirus derived from infected tissues of the sheep animal 344 experimentally infected with a Belgian variant of BLV, as described by Van den Broeke et al. 1988 (Proc. Natl. Acad. Sci. USA 85: 9263-9267), specifically incorporated by reference herein. The plasmid pBLV344H has been deposited under the Budapest Treaty with the Belgian Coordinated Collections of Microorganisms BCCM/LMBP Collection under accession number LMBP 8165 on Feb. 5, 2013 (see Table 2A).

Figure 1G:
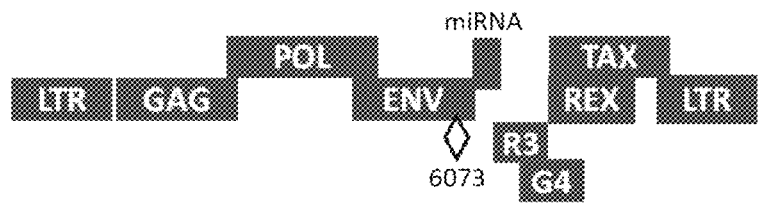
Figure 1H:
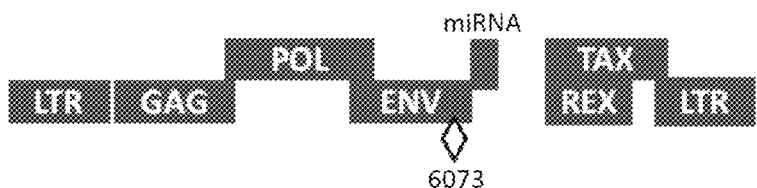
Figure 1I:
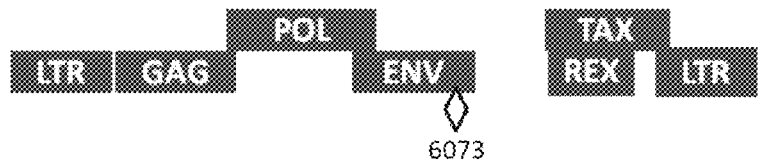
Figure 1J:
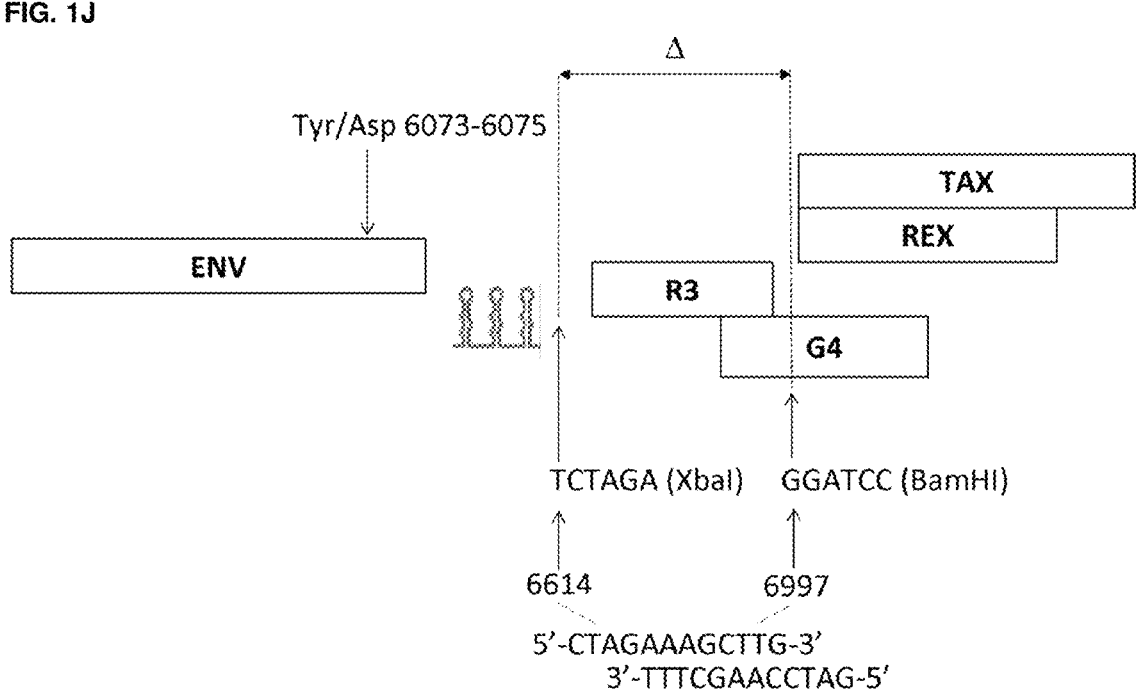

The recombinant BLV provirus plasmid pBLV6073DX was constructed using standard molecular cloning techniques. Schematically, the KpnI-XbaI fragment of pBLV6073 (positions 2111-6614; size 4.5 Kbp) was ligated to the XbaI-KpnI fragment of pBLVDX (position 6997-2111 (XbaI site at adjacent to position 6997 in pBLVDX was introduced through cloning, see below); size 4.7 Kbp). Nucleotide positions of BLV proviruses are numbered in this specification according to the sequence as described in Rice et al. 1987 supra, a certain portion of which is reproduced in FIG. 1D. Nucleotide 1 is the first at the 5' end of the R region of the 5' long terminal repeat (LTR). pBLV6073DX (FIG. 1H) carries both the mutation at position 6073 of pBLV6073 and the deletions in the R3 and G4 ORFs of pBLVDX. More specifically, pBLV6073DX carries a substitution of a T nucleotide at position 6073 of the BLV nucleic acid sequence with a G nucleotide and further comprises a double oligonucleotide segment composed of two hybridised oligonucleotides with the sequences 5'-CTAGAAAGCTTG-3' (SEQ ID NO: 1) and 5'-GATCCAAGCTTT-3' (SEQ ID NO: 2), respectively, replacing the nucleic acid segment between XbaI site at position 6614 and BamHI site at position 6997 of the BLV nucleic acid sequence (FIG. 1J).

The pBLV6073 recombinant BLV provirus plasmid is derived from the plasmid pBLV344H using PCR-based site-directed mutagenesis procedure as described in Willems et al. 1995 (J. Virol. 69: 4137-4141), specifically incorporated by reference herein. pBLV6073 carries a substitution of a T residue with a G residue at position 6073 in an immunoreceptor tyrosine-based activation motif (ITAM) located in the transmembrane protein gp30 of the envelope (FIG. 1G).

The pBLVDX recombinant BLV provirus plasmid is derived from the plasmid pBLV344H by cloning a double oligonucleotide segment composed of two hybridised oligonucleotides with the sequences 5'-CTAGAAAGCTTG-3' (SEQ ID NO: 1) and 5'-GATCCAAGCTTT-3' (SEQ ID NO: 2) into the XbaI and BamHI restriction sites (positions 6614 and 6997) of pBLV344H, as described in Willems et al. 1993 (J. Virol. 67: 4078-4085), specifically incorporated by reference herein. pBLVDX carries deletions in the R3 and G4 open reading frames (ORFs) (FIG. 1F). pBLV6073DX has been deposited under the Budapest Treaty with the Belgian Coordinated Collections of Microorganisms BCCM™/LMBP Collection under accession number LMBP 8166 on Feb. 5, 2013 (see Table 2B).

Example 2 Set-Up of a Delivery System

A protocol was developed based on transient transfection of HeLa cells with proviral plasmids and subsequent subcutaneous or intradermal injection. In particular, two 150 cm$^2$ Petri dishes of subconfluent HeLa cell monolayers were transfected with pBLV6073DX (35 μg per plate) complexed (ratio 1:5) with transfection reagent (TransIT®, Mirus Bio LCC or FuGENE®, Roche). After 2 days of culture (37° C. in a 95%-5% air-CO$_2$ humidified atmosphere) in complete (i.e., supplemented with 10% foetal calf serum (FCS), 2 mM L-glutamine, 100 U of penicillin, 100 μg of streptomycin per ml) Dulbecco's Modified Eagle Medium (DMEM, Invitrogen), transfected cells were trypsinised, washed in phosphate-buffered saline (PBS) and injected subcutaneously.

This delivery protocol provides an alternative to more familiar protocols, such as infection by BLV or injection of purified proviral DNA, and offers certain advantages over such protocols. For example, natural infection by BLV requires expression of the viral RNA genome, its packaging into a capsid, a complex formation of envelope proteins with cell membranes and budding of the virion. However, in this extracellular form, the viral particle is comparatively unstable. This can also be avoided, for instance, by infecting animals by injection of purified proviral DNA. For example, packaging proviral DNA into cationic liposomes and intradermal injection permits viral infection. However, this technique requires production and purification of large quantities of plasmid DNA (100-500 micrograms per animal), and infection through direct DNA injection tends to be comparatively less efficient, potentially necessitating a second injection and/or extending the latency period before seroconversion.

We also developed another strategy based on intradermal injection of the *E. coli* strain STBL2™ (competent cells) ([F-mcrA Δ(mcrBC-hsdRMSmrr) recA1 endA1 gyrA96 thi supE44 relA1λ-A(lac-proAB)]; Trinh et al. (1994, FOCUS 16: 78)); available from Invitrogen carrying the proviral plasmid. STBL2™ (competent cells) cells transformed with pBLV6073DX were cultured overnight in 5 ml of Luria-Bertani (LB) broth medium (Invitrogen) containing 50 μg/ml of ampicillin at 28° C. Bacteria were then centrifuged, washed, resuspended in 2 ml of PBS and injected subcutaneously or intradermally.

This straightforward and cost-effective technique of injecting STBL2™ (competent cells) cells carrying the proviral plasmid very reproducibly transmitted infection to naïve hosts after a single injection. No side or toxic effects of STBL2™ (competent cells) cell injection were recorded, in agreement with its safety data sheet. Advantageously, using bacterial cells instead of mammalian cells such as the human HeLa cells, avoids the risk of inadvertently introducing other pathogens, such as HPV, and reduces the complexity of vaccine formulations based on cells (e.g., bacterial cells need not be preserved in liquid nitrogen when transported).

Experiments detailed below were performed using subcutaneous injection of HeLa cells carrying the proviral plasmids. Comparable results are obtained using subcutaneous injection of *E. coli* strain STBL2™ (competent cells) carrying the proviral plasmids.

Experiments detailed below were performed using subcutaneous injection of HeLa cells carrying the proviral plasmids. Comparable results are obtained using subcutaneous injection of *E. coli* strain STBL2™ carrying the proviral plasmids.

Example 3 the Recombinant BLV6073DX Provirus is Infectious and Elicits a Strong Anti-Viral Immune Response, but Replicates at Reduced Levels A preliminary trial performed under restricted conditions demonstrated that the recombinant BLV6073DX provirus is safe because of the: (i) absence of pathology or toxicity in vaccinated cows and in the highly susceptible ovine experimental model, (ii) lack of transmission of the recombinant BLV6073DX provirus to uninfected sentinels over a 3 year period, (iii) absence of detectable levels of plasmid DNA (including the β-lactamase gene) as revealed by nested PCR (data not shown).

A large scale experimental setting was designed. Ten cows were infected with recombinant BLV6073DX provirus (i.e., vaccinated) and 5 others were infected with wild-type BLV provirus (WT). All cows were then kept in a herd of 74-82 animals (depending on the year) among which about 15-30% were naturally infected with Argentinean BLV strain (ArgWT). Besides vaccine efficacy, this design also allows an evaluation of safety under real farm conditions (i.e., transmission from cow to calf and infection of sentinels).

As revealed by a competitive ELISA test (ELISA Bovine Leukosis Serum blocking test, Institut Pourquier), injection of pBLV6073DX elicited an antiviral antibody response with kinetics similar to wild-type infection (FIG. 2A). Importantly, the antibody titres were not statistically different between vaccinated and wild-type infected animals (FIG. 2B).

Proviral loads were measured by qPCR. Briefly, peripheral blood mononuclear cells (PBMCs) were isolated by Percoll density gradient centrifugation (GE Healthcare) and washed twice with phosphate-buffered saline (PBS)/0.075% EDTA and at least three times with PBS alone. DNA was isolated using DNeasy Blood and Tissue kit (Qiagen) according to the manufacturer instructions. One hundred nanograms of genomic DNA were used for real-time PCR amplification of BLV proviral sequences. A segment corresponding to the pol gene was amplified using primers 5'-GAAACTCCAGAGCAATGGCATAA-3' (SEQ ID NO: 5) and 5'-GGTTCGGCCATCGAGACA-3' (SEQ ID NO: 6) and MESA GREEN mPCR MasterMix (Eurogentec) on a light cycler (Roche) following manufacturer instructions. A standard curve was generated after amplification of defined proviral copy numbers (from $10^2$ to $10^6$ of plasmid pBLV344) diluted in 100 ng of control genomic DNA. To correct for differences in DNA concentrations the actin DNA was quantified in parallel using primers 5'-TCCCTGGAGAAGAGCTACGA-3' (SEQ ID NO: 7) and 5'-GGCAGACTTAGCCTCCAGTG-3' (SEQ ID NO: 8). Thermal conditions: 95° C. 5 min; (95° C. 15 sec, 60° C. 20 sec, 72° C. 40 sec, 45 times). Proviral load was calculated from the number of proviral copies divided by half of the number of actin copies and expressed as number of proviral copies per 100 of PBMCs.

The proviral loads (PVL) were significantly reduced in vaccinated animals (FIG. 3). Indeed, the numbers of proviral copies per 100 peripheral blood mononuclear cells (PBMCs) were typically below 2 in cows infected with the recombinant BLV6073DX. In wild-type infected cows, the PVLs were up to 100 fold higher.

Importantly, no pathogenicity of BLV6073DX was observed in any of the 10 vaccinated cows in a period of almost 3.5 years post-inoculation (vaccination on 21 Oct. 2010). Similarly, none of the 3 cows used in the preliminary trial displayed any pathogenicity of BLV6073DX in a period of almost 5.5 years post-inoculation (vaccination on Oct. 10, 2008). Also, two sheep used in earlier trial studies and vaccinated with BLV6073DX have not shown any pathogenicity of BLV6073DX in a period of about 4 and 5 years post-inoculation. The absence of detectable pathogenicity in these experiments corroborates the suitability of BLV6073DX as a safe vaccine, emphasising its superiority over BLV6073, which caused pathogenicity in 1 of 4 sheep, and BLVDX, which caused pathogenicity in 1 of 8 sheep (Florins et al. 2007 supra).

Additionally, sequencing studies performed on the vaccinated animals have confirmed that BLV6073DX was not subject to mutations in the inoculated animals, thereby further corroborating the vaccine's stability and safety.

Preliminary experiments also supported the conclusion that BLV6073DX advantageously induces a cytotoxic immune response in vaccinated cows.

Figure 4B:

Example 4 Animals Vaccinated with BLV6073DX Provirus do not Become Infected with Wild-Type Virus in Herd Conditions For traceability, a protocol was designed to identify vaccinated animals based on nested PCR using primers that flank the deletion in the R3 and G4 ORFs of pBLV6073DX (FIG. 4). Briefly, peripheral blood mononuclear cells (PBMCs) were isolated from blood using Ficoll® according to the manufacturer instructions (Sigma Aldrich). DNA was isolated using DNeasy Blood and Tissue kit (Qiagen) according to the manufacturer instructions. Two hundred and fifty nanograms of DNA were used for the first round of PCR reaction (PCR1) using Phusion hot start II High Fidely DNA polymerase in the High Fidelity buffer (Thermoscientific). One microliter of a 10-fold diluted PCR1 was used as template for the second round of PCR (nested PCR) using the same DNA polymerase and buffer condition. Thermal protocol for PCR1: 98° C. 30 sec; (98° C. 5 sec, 64° C. 10 sec, 72° C. 30 sec, 35 times); 72° C. 2 min. Thermal protocol for nested PCR: 98° C. 30 sec; (98° C. 5 sec, 70° C. 10 sec, 72° C. 30 sec, 35 times); 72° C. 2 min. Primer sequences for PCR1: Fw 5'-CTCACTTCTGCTTCACCATCC-3' (SEQ ID NO: 9); Rv 5'-GGCAGGCATGTAGAGAGTGG-3' (SEQ ID NO: 10). Primer sequences for nested PCR: nFw 5'-TGGAAAGAACTAACGCTGACGG-3' (SEQ ID NO: 11); nRv 5'-CCCCAACCAACAACACTTGCTT-3' (SEQ ID NO: 12). A third PCR reaction was performed using 250 ng of DNA to amplify a fragment of the actin gene as control using the same conditions. Thermal protocol for control actin PCR: 98° C. 30 sec; (98° C. 5 sec, 64° C. 10 sec, 72° C. 30 sec, 35 times); 72° C. 2 min. Primer sequences for control actin PCR: Fw 5'-TCCCTGGAGAAGAGCTACGA-3' (SEQ ID NO: 7); Rv 5'-GGCAGACTTAGCCTCCAGTG-3' (SEQ ID NO: 8).

The protocol effectively identified the 10 vaccinated cows, i.e., the cows infected with the recombinant BLV6073DX provirus, as demonstrated by the amplification of the small fragment (FIG. 5). A large fragment was amplified in the wild-type BLV infected animals (FIG. 5). As control, no amplification occurred in two uninfected calves and in the absence of DNA (water) (FIG. 5). The data thus demonstrate that the 10 vaccinated cows kept in a wild-type BLV-infected herd carried genetic sequences corresponding to the recombinant BLV6073DX provirus, but not to the wild-type BLV provirus. This type of profile was preserved since Oct. 19, 2010.

Since all animals were kept in the same herd, these data also show that the wild-type provirus does not transmit to vaccinated cows, suggesting that the recombinant BLV6073DX provirus efficiently protects against superinfection. Of note, the pBLV6073DX plasmid originates from wild-type BLV strain 344, which is different from Argentinean BLV variants. This observation thus indicates that infection with recombinant BLV6073DX provirus (i.e., vaccination) protects against infection of heterologous BLV viruses.

The observation that all 10 vaccinated cattle remained free of wild-type BLV virus for almost 3.5 years post-vaccination corroborates the advantages of BLV6073DX as a vaccine with a comparatively long-term protective effect, e.g., protective effect of at least 18 months, preferably at least 24 months, more preferably at least 36 months, even more preferably at least 48 months or even longer post-vaccination, in animals, especially in cattle. In contrast, one of two cows vaccinated using the previously existing pBLVDX provirus became infected by wild-type BLV 12 months after challenge (Kerkhofs et al. 2000 supra), and one cow (#269) vaccinated using the previously existing pBLV6073 provirus became infected by wild-type BLV 24 months after challenge (Kerkhofs et al. 2000 supra, and Example 10).

Example 5 the Recombinant BLV6073DX Provirus Protects Against Wild-Type BLV Challenge We designed a trial to evaluate the ability of vaccinated (i.e., infected with recombinant BLV6073DX provirus) animals to resist challenge with wild-type BLV provirus. Briefly, 60 μg of pBLVWT plasmid DNA (corresponding to $6 \times 10^{12}$ wild-type proviral copies) were transfected into HeLa cells (two 15 cm diameter subconfluent Petri dishes) and, after 48 hours, the transfected HeLa cells were injected subcutaneously into the back of 3 vaccinated animals and 3 uninfected controls.

Infection with wild-type BLV provirus was assessed by a competitive ELISA to determine seropositivity and anti-BLV antibody titres as described in Example 3 and nested PCR according to the protocol described in Example 4 to detect the presence of WT BLV provirus.

Two months post-injection, the 3 controls (#77, #83 and #85) became infected with the wild-type provirus as demonstrated by nested PCR and ELISA (Table 3, FIG. 6). In contrast, wild-type BLV sequences were absent in vaccinated animals (#322, #357 and #360) as demonstrated by nested PCR (Table 3, FIG. 6).

TABLE 3

Infection with wild-type BLV provirus in vaccinated or uninfected animals following challenge with wild-type BLV provirus. A sample is considered seropositive if the ratio of the sample OD to the negative control OD is at least 40%. The antibody titre is expressed as the inverted dilution of the sample that yields 50% of the maximal OD of the test sample (without normalization to a positive control).

| Inoculum | Animal ID | Seropositivity | Anti-BLV antibody titre | Presence of WT BLV provirus |
|---|---|---|---|---|
| pBLV6073DX | 322 | + | 12 | − |
| pBLV6073DX | 351 | + | 12 | − |
| pBLV6073DX | 360 | + | 6 | − |
| control | 77 | + | 60 | + |
| control | 83 | + | 180 | + |
| control | 85 | + | 180 | + |

The data clearly demonstrate that vaccinated animals resist challenge by wild-type BLV.

Example 6 Vaccinated Cows Transmit Passive Immunity but not Infection to their Calves Transmission of the recombinant BLV6073DX provirus from the cows to their calves was analyzed by inseminating animals and analyzing infection in the calves using nested PCR as described in Example 4.

Among four calves from wild-type infected cows, one (#100) became infected (Table 4). This pattern is consistent with previous observations describing intrauterine or perinatal transmission of BLV infection.

In contrast, proviral sequences could not be amplified in any of the 6 calves born from vaccinated cows, indicating that the pBLV6073DX provirus plasmid was not transmitted (Table 4). Importantly, these calves contained anti-BLV antibodies in their serum revealing passive immunity. The antibody titres persisted a few months and then slowly decreased with time further supporting lack of infection of vaccinated cows progeny. It should also be mentioned that we did observe neither signs of abortion in vaccinated cows nor side effects in their calves (e.g., weight, abnormalities, disease, . . . ).

TABLE 4

Transmission of infection from infected cows to calves (non-inf. = non-infected).

| | WT infected cows | | | BLV6073DX infected cows | | | | |
|---|---|---|---|---|---|---|---|---|
| Cow | 21 | 492 | 535 | 28 | 42 | 43 | 45 | 55 |
| Calf | 104 non-inf. | 88 non-inf. | 100 WT infected<br>109 non-inf. | 84 non-inf. | 87 non-inf.<br>113 non-inf. | 98 non-inf. | 102 non-inf. | 114 non-inf. |

In summary, cows vaccinated with pBLV6073DX transmit anti-BLV passive immunity but not viral infection to their calves.

Examples 1 to 6 set forth above demonstrate that by combining a mutation at residue 6073 and a deletion of the R3/G4 genes in an embodiment of the invention, a BLV strain has been achieved that (i) is infectious in cows but transmits neither to their offspring nor to sentinels, (ii) replicates at low levels compared to wild type but lacks pathogenicity, (iii) elicits a strong immune response and protects from wild type challenge, and (iv) is readily traceable by PCR. This attenuated strain can therefore be used as a protective vaccine against BLV infection.

Example 7 Infectivity of Recombinant BLVGPX Provirus In Vivo

A recombinant BLV provirus plasmid pBLVGPX carrying a deletion of the microRNAs ORFs, in particular harbouring a deletion between positions 6169 and 6731 (numbering as described in Rice et al. 1987 supra) in the X region between the env gene and the Tax/Rex sequences has been described in Willems et al. (2000, AIDS Res Hum Retroviruses. 16: 1787-95), specifically incorporated by reference herein.

pBLVGPX was derived from the plasmid pBLV344H (see Example 1). Schematically, 5' proviral sequences were PCR-amplified using the upstream primer 5'-TGACAA-CATATAACCAAGA-3' (SEQ ID NO: 17) (Rice positions 4751-4769) and the downstream primer 5'-TCTAGAGGGGGTGTCAAGGGCAGGGT-3' (SEQ ID NO: 13). Nucleotides 7-26 of this downstream primer are complementary to BLV positions 6169-6150, and nucleotides 1-6 of the primer introduce an XbaI restriction site (underlined) at the 3' end of the resulting PCR product. Thermal conditions for PCR: 95° C. 5 min; (95° C. 30 sec, 57° C. 30 sec, 72° C. 60 sec, 36 times); 72° C. 5 min. The amplicon was cloned into plasmid pCRII (Invitrogen) yielding pCREA. To construct pBLVGPX, 4 fragments were ligated: a 68 bp BglII-XbaI fragment of pCREA (BglII at positions 6101-6106 of BLV), and 3 fragments from pBLV344H(XbaI-KpnI 8 kb, KpnI-NcoI 2.8 kb and NcoI-BglII 1.2 kb). pBLV344H was described in Willems et al. 1993 (J. Virol. 67: 4078-4085).

Proviral loads were measured by qPCR, as described in Example 3. The recombinant BLVGPX provirus is infectious in vivo in cows (FIG. 7A) and in sheep (FIG. 7B). Interestingly, however, while the infectivity (proviral loads) of BLVGPX in sheep is virtually the same as the infectivity of wild-type BLV (FIG. 7B), the infectivity (proviral loads) of BLVGPX in cows tends to be lower than the infectivity of the wild-type BLV (FIG. 7A). It is thus unexpected that the combination of the mutation in BLVGPX with the mutation in BLVDX (resulting in BLVGPDX) or with the mutations in BLV6073DX (resulting in BLV6073GPDX), rather than being deleterious for the recombinant BLV (e.g., completely destroying infectivity of BLVGPDX or BLV6073GPDX in animals, such as particularly in cattle), preserves satisfactory levels of infectivity of the recombinant BLV and reduces or eliminates its pathogenicity, thereby achieving greatly improved attenuated vaccines in animals, particularly in cattle.

Example 8 Design and Construction of Recombinant BLVGPDX and BLV6073GPDX Provirus Recombinant BLV provirus plasmids pBLVGPDX and pBLV6073GPDX are constructed using standard molecular cloning techniques.

pBLVGPDX was derived from the plasmid pBLV344H (see Example 1). Schematically, 5' proviral sequences were PCR-amplified using the upstream primer 5'-TGACAA-CATATAACCAAGA-3' (SEQ ID NO: 17) (Rice positions 4751-4769) and the downstream primer 5'-TCTAGAGGGGGTGTCAAGGGCAGGGT-3' (SEQ ID NO: 13). Nucleotides 7-26 of this downstream primer are complementary to BLV positions 6169-6150, and nucleotides 1-6 of the primer introduce an XbaI restriction site (underlined) at the 3' end of the resulting PCR product. Thermal conditions for PCR: 95° C. 5 min; (95° C. 30 sec, 57° C. 30 sec, 72° C. 60 sec, 36 times); 72° C. 5 min. The amplicon was cloned into plasmid pCRII (Invitrogen) yielding pCREA. To construct pBLVGPDX, 4 fragments were ligated: a 68 bp BglII-XbaI fragment of pCREA (BglII at positions 6101-6106 of BLV), and 3 fragments from pBLV344H(BamHI-KpnI 8.3 kb, KpnI-NcoI 2.8 kb and NcoI-BglII 1.2 kb). A double oligonucleotide linker segment composed of two hybridised oligonucleotides with the sequences 5'-CTAGAAAGCTTG-3' (SEQ ID NO: 1) and 5'-GATCCAAGCTTT-3' (SEQ ID NO: 2) was used to connect the XbaI and BamHI overhangs. As a result, the nucleic acid sequence 5'-TCTAGAAAGCTT-3' (SEQ ID NO: 4) replaces the nucleic acid sequence between position 6170 and position 6996 of the BLV nucleic acid sequence (numbering as described in Rice et al. 1987 supra). pBLVGPDX has been deposited under the Budapest Treaty with the Belgian Coordinated Collections of Microorganisms BCCM/LMBP Collection under accession number LMBP 8167 on Feb. 5, 2013 (see Table 2C).

Subsequently, PCR-based site-directed mutagenesis was performed with QuikChange XL Site-Directed Mutagenesis Kit (Agilent) using the primers 6073S: 5'-GATTCTGAT-GATCAGGCCT-3' (SEQ ID NO: 14) and 6073C: 5'-AGGCCTGATCATCAGAATC-3' (SEQ ID NO: 15) to introduce the 6073 mutation.

The recombinant BLV6073GPDX provirus (FIG. 1I) carries the 6073 mutation, i.e., a substitution of a T residue with a G residue at position 6073 in an ITAM located in the transmembrane protein gp30 of the envelope, and a deletion between position 6169 and position 6997 (numbering as described in Rice et al. 1987 supra). Hence, the recombinant BLV6073GPDX provirus also carries a deletion in the miRNAs, R3 and G4 ORFs.

pBLV6073GPDX has been deposited under the Budapest Treaty with the Belgian Coordinated Collections of Microorganisms BCCM/LMBP Collection under accession number LMBP 8713 on Oct. 25, 2013 (see Table 2D).

The recombinant BLVGPDX provirus and the recombinant BLV6073GPDX provirus are each expected to provide a particularly advantageous BLV strain displaying at least some and preferably all of the following properties: (i) it is infectious in cows but transmits neither to their offspring nor to sentinels, (ii) it replicates at low levels compared to wild type but lacks pathogenicity, (iii) it elicits a strong immune response and protects from wild type challenge, and (iv) it is readily traceable by PCR. This attenuated strain can therefore be used as a protective vaccine against BLV infection.

One sheep (#2187) was infected with provirus pBLV6073GPDX using the following protocol. Two 15 cm-diameter dishes containing subconfluent Hela cells were transfected with 10 micrograms of plasmid pBLV6073GPDX, recovered in 5 ml PBS at day 3 and injected subcutaneously into sheep 2187. Infection was confirmed by competitive ELISA revealing the presence of anti-BLV antibodies and by PCR-sequencing demonstrating the presence of the mutations. No pathogenicity has been observed in sheep 2187 in almost 6 months (vaccination on 18 Sep. 2013).

In another trial, 50 calves are vaccinated with pBLV6073GPDX. pBLV6073GPDX will display long-term protection (e.g., at least 18 months, preferably at least 24 months, more preferably at least 36 months, even more preferably at least 48 months post-vaccination) of virtually all calves (e.g., at least 90% (45 calves or more), preferably at least 95% (48 calves or more), such as 98% (49 calves), or 99%, or even 100% (50 calves)) from infection by wild-type BLV. pBLV6073GPDX will not cause pathogenicity in the calves over extended time periods (e.g., 3 years, 4 years, 5 years, 6 years, or 7 years or more).

About 500 cows are included in another large-scale vaccination trial in dairy herds with about 80% BLV prevalence in Argentina. Calves (about 40 births per month) are vaccinated with pBLV6073GPDX on day 0 and day 60-90 after birth. Vaccinated heifers are mated at about 17-20 months, giving birth at about 27-30 months, and are followed-up to the age of at least 40 months. BLV6073GPDX will display long-term protection (e.g., at least 18 months, preferably at least 24 months, more preferably at least 36 months, even more preferably at least 48 months post-vaccination) of virtually all cows (e.g., at least 90%, preferably at least 95%, such as 98%, or 99%, or even 100%) from infection by wild-type BLV. BLV6073GPDX will not cause pathogenicity in the cows over the period of the trial. BLV6073DX will not transmit to the offspring of the cows nor to sentinels.

In another trial, 10 calves are vaccinated with pBLVGPDX. pBLVGPDX will display long-term protection (e.g., at least 18 months, preferably at least 24 months, more preferably at least 36 months, even more preferably at least 48 months post-vaccination) of virtually all calves (e.g., at least 90% (9 calves), preferably 100% (10 calves)) from infection by wild-type BLV. pBLVGPDX will not cause pathogenicity in the calves over extended time periods (e.g., 3 years, 4 years, 5 years, 6 years, or 7 years or more).

Example 9 Design and Construction of Further Recombinant BLV Proviruses

By combining specific mutations as described throughout Examples 1-8, various useful embodiments of pBLV344H-derived attenuated recombinant BLV proviruses illustrating the present invention were or are constructed using standard molecular cloning techniques, as listed in Table 5.

TABLE 5

Design of exemplary embodiments of recombinant BLV proviruses as taught herein.

| BLV provirus embodiment #* | Mutations present |
|---|---|
| 1 | 6073 + ΔR3 |
| 2 | 6073 + ΔG4 |
| 3 | 6073 + ΔR3 + ΔG4 |
| 4 = pBLV6073DX | 6073 + Δ(R3 + G4) |
| 5 | ΔmiRNA + ΔG4 |
| 6 = pBLVGPDX | Δ(miRNA + R3 + G4) |
| 7 | 6073 + ΔmiRNA + ΔG4 |
| 8 = pBLV6073GPDX | 6073 + Δ(miRNA + R3 + G4) |

*consecutive numbering solely for the purposes of Table 5.

For the purposes of Table 5:

"6073" denotes a substitution of a T nucleotide at position 6073 of the BLV nucleic acid sequence with a G nucleotide, whereby codon 6073-6075 has been mutated to encode Asp instead of Tyr;

"ΔR3" denotes a deletion of the BLV nucleic acid sequence between positions 6614 and 6848, whereby R3 has been deleted. To construct ΔR3, a BLV fragment was PCR amplified with 2 primers: upstream 5'-TCTAGACAGAGACATTCCAGCCACATC-3' (SEQ ID NO: 18) ("Rice" coordinates 6849-6869, the underlined sequence corresponds to a XbaI site) and downstream 5'-CCTGCATGATCTTTCATACAAAT-3' (SEQ ID NO: 19) ("Rice" coordinates 7999-7977). This insert was digested with EcoRI and XbaI and inserted into the pGEM7 vector (Promega) yielding pGEMXR3. To construct ΔR3, 3 fragments were ligated: 264 bp XbaI-ClaI insert of pGEMXR3, 2 Kb ClaI-HindIII insert of pBLV344H and 10 Kb insert XbaI-HindIII insert of pBLV344H;

"ΔG4" denotes that a double oligonucleotide segment composed of two hybridised oligonucleotides each with the sequence 5'-GATCTAGGCTAGAATTCTAGCCTA-3' (SEQ ID NO: 3) has been inserted into the BamHI site at position 6997 of the BLV nucleic acid sequence, whereby a premature stop codon has been inserted and G4 has been C-terminally truncated;

"Δ(R3+G4)" denotes that a double oligonucleotide segment composed of two hybridised oligonucleotides with the sequences 5'-CTAGAAAGCTTG-3' (SEQ ID NO: 1) and 5'-GATCCAAGCTTT-3' (SEQ ID NO: 2), respectively, has been inserted replacing the nucleic acid segment between XbaI site at position 6614 and BamHI site at position 6997 of the BLV nucleic acid sequence, whereby both R3 and G4 have been deleted;

"ΔmiRNA" denotes a deletion of the BLV nucleic acid sequence between positions 6169 and 6731, whereby the microRNAs ORFs have been deleted, in particular by following the cloning strategy detailed for pBLVGPX in Example 7; and "Δ(miRNA+R3+G4)" denotes a deletion of the BLV nucleic acid sequence between positions 6169 and 6997, whereby the microRNAs ORFs, R3 and G4 have been deleted, in particular by following the cloning strategy detailed for pBLVGPDX in Example 8.

Cows vaccinated in trial studies (for example including about 10 animals or about 50 animals) with attenuated recombinant BLV proviruses exemplified in Table 5 will display long-term protection (e.g., at least 18 months, preferably at least 24 months, more preferably at least 36 months, even more preferably at least 48 months post-vaccination) of virtually all cows (e.g., at least 90%, preferably at least 95%, such as 98%, or 99%, or even 100%) from infection by wild-type BLV. The attenuated recombinant BLV proviruses exemplified in Table 5 will not cause pathogenicity in the cows over extended time periods (e.g., 3 years, 4 years, 5 years, 6 years, or 7 years or more).

Example 10 Wild-Type BLV Infection in Cow #269 Inoculated by BLV6073

As mentioned previously, the present inventors have demonstrated that cow #269 vaccinated using the pBLV6073 provirus and evaluated in Kerkhofs et al. 2000 supra in fact became infected by wild-type BLV 24 months after challenge with wild-type BLV, evidencing that BLV6073 provides for only comparatively short-term protection.

In particular, blood was collected by jugular venipuncture at 18 and 24 months post-challenge of pBLV6073-vaccinated cow #269 (Kerkhofs et al. 2000 supra). After nucleic acid extraction, DNA was amplified by PCR using 3 different pairs of primers: 6073S+7049R (lane 1 in FIG. 8B), 5719S+7049R (lane 2 in FIG. 8B) or 5719S+7000R (lane 3 in FIG. 8B). Primer names correspond to their position on the BLV sequence, and the primer sequences were as follows: 5719S primer (5'-CGGGGGCTTGATTGGTTGTA-3'; SEQ ID NO: 30), 6073S primer (5'-GATTCTGATGATCAGGCCT-3'; SEQ ID NO: 14), 7000R primer (5'-TTGTCGTTATCAGGTAATGGA-3'; SEQ ID NO: 31), and 7049R primer (5'-CCCCAACCAACAACACTTGCTT-3'; SEQ ID NO: 32). These primer pairs surround a small deletion that is present in pBLV6073 but not in wild-type BLV. The position of the primer pairs in wild-type ("WT") and pBLV6073 ("Mutant 6073") sequences is schematically indicated in FIG. 8A. As shown in FIG. 8B, fragments of larger size were amplified at 24 months, suggesting infection of cow #269 by wild-type BLV.

Sequencing of the virus infecting cow #269 confirmed infection by wild-type BLV. In particular, blood was collected by jugular venipuncture at 18 and 24 months post-challenge of pBLV6073-vaccinated cow #269 (Kerkhofs et al. 2000 supra). After nucleic acid extraction, DNA was amplified by PCR using the primer pair 5719S+7000R. The amplification product was sequenced using the primer 5719S. As control, the same experiment was performed with an env gene from a wild-type BLV virus. As shown in FIG. 9, the control wild-type BLV has T at nucleotide position 6073 (FIG. 9, bottom panel, arrow). At 18 months post-challenge, the DNA sample from cow #269 has G at nucleotide position 6073, corresponding to the mutation in pBLV6073 (FIG. 9, top panel, arrow). However, at 24 months post-challenge, the DNA sample from cow #269 has both G (lower peak) and T (higher peak) at nucleotide position 6073, evidencing that cow #269 became infected with wild-type BLV virus (FIG. 9, middle panel, arrow).

Example 11 Vectorisation of BLV6073GPDX for Expression in *Bacillus subtilis*

To introduce AmyE and Lys-A genes of *Bacillus subtilis* strain 168 into the pBLV6073GPDX plasmid, a double recombination strategy is used (see FIG. 10). Therefore, the gene fragment AmyE-F was amplified by PCR from 100 ng of *Bacillus* DNA with Phusion HiFD polymerase using primers amyEF_PciI_UP and amyEF_PciI_RP, and inserted into the Pci1 site of pBLV6073GPDX. Another fragment, AmyEB was amplified by PCR using primers amyE_B_UP and amyE_B_SalI_RP. The LysA gene was amplified by PCR using primers lysA_UP and lysA_RP. These two latter inserts, Amy EB and Lys-A genes were co-amplified with primers LysA UP and amyEF_PciI_RP, and inserted into the Sal1 site of pBLV6073GPDX. PCR conditions for all amplifications were: 98° C. 30 sec; (98° C. 10 sec, 55° C. 15 sec, 72° C. 20 sec, 25 times); 72° C. 10 min. Primer sequences were as follows:

amyEF_PciI_UP:
(SEQ ID NO: 33)
5'-CCTTTTGCTCACATGTAACAAAATTCTCCAGTCTTCACATCGG-3' amyEF_PciI_RP:
(SEQ ID NO: 34)
5'-GCAGGAAAGAACATGTCGATCAGACCAGTTTTTAATTTGTGTG-3' lysA_UP:
(SEQ ID NO: 35)
5'-GTTTTAAACCGTCGATCGCATTGAAACTGACTGAAGAGTATG-3' lysA_RP:
(SEQ ID NO: 36)
5'-ATGTCGAGAAAAGCGCCGAAAAATCG-3'

6'-amyE_B_UP:
(SEQ ID NO: 37)
5'-TTCGGCGCTTTTCTCGACATGGATGAGCGATGATG-3' amyE_B_SalI_RP:
(SEQ ID NO: 38)
5'-GACGTTGACAGTCGACTCAATGGGGAAGAGAACCGC-3'

The resulting construct is transformed in *Bacillus subtilis* 168 amyE+ lysA−. Selection for amyE− lysA+ leads to isolation of a *Bacillus* having integrated the pBLV6073GPDX by homologous recombination.

Sequence Listing Free Text

| | |
|---|---|
| SEQ ID NO: 1 | oligonucleotide |
| SEQ ID NO: 2 | oligonucleotide |
| SEQ ID NO: 3 | oligonucleotide |
| SEQ ID NO: 4 | oligonucleotide |
| SEQ ID NO: 5 | primer for amplification in bovine leukemia virus (BLV) sequence |
| SEQ ID NO: 6 | primer for amplification in bovine leukemia virus (BLV) sequence |
| SEQ ID NO: 7 | primer for amplification in actin sequence |
| SEQ ID NO: 8 | primer for amplification in actin sequence |
| SEQ ID NO: 9 | primer for amplification in bovine leukemia virus (BLV) sequence |
| SEQ ID NO: 10 | primer for amplification in bovine leukemia virus (BLV) sequence |
| SEQ ID NO: 11 | primer for amplification in bovine leukemia virus (BLV) sequence |
| SEQ ID NO: 12 | primer for amplification in bovine leukemia virus (BLV) sequence |
| SEQ ID NO: 13 | primer for amplification in bovine leukemia virus (BLV) sequence |
| SEQ ID NO: 14 | primer for site directed mutagenesis in bovine leukemia virus (BLV) sequence |
| SEQ ID NO: 15 | primer for site directed mutagenesis in bovine leukemia virus (BLV) sequence |
| SEQ ID NO: 17 | primer for amplification in bovine leukemia virus (BLV) sequence |
| SEQ ID NO: 18 | primer for amplification in bovine leukemia virus (BLV) sequence |
| SEQ ID NO: 19 | primer for amplification in bovine leukemia virus (BLV) sequence |
| SEQ ID NO: 30 | primer for amplification in bovine leukemia virus (BLV) sequence |
| SEQ ID NO: 31 | primer for amplification in bovine leukemia virus (BLV) sequence |
| SEQ ID NO: 32 | primer for amplification in bovine leukemia virus (BLV) sequence |
| SEQ ID NO: 33 | primer for amplification in *Bacillus subtilis* |
| SEQ ID NO: 34 | primer for amplification in *Bacillus subtilis* |
| SEQ ID NO: 35 | primer for amplification in *Bacillus subtilis* |
| SEQ ID NO: 36 | primer for amplification in *Bacillus subtilis* |
| SEQ ID NO: 37 | primer for amplification in *Bacillus subtilis* |
| SEQ ID NO: 38 | primer for amplification in *Bacillus subtilis* |

The invention claimed is:

1. A recombinant attenuated BLV encoded by the plasmid as deposited under the Budapest Treaty with the Belgian Coordinated Collections of Microorganisms BCCM/LMBP Collection under accession number LMBP 8713 on Oct. 25, 2013.

2. A recombinant nucleic acid encoding the recombinant attenuated BLV according to claim 1.

3. The recombinant nucleic acid according to claim 2, wherein the nucleic acid is DNA.

4. A vector comprising the recombinant nucleic acid according to claim 2.

5. A plasmid as deposited under the Budapest Treaty with the Belgian Coordinated Collections of Microorganisms BCCM/LMBP Collection under accession number LMBP 8713 on Oct. 25, 2013.

6. A recombinant nucleic acid encoding a recombinant attenuated BLV, wherein the recombinant nucleic acid comprises, consists essentially of or consists of the insert of the plasmid as deposited under the Budapest Treaty with the Belgian Coordinated Collections of Microorganisms BCCM/LMBP Collection under accession number LMBP 8713 on Oct. 25, 2013.

7. A vector comprising the recombinant nucleic acid according to claim 6.

8. An isolated host cell comprising the recombinant attenuated BLV according to claim 1.

9. The host cell according to claim 8, wherein the host cell is a bacterial cell, a yeast cell, an animal cell, or a mammalian cell.

10. The host cell according to claim 8, wherein said host cell is inactivated.

11. A pharmaceutical composition comprising the recombinant attenuated BLV according to claim 1.

12. The pharmaceutical composition according to claim 11, further comprising one or more immunogenic substances or compositions.

13. A method of treatment, comprising: administering the recombinant attenuated BLV according to claim 1 to a subject in need thereof.

14. A method of vaccination, comprising: administering the recombinant attenuated BLV according to claim 1 to a subject in need thereof.

15. A method of treatment of a BLV-associated disease, comprising:
   administering the recombinant attenuated BLV according to claim 1 to a subject in need thereof.

16. The method of claim 15, wherein the subject is a bovid.

17. The method of claim 16, wherein the subject is a bovine.

18. The method of claim 16, wherein the subject is cattle.

* * * * *